United States Patent
Chaudhari et al.

(10) Patent No.: US 7,026,266 B2
(45) Date of Patent: Apr. 11, 2006

(54) CATALYTIC FORMULATION AND ITS PREPARATION

(75) Inventors: Raghunath Vitthal Chaudhari, Maharashtra (IN); Avinash Narendra Mahajan, Maharashtra (IN)

(73) Assignee: Council of Scientific & Industrial Research, New Delhi (IN)

(*) Notice: Subject to any disclaimer, the term of this patent is extended or adjusted under 35 U.S.C. 154(b) by 541 days.

(21) Appl. No.: 09/843,814

(22) Filed: Apr. 30, 2001

(65) Prior Publication Data

US 2003/0092565 A1 May 15, 2003

(51) Int. Cl.
*B01J 31/00* (2006.01)

(52) U.S. Cl. .................. 502/155; 502/166; 502/168; 502/170

(58) Field of Classification Search .......... 502/155, 502/166, 168, 170
See application file for complete search history.

(56) References Cited

U.S. PATENT DOCUMENTS

| | | | |
|---|---|---|---|
| 3,855,307 A | | 12/1974 | Rony et al. |
| 4,248,802 A | | 2/1981 | Kuntz |
| 4,929,767 A | * | 5/1990 | Miller et al. ............. 568/454 |
| 4,994,427 A | | 2/1991 | Davis et al. |
| 5,113,022 A | * | 5/1992 | Abatjoglou et al. ....... 568/454 |

* cited by examiner

Primary Examiner—J. A. Lorengo
Assistant Examiner—J. Pasterczyk
(74) Attorney, Agent, or Firm—Oliff & Berridge, PLC

(57) ABSTRACT

A hetergeneous catalyst includes a solid support having deposited thereon a catalyticaly active material, which is substantially insoluble in organic and aqueous liquid media. The insoluble material is constructed from secondary building blocks derived from suitable organometallic active components, and the organometallic active component may be molecularly modified so as to introduce two or more anionic functional groups. These molecularly modified organometallic components, upon interaction with salts of $Ca^{2+}$, $Sr^{2+}$ and $Ba^{2+}$, provde the practically insoluble solid material. Methods of formuatling the organometallic active materials on a solid support as a solid catalyst are also provided. The catalysts are capable of catalyzing diverse reactions in polar and nonpolar reaction media, and the overall integrity of the formulation as a solid material in a liquid phase provides easy catalyst and product separation.

73 Claims, 4 Drawing Sheets

CATALYTIC FORMULATION AND ITS PREPARATION

FIELD OF THE INVENTION

The present invention relates to a new class of heterogeneous catalysts, the methodology for which is useful in preparing solid catalysts for a variety of chemical reactions. Particularly, this invention relates to a catalyst system comprising of chemical formulation constituting an insoluble material having desired catalytic properties and support, assembled together by a specific technique. The said catalyst is useful for promoting reactions in gas or liquid phase. The unique feature of this catalyst system is that entire catalytic formulation remains as a composite solid material without disassembling during the course of reaction. The invention primarily describes a technique whereby soluble catalyst is converted to insoluble material by appropriate molecular modification. The invention further relates to preferred methods for preparation of such catalytic formulations.

BACKGROUND OF THE INVENTION

Soluble molecular catalysts, particularly complexes of transition metals are well known in the art. Such catalysts are also known to catalyze a variety of useful organic transmformations. These transformations for instance include hydrogenation, hydroformylation, carbonylation, amination, isomerization, telomerization, Heck olefination, Suzuki coupling, metathesis, epoxidation etc. Such transformations find a variety of useful applications for the synthesis of pharmaceuticals, pesticides, solvents and other valuable products of industrial and consumer significance.

Amongst the established practices known in the prior art, catalytically active transition metal complexes have principally been applied in homogeneous form, as solution in a reactant phase. For example, in case of hydroformylation of olefins using rhodium and phosphine ligand complex catalyst wherein phosphine ligand is free of ionic charge such as tributyl phosphine, triphenyl phosphine etc. and soluble in the reaction medium. Although such catalysts are highly effective, in terms of productivity and selectivity, its applicability on practical grounds is often limited to volatile products. In case of reactions catalyzed by homogeneous catalysts involving high molecular weight and especially nonvolatile products catalyst separation is a critical problem. High cost of catalyst, susceptibility to high temperatures and stringent product specification demand quantitative catalyst separation. Common unit operations such as distillation and crystallization are least significant since, organometallic complexes being delicate in nature and cannot withstand separation stresses especially thermal stresses as encountered in distillation. Other separation techniques being inefficient in separating such a small quantity of catalyst cannot be used in effective manner. Moreover high purity of the product is of importance in products such as pharmaceuticals, demanding rigorous separation of catalyst from product stream. Thus use of homogeneous catalyst as such has suffered from inherent difficulties in the recovery of the catalysts from reaction products. Efficient catalyst recovery and recycle is the pivotal issue for the economic viability of the process since, complexes and ligands are often expensive.

It is also known in the art to use aqueous solutions of sulfonated aryl phosphines and many other water-soluble compounds and transition metal complex catalyst derived from it to effect reactions. As disclosed in patent (U.S. Pat. No. 4,248,802) all such reactions are operated in biphasic conditions wherein catalyst phase is aqueous and products and reactants dissolved in organic phase. Similarly reverse biphasic techniques are also applicable wherein catalyst is dissolved in organic phase and product and reactants in aqueous phase. A judicious choice is necessary while utilizing biphasic catalytic systems depending upon solubility of reactants and products. In either case at the end of reaction catalyst and product phases are separated wherefore catalyst phase is recycled and product phase is directed for further downstream processing.

It is however recognized that catalytic activity is low in biphasic medium due to limited solubility of organic reactants in the catalyst phase. Moreover such biphasic reactions require high reactor pressure in case of gas-liquid reactions. To achieve practical rates of reactions catlayst loading has to be increased or alternatively using larger process equipment, which is usually cost prohibitive. Further, these reactions require numerous accessory devices to separate liquid-liquid fractions under reaction conditions.

Over the past quarter of century many attempts have been made to heterogenize this versatile class of soluble catalysts. Several methods were developed with central theme being retention of high activity and selectivity as that of native catalytic species and facilitate separation by simple filtration, centrifugation or gravity settling.

One of the techniques to form a solid catalyst involves interaction of metal salt or precursor complex with solid support that is appropriately functionalized with organic functional groups that are capable of forming coordination bonds with metal. The support used in this context is either organic-polymeric or inorganic matrix. These supports are chemically functionalized to bear amino, phosphino and carboxylato functional groups on the surface of the support. Work related to this technique is described in *Catalysis Reviews*, 16, 17–37 (1974); *Chemical Reviews*, 81, 109, (1981); *Tetrahedron Asymmetry*, 6, 1109–1116 (1995); *Tetrahedron Letters*, 37, 3375–3378 (1996). "*Catalysis by supported complexes*", *Studies in surface science and catalysis*, volume 8, Elsevier Publishing Co. Amsterdam, 1981 describes the complexes grafted to inorganic supports.

From practical stand point these catalysts are not widely used since their activities are frequently lower than corresponding homogeneous catalysts in addition there are various complications that are inherent due to polymeric nature of the support for example swelling and shrinking of the matrix, which alters diffusion resistance. It is also found that in long run and upon exposure to oxygen metal attached to support is lost in the solution thereby degeneration of the activity of the catalyst.

Supported liquid phase catalyst such as those described in U.S. Pat. No. 3,855,307 (1974) and U.S. Pat. No. 4,994,427 (1991) are critically sensitive to the character of the reaction medium and are often leached in to reaction medium depending upon the nature of the solvent. The applicability of such catalyst is limited to only vapor phase reactions. The technique as described in U.S. Pat. No. 4,994,427(1991) wherein solution of water-soluble catalyst is distributed on high surface area solid. The aqueous film of catalyst containing solution remains insoluble in nonpolar organic phase thus, after reaction solid catalyst can be recovered by simple filtration. Appllicability of such catalyst is limited to reactions involving water insoluble reaction media. Moreover such catalysts are sensitive to content of water.

Entrapment of the catalyst in porous material such as zeolite has been described by Balkus, et al in *J. Inclusion*

Phenom. Mol. Recognit. Chem., 21(1–4), 159–84 (English) 1995 The catalyst is encapsulated in three-dimensional network of zeolites wherein, catalyst because of size exclusion can not diffuse out of zeolite but smaller sized reactants diffuse inside the zeolite and products formed subsequently diffuse out. Yet another article J. Catal, 163(2), 457–464 1996 have described the method to entrap catalyst within the polymer matrix but because of diffusion resistance, catalyst efficiency is doubtful.

Despite several known techniques for heterogenization of soluble molecular catalysts there is no known method, which can be conveniently used for diversity of catalytic entities using a common protocol. Furthermore catalyst formed by such protocol is required to provide a solid catalyst that can be used for polar as well as nonpolar reaction media. Certainly a particular need exists for such technique of catalyst formulation and present invention is aimed to fulfill these needs.

DISCLOSURE OF THE INVENTION

Importantly in the general as well as specific background of the art there is no teaching or suggestion of heterogeneous catalyst analogous to supported metal catalyst wherein, catalytically active material is physically distributed on the solid surface and the formulation as a whole can be employed as heterogeneous catalyst which is useful for catalyzing reactions in polar as well as nonpolar solvents. Thus it is an object of this invention to provide a novel catalyst useful for promoting a variety of chemical reactions. More particularly, this invention relates to a catalyst system comprising of calcium, strontium, barium salt of ligand containing at least two or more acidic functional groups and an organometallic catalyst generated from it. These salts are suppored on the solid surface of inert vehicle or carrier. This catalyst is useful for promoting reactions in aqueous, polar and non-polar organic mediums.

Many anionically charged phosphines, and other coordinating compounds as well as variety of their salts are known in the art. It is also known that these ligands and complexes thereof are water-soluble but importantly there is no disclosure or suggestion in open literature, patent or any known reference, indicating an appreciation of any significance, of the formation of insoluble material as alkaline earth metal salts of anionically charged ligands and complexes thereof. Moreover there is no teaching, disclosure or suggestion in any reference known to applicants, evidencing any significance of particular type, class or characteristic of such insoluble organometallic complexes or catalytic application thereof as it relates directly to recovery and recycle of the catalyst.

It has now been discovered that reactions that are catalyzed otherwise by a soluble catalyst can now be catalyzed by the solid catalyst of this invention. The solid catalyst as described herein is not a chemically defined single component catalyst system, but a formulation wherein a solid support and a catalytically active material are assembled together to form a solid catalyst. The support is components, which by itself is catalytically inactive but provides a physical vehicle, filler, and provides a high surface area whereupon catalytically active material is placed. This conglomerate of support and catalytically active material is not a simle random physical mixture, but is assembled in a specific manner such that support is covered or deposited with catlytically active material. Such concepts are known earlier as described in the background of the invention but providing a catalyst suitable only for gas phase or for specific liquid phases, for example, supported aqueous phase catalysts (hereafter termed as SAPC) or supported liquid phase catalysts (hereafter termed as SLPC). SAPC for instance can only be employed in cases where reaction medium is water immiscible organic media. Simiarly, SLPC are suitable only in gas phase but not in general liquid phases.

The surprising element of this invention is that a generic technique is discovered whereby native catalyst, which is otherwise soluble, can be converted to a solid material, which is practically insoluble in organic and aqueous medium. Catalytically active material as said herein is constructed from secondary construction blocks that are derived from catalytically active moieties, when place over a high surface area solid, catalyze a reaction which is otherwise catalyzed by native building species in homogeneous phase but at the same time remaining as solid placed on the support. Due to such reason catalyst as a whole can be separated from reaction mixture by simple solid-liquid separation.

Such catalytic formulation provides a tremendous advantage than catalyzing a reaction by homogeneous or heterogeneous catalyst. This catalyst was conceived in manner analogous to supported heterogeneous catalyst but supported active phase is constructed from molecular entities, which in reality catalyze actual reaction. This particular formulation synergistically combines the desired facile separation and high specificity of the molecular catalysts. The advantages that were obivous to the inventors are;

(a) Solid catalyst providing inherent separation
(b) Activity and selectivity similar to soluble molecular catalysts since active sites are structurally isotropic
(c) Formulation as a whole is mechanically robust material
(d) Modularity of the assembly is such that desired selecting entities, support and additives depending on the need one can assemble the catalyst.

As described herein central them of this discovery is the invention whereby a soluble catalytic material is converted to a solid that is practically insoluble in diversity of liquid media by a systematic molecular modification. It was realized that when soluble catalytic species is modified in such a way that it bears two or more anionic groups existing along with proton, alkali metal ammonium and quaternary ammonium salts. The soluble catalyst modification mentioned here implies that anionic functional groups are introduce while synthesizing components of catalyst or otherwise modifying catalyst as such. Said anionically functionalized salts when interacted with group IIA metal salts provide a solid material that is insoluble in variety of liquid media. This solid material is composed of building blocks of catalytic entities bridged with group IIA metal cation.

Surprisingly in previous patents (U.S. Pat. No. 4,248,802 and U.S. Pat. No. 4,994,427) alkali earth metal salts of such anionically functionalized compounds were claimed in general as aqueous soluble. In this invention disclosure we disclose that alkaline earth metal salts of said anionically functionalized compounds are insoluble in organic media or sparingly soluble or insoluble in aqueous media. Therefore in order to suppress aqueous solubility admixture of catalytically inactive insoluble salts is employed. This admixture is primarily intended to suppress solubility of ionic solids by phenomenon commonly known as common ion effect.

In a manner described earlier, a wide diversity of catalytic complexes can be converted in to solid material by a common protocol. Such solid materials are found to be stable under commonly encountered reaction environments. In another respect, soluble catalysts for diverse classes of reactions, such as for instance hydrogenation, hydroformylation, carbonylation, olefination, telomerization, isomerization, oxidation, etc. can be solified. Yet another aspect of the present invention is the formulation of this material and a solid support to form a catalyst. The support involved here can be chosen independent of catalytic entity being formulated and catalytically inactive additive that is admixed. The most interesting aspect of the present invention is that said catalytic formulation alternatively termed as catalytic ensemble or catalytic assembly, remain as a solid without its component being disintegrated by dissolution. Said ensemble can be employed for catalyzing chemical reactions in slurry or fixed bed reactor configurations.

Thus the precise object of the present invention is to provide a solid catalyst wherein catalytic entities responsible are molecularly defined and isotropic species. More over technique of synthesis should be common set of techniques whereby desired catalytic species can be heterogenized by simple means. The essential object of the present invention is that catalytically active solid formulation should not disintegrate or diassemble under the conditions of reaction as well as under liquid flow. Another desired but not essential object is to provide a solid catalyst that chemically imitates the its soluble analogue but at the same time providing facile separation due to inherent advantages of solid catalysts. The term 'native' used to mean in this context as a catalytic entity before modification and interaction with group IIA metal salts to yield a solid. Other objects and advantages of this invention will become readily apparent from the following written description and appended claims.

Accordingly, generic aspect of the invention can be described as the discovery of a common technique whereby a solid catalyst can be prepared. The family of catalysts that are similar in composition, feature and advantages are referred here by the term generic. The feature of this family of catalyst is that these are heterogeneous but active sites are chemically defined organometallic entities physically existing as solid. These organometallic entities are analogues derived from equivalent homogeneous catalytic entities. Homogeneous catalytic entities referred herein encompass entire class of soluble catalysts. These native structures are chemically modified to introduce negatively charged functional groups such —$SO_3^-$, —$PO_3^{2-}$ or —$COO^-$. When such material are synthesized, they exists as soluble salts depending on the counter ion accompanying anionic functional group. The most intriguing phenomenon realized in this invention itself qualifies to term invention as generic, which is organometallic entities modified as described earlier can be coverted to a solid material by interacting them with group IIA metal salts. The solid formed is ultimately a salt of group IIA metals this observation is validated by converting large diversity of chemical structures to insoluble solids as described earlier moreover methods have been devloped to assemble such solids on the surface of the supports.

DESCRIPTION OF THE PREFERRED EMBODIMENTS

Figure 1:
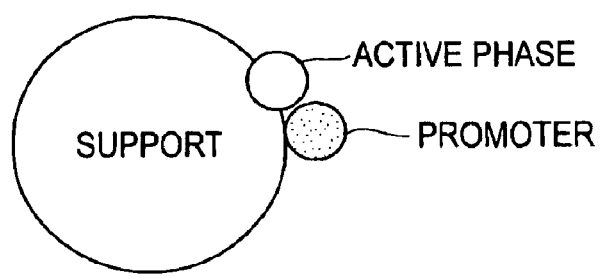
FIG. 1 is the schematic representation of the conceptual representation of the catalyst formulation

For the purposes of promoting an understanding of the principles of the invention, reference will now be made to several embodiments illustrated in the examples and specific description will be made to describe the same. It will nevertheless be understood that no limitation of the scope of the invention is thereby intended, such alterations and further modifications in these embodiments, and such further applications of the principles of the invention as described herein being contemplated as would normally occur to one skilled in the art to which this invention relates.

In one embodiment of the invention, a novel heterogeneous catalytic composition comprising a solid support having deposited theron a catalytically active material which is practically insoluble in variety of liquid media is provided, the said solid material consisting of catalytically active anionic entities with group IIA metal ions and the catalytic active material is molecularly well defined.

In another embodiment of the invention, the catalytically active entity is deposited on the external and the pore surfaces of the solid support, pores of which are predominantly of diameter greater than about 20 A° and the pores of solid support having a pore diameter ranging from about 3–3000 A°.

In still another embodiment, the solid support is chemically inactive solid material, exists as powder, granules, flakes or pallets of regular or irregular shapes, sheets, monolith, ropes and woven fabric of fibrous solids and the porous solid support is mechanically robust and thermally stable solid, insoluble in reaction media.

In still another embodiment, the catalytically active entity is insoluble in reaction media, which are selected from organic, aqueous, flours, non-aqueous ionic liquids and supercritical fluid phases and is thermally stable solid materail having melting point greater than 100° C.

In yet another embodiment, the catalytically active material is a non-subliming solid.

In yet another embodiment of the invention, there is provided a catalyst comprising a solid support having deposited thereon catalytically active entity which remains as a stable composite solid in gas, liquid and gas-liquid phases and the liquid phase is selected from organic, aqueious, fluorous, non-aqueous ionic liquids and supercritical fluid phases or mixture thereof containing reactants, products and promoters.

In yet another embodiment, the catalyst remains as a physically stable composite solid in gas or liquid phases over a temperature range of −78 or 300° C. and over pressure ranging from 5 to 5000 psi.

In yet another embodiment, group IIA metal used is a cation having +2 charge and is selected from calcium, strontium, barium and mixtures thereof.

In yest another embodiment, group IIA metal (also known as group 2 under IUPAC) used is selected independently or in combination with other group IIA metals.

In yet another embodiment, the catalytically active entity is an anion having two or more negative charges and is independently selected from metal complexes, quaternary compounds, metaloxoanions, polyoxometallates and combinations thereof.

In yet another embodiment provides a catalyst wherein, the metal complexes having a general formula

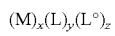

wherein M is catalytic metal atom or ion of a coordination complex is a transtion metal from group IIIB, IVB, VB, VIB, VIIB, IB or IIB of the periodic table of elements and is selected independently, x is ranging from 1 to 60, L is selected from aliphatic, aromatic and heterocyclic compound containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —$SO_3^-$, —$SO_2^-$, —$COO^-$, —$O^-$, $AsO_3^{2-}$ and –$S^-$, y is at least 1, L* is a radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl and Z is ranging from 0 to 7.

In yet another embodiment, the quaternary compound is having a general formula

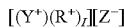

wherein, I=4 for $Y^+=N^+$, $P^+$, $As^+$; I=3 for $Y^+=S^+$ and $R^+$ is selected independently from alkyl, aryl, arylalkyl, alkylaryl, alcoxy, arlyoxy, cycloalkyl bearing at least one or more negatively charged functional groups independently selected from —$SO_3^-$, —$SO_2^-$—$PO_3^{2-}$, —$COO^-$, —$O^-$, $AsO_3^{2-}$ and —$S^-$ and Z is an anion selected from organic anion, inorganic anion and corrdination complex anion.

In yet another embodiment, the insoluble catalytically active material optionally comprising catalytically inert additive, inert additive is an anion having two or more negative charges and which is independently selected from organic, inorganic anions or in combination thereof.

In yet another embodiment, the catalytically inert additive is selected from ligand compounds wherein, ligand compounds contain at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —$SO_3^-$, —$SO_2^-$—$PO_3^{2-}$, —$COO^-$, —$O^-$, $AsO_3^{2-}$ and —$S^-$.

In yet another embodiment, the amount of catalytically active entity employed is 40% weight or less and the amount of catalytically inert additive employed is in the proportion of 0 to 200-weight % of catalytically active entity.

In yet another embodiment, the catalyst can be employed to catalyze reactions in gas phase or in slurry phase.

In yet another embodiment, the catalyst further comprising a film of high boiling liquid deposited on the solid catalyst.

As stated herein above, primary aspect of applicants' invention is directed to a solid formulation as a catalyst comprising of a solid support having deposited thereon a catalytically active solid material. Thus the catalytic formulation referred herein is primarily a solid in physical sense and an organized ensemble of chemical components put together to perform the task of catalyzing the reaction. The definition of assembly is narrowly put down in embodiments that will follow, to conceive a real life catalyst. This multi-component catalyst is the balanced comprise between supposed fluid flow around catalytic particle, activity and a physical integrity. The relative importance of these factors directly affects the reaction, reactor design, process conditions and economics. Although many catalytic materials are composed of single components such as zeolites, pillared clays, metals alloys and metal oxides they certainly cannot catalyze the wide diversity of reactions. Whereas multi-component catalysts as considered in this embodiment offer a choice of physicochemical properties that can be selected from different materials as salts, oxides, metal aggregates or organometallic materials. In order to achieve earlier stated features, this embodiment describes the general architectural draft of catalytic formulation of this invention as illustrated in the FIGS. 1 and 2

Referring to the figure detailed in FIG. 1 components of the said formultion is distinguished into two categories. These two categories are catalytically passive and catalytically active. Passive components are supports and other additives that necessarily impart solid character to catalyst formulation and may be selected independent of active entity depending upon application. Of course it is understood that choice of supports cannot be made randomly and selection is totally dependent on the process. For example silica supports cannot be utilized in strong alkali solutions, as it will dissolve causing the loss of integrity. Thus supports in the context of this embodiment are considered as agents to impart physical shape and form to catalyst particle and act as a vehicle to enhance the maneuverability.

From previous discussion it is explicit enough to judge that catalytically active material is often expensive and sometimes precious, later is often true for reaction that are catalyzed by organometallic complex catalysts. The activity of such materials when supported on solid depends on factors such as surface area, porosity, geometry and resistance to surface fouling. In an effort to optimize these factors, it is common practice to disperse active ingredients on the surface of the inactive solids conventionally known as supports or carriers. Although these materials are considered as diluents, they sometimes play an important multifunctional role in directing catalytic activity. This may include chemical reaction with catalytically active material and they are designated as inactive only to distinguish themselves from bi-functional catalysts, in which support plays a major role in catalytic function. The present embodiment implicitly assumes the possibility of formation of such synergistic multifunctional combination in certain cases.

Accordingly, purpose of employing a support is strongly reasoned due to numerous factors such as ecomonic, process needs and desired physico-chemical properties. The economic reasons as conceived by inventors are mainly cost reduction by extending accessibility of expensive catalytically active material. Further more process needs as recognized by inventors were sufficient mechanical strength imparted to the catalyst, adjustment of bulk density of formed catalyst, to provide heat sink or heat buffer and to dilute the overactive phase. In addition to these, inventors have recognized geometric needs of catalyst that are primarily satisfied by the support can be described as increased the surface area of the catalyst, optimization of porosity of the overal design. Other chemical features inventor feel necessary to state explicity in this embodiment are supports provide a means to reduce sintering or deactivation and may also provide acidic or basic centers which function in synergy with catalytically active material.

Although in principle any stable solid material of high surface area, porosity, strength and required texture is suitable, depending on the particular application under consideration. Most stable range of solids employable herein is alumina, silica, magnesia, Titania, zirconia aluminophosphates, charcoal, organic polymers, and compacted clays. These materials are preferred due to their high surface area, porosity and strength. Apart from these properties they also have low coefficient of thermal expansion.

Nearly all the insulating solids are useful as supports, although on economic grounds alumina and silica are preferred supports. It is recognized from previous reports that oxides such as alumina, silica, zirconia and thoria tend to be acidic. These properties are either of no importance or can be eliminated by selective poisoning. Many naturally occurring materials belong to this group such as pumic asbestors, calcined clays such as bentonite, sepiolite and diatomacious earth such as keisulghur. As a result of wide variation in structure, solids offer range of surface areas and porosity. Although synthetic versions of some materials may be preferred in that they offer more closely defined range of properties. In cases where concerted reactions are required wherein one of the reaction may be catalyzed by support it self. The support can catalyze reaction due to acidic and basic sites available on it or metallic sites purposely formed on it. In such cases support by itself is another solid catalyst formed from metal supported on solid support. Illustrative supports belong to these category of supports are 5% Pd on carbon, 1% Ni on alumina copper-chromite calcined and reduced before use, ruthenium on silica, platinum sulfide on carbon, etc. In considering the individual factors, which dictate the choice of the support, it is realized that the final choice depends on the weighing of these factors in the context of the use to which catalyst are to be employed.

As evident, the rate of a catalytic reaction is dictated by the rate of the chemical reaction on the surface when observed activity is the function of the surface area of the solid support. In practice however overall rate of reaction is usually affected by mass or heat transfer, in which case porosity and geometry of the catalyst particle become increasingly important. As a result choice of support depends on the surface area of the catalyst that can be made available to the reactants and on the porosity of the catalyst.

In context of present invention, optimization of surface area is an important factor, which is related to other properties such as texture and the strength. Thus surface area and porosity are closely related, and it can be easily extrapolated further that porosity and mechanical strength is also interrelated. It is obvious to the designer to ensure long life for which catalyst needs a stable structure that is strongly bound together. Certainly this is not the case if porosity is too high. In case of supports of natural origin it is difficult to tailor degree of porosity in systematic fashion. Zeolites or carbon molecular sieves have most of their surface area within the channels, which due to their narrow width restrict passage of reactant molecules. Some gamma aluminas have pore size distribution in the range of 100–200 A°, while foamed aluminas have few micropores. Pore diameter can also be increased by careful precipitation of material in pore mouth.

Accordingly in addition to acting as a physical vehicle for the catalytic site support can have appreciable effect on the catalytic reaction it self, wheren for example local pH can be different or bulk of the support can stearically influence course of the reaction and even prevent its occurrence.

As discussed earlier it is understood that apart from chemical behavior of the active phases support plays important role in defining cartalyst properties. Such properties could be utilized depending on the process requirements. A considerable advantage would be gained if support effects on the active catalytic phases could be minimized which is often difficult in heterogeneous catalysts. By separating effects of active phases and support on can tailor the morphology of the catalyst by selecting support and active phases independent of each other.

Accordingly said support in the catalytic formulation is porous solid pores of which are predominantly of diameter greater than about 20 A° and have a pore diameter in the range of about 3–3000 A°. It is also preferred that support material be inert towards substrate, intermediates, products and solvent of the reaction unless concerted tandem sequence of reaction is desired of which one or more reactions is catalyzed by support itself. The suitable catalyst support is any solid that is insoluble in reaction medium and which is thermally stable and high melting solid. The support materials are exemplified but not limited by pumice, alumina-gel, silica gel, silica-alumina-gel, aged or deactivated silica-alumina cracking catalyst, magnesia, diatomaceous earth, bauxite, titania, zirconia, clays, both natural and acid treated, attapulgite, bentonite, diatomaceous earth, keisulghur, lime, calcium carbonate, calcium silicate, magnesium silicate, carborundum, activated and inactivated charcoal, adsorptive carbon, zeolites, zeolite molecular sieves, hydrotalcite, solid foams such as ceramic honeycombs, porous organic polymers such as macroreticular ion exchange resins, promeric polymers, porous crosslinked polystyrene-sulfonated, calcium alginate, barium sulfate, powdered cellulose, woven cotton mesh, foamed paper, functionalized polymers. It is also possible that the support may be a supported metal catalyst. Above said support materials may be used as regular and irregular particles, capillary tubes, meshes, fabric meshes and inter-spacing elements such as shapes, extrudates, ceramic rods, balls, broken pieces, raschig rings, tiles. Support materials can also have modifiers or deactivators present from impregnation or spraying processes, or other forming operations.

As described in the earlier embodiment present invention is concerned with solid phase multi-component formulation in which the catalytically active material is placed on the surface of the solid support. It is invented that soluble catalytic material such as organometallic complexes if rendered insoluble can form said catalytically active solid phases wherein active sites are defined isotropic molecular entities otherwise existing only in solution state. Such insoluble material when dispersed and supported on the surface of the solid support can form simple solid catalyst of the choice. In a support upon which catalytically active material is deposited, multiple or single reactants arrive to this catalytic material, which contains active sites whereupon reactants are transformed in to products and released back in to a bulk liquid.

Active components are composed of solid phase that is catalytically active i.e., which is primarily responsible for desired chemcial transformation. Unlike support generality of choice for such material is seldom available and composition must be rationally developed within the framework of laws of relevant chemistry. As it is well understood that diversity of materials can catalyze same reaction but one material may not necessarily catalyze diverse range of reactions. It is therefore another specific embodiment of the present invention whereby soluble moleculra catalyst are appropriately modified such that they can be incorporated in the said solid material The desired properties of such catalytically active solid material are, 1. Material should not be dissolved or withered in wide variety of reaction medium and conditions
2. Said material should have sufficient mechanical and fracture strength
3. Such material should be generated from organic organometallic building blocks
4. Material should have strong cohesive tendency towards support and total formulation should remain as composite material throughout reaction conditions such as temperatures from −78 to 300° C., in liquids comprising aqueous, organic and combination thereof as well as in acidic and alkaline conditions
5. Said material should be high melting and non subliming
6. Catalytically active solid material should be thermally stable should not pyrolyze at reaction temperatures
7. One of the building block of the material is molecular component responsible for particular reaction to be catalyzed.

The reaction media as said earlier is quite broad class of liquids and may be selected depending on solubility of substrates and other components as well as it should provide clean recovery of products. The liquids usable as reaction media are exemplified but not limited by petroleum fractions of different boiling ranges, cyclo alkanes such as cyclohexane, cycloheptane, cyclodecane, aromatics such as benzene, toluene, xylenes, ethyl benzene, butylbenzene, alcohols including methanol, ethanol, propanol, butanol, amyl alcohols (linear and branched) higher alcohols, cyclohexanol, phenol, xylinol, cresol, acids sucyh as acetic, propionic, butyric, amides such as formamide, dimethyl formamide, pyrolidone, n methyl pyrolidone, nitriles such as acetonitrile, propinitrile, benzonitrile, esters such as ethylacetate, methylacetate, methyl propionate, methyl benozate methyl propionate, ethers such as diethylether, dibutyl ether, diphenylether, tetrahydrofuran, dioxane, furan, ketones such as acetone, methylethylketone, pentane 2 one, cyclohexanone, nitroaliphatics such as nitromethane, nitroethane, nitropropane, nitroaromatics such as nitrobenzene, 2-nitrotoluene, halogenated solvents such as dichloromethane, chloroform, carbon tetra chloride, 1,2 dichloroethane, chlorobenzene, dichlorobenzene other high boiling solvents used for specific purpose include, hexadecane, octadecane, hexatracontane, squalene, chlorinated hydrocarbon oil, liquid paraffin, mineral oil, naphthalene, pheneanthrene, methyl naphthalene, high boiling substituted and non substituted organic alcohols, glycol, polyglycols, ethers, polyethers, such as glycerol, carbitol, dulcitol, erythritol, polyethyleneglycol, propyleneglycol, diglycerol, diethyleneglycol, polypropylene glycol, tetraethyleneglycol, 2-ethyl-1,3-hexanediol,1,5pentanediol, methoxypolyethylene glycol, diethylene glycolmonomethyl ether, polybutyleneglycol, 1,2,4-butanetriol, polyphenylether, methylbenzylether, bis(phenoxyphenyl) ether, tetraethylene glyco dimethylether, high boiling esters such as diisootylphthalate, dibutyl phthalate, dioctylphthalate, bis(2-ethylhexyl) phthalate, dinonyl phthalate, butyl benzyl phthalate, bis(2- tetrahydrofurfuryl) phthalate, dipropyl tetrachloro phthalate, dioctyl sebacate, bis(2- ethylhexyl)sebacate, inorganic solvents employable are water, room temperature ionic liquids, fluorous solvents and super critical dense phases. It is also possible that combination of one or more solvent media be used for reactions depending on solubility of reactants and products. The criteria for selection of solvent are chemical physical requirements of the reaction than the catalyst formulation components. The catalyst formulation as a whole is stable in diverse reaction media so practically any liquid can be used as solvent of the reaction as in case of conventional heterogeneous catalysts. Of course it is understood that for optimum performance of the catalyst very few liquids are suitable and must be selected accordingly.

Properties described earlier for catalytically active solid material are generally found in materials such as ceramics. It is well known in the art that ceramics contain metallic and non-metallic elements that are bonded ionically, covalently or both. These materials can be classified according to their structural composition of which $A_mX_n$ is most common example, A is polyvalent metal cation having +m charge and X is polyvalent anion having −n charge. These materials being ionic lack free electrons making them poor conductor of heat and electricity. Moreover ionic bonds being highly stable and directional also impart high melting range to ceramics. Usually ceramics are also more hard and resistant to physical and chemical changes. Other factors influencing the structure and property relationship of ceramic materials can be described as radium ratio and electronegativity difference between positive and negative ions although net negative charge on the material is nil. It was thus clearly envisaged that catalytic material should have properties similar to ceramic It is thus another embodiment of this work to develop a solid material wherein unit blocks are composed of defined catalytic entities. Another purpose of the present work is that development of a strategy without limiting said catalytic formulation to one particular class of complexes or reaction following certain mechanism according to some particular theory. It was conceived that materials of $A_mX_n$ type if formed where in $A_m$ is a alkaline earth metal cation and X being anion having structure responsible for catalyzing particular reaction then resultant material would have properties similar to ceramics. It was further speculated that such materials being ionic would not be soluble in organic solvent which are customarily used as solvents at the same time such materials due to their negligibly low solubility in aqueous solvents can be employed wherein media is aqueous.

In order to validate and universally substantiate this hypothesis severfal comparative experiments as referred in examples were undertaken. Anions having two or more negative charges were interacted with group IIA metal cations in solutions. Variety of group IIA compounds including salts, complexes, alkyls and hydrides were interacted with variety of anions having negative charge ranging from −1 to −3 and polyanionic compounds. Various group IIA compounds used for this were selected from magnesium chloride, magnesium acetate, magnesium nitrate, magnesium acac, magnesium complex of ethylene diamine tetraacetic acid disodium salt bytyl magnesium chloride, calcium hydroxide, calcium chloride, calcium nitrate, calcium hydride, calcium acac, calcium complex of ethylene diamine tetra acetic acid disodium salt, strontium acetate, strontium chloride, strontium acac, strontium complex of ethylene diamine tetra acetic acid disodium salt, barium nitrate, barium hydroxide, barium acetate, barium chloride. Such compounds were used as source for group IIA cations in solution. These cations were interacted with anions bearing −1, −2, −3 negative charge and polyanionic compounds. Such anions in solution were obtained from sodium nitrate, sodium propionate, ρ-toluene sulfonate sodium, m benzene disulfonate disodium, disodium oxalate, disodium sulfate, disodium phenyl phosphonate, disodium hydrogen phosphate, sodium hydrogen phthalate, ammonium molybdate, sodium carboxy methyl cellulose, sodium polyvinyl sulfonate. It was conclusively verified that "group IIA metail ions except magnesium ions form insoluble salts when interacted with anion having at least two or more neative charge. Such salts are insoluble in organic, mixture of aqueous organic and have extremely low solubility in water.

Accordingly the hypothesis is confirmed that alkali metal salts containing cation ($A^{n+}$ wherein n>1) when interacted with polyanions (X), provide a material that is insoluble in majority of solvents including organic as well as aqueous. Such proposition was validated by interacting variety of anionic compounds as described in experiment 1 based on diversity of anion structure it was realized that salts of alkaline earth metal and anion having 2 or more negative charges would provide a solid. Contemplative conclusions were drawn by systematically varying molecular volumes of the polyanions, electron density of the anionic functional groups and alkali metal cations. It was realized that sole requirement for material to form insoluble matter is that anion (X) as described earlier should have at least two anionically charged functional groups. From the experiments detailed subsequently it was realized that anions as small as oxalte to poly anions as large as polyvinyl sulfonate form sparingly to almost insoluble material in water and totally insoluble in organic solvents. If polyanionic nature is introduced on the peripheral positions of the catalyst molecules such that introduction of such groups does not interfer or affect catalytic reaciton, would provide anions (X) as said earlier.

Said anionic compounds are those which in conventional sense are acids with proton as counter cation. It is also preferred that strongly acidic functional groups be introduced on the native catalytically active species. Strongly acidic groups are preferred for the reason that these cannot be further protonated in contact with stronger acid that may exist in the reaction medium. It is therefore preferred that strongly acidic functional groups be selected such as for example —$SO_3^{1-}$, —$PO_3^{2-}$, etc though other groups are also suitable for example —$COO^-$ provided reaction medium is not acidic.

The catalytically active species described in earlier embodiment is a molecular entity having structural features necessary for intended catalysis. Such molecular entities for example are metal complex catalyst, metal oxoanions or ion pari. Peripheral positions of such catalytically active entities are substituted with anionic functional groups such as —$SO_3^{1-}$, —$PO_3^{2-}$, —$COO^-$ and degree of substition being essentially >1.

The substitution/modification as said herein is specifically meant molecular modification of the entity such that it bears said anionic functional groups such as for example —$COO^-$, —$SO_3^-$, —$PO_3^{2-}$. The term modification doesn't necessarily mean that modified entity is chemically derived from parent entity but it is the analogue of parent structure synthesized independently. It is further specified that such anionic functional groups be attached to one of the carbon atoms of the parent entity.

Thus the explicit statement of preferred embodiment is, said catalytic formulation is a combination of solid support as described in earlier embodiment having deposited thereon catalytically active solid material and ensemble as a whole exists as a stable composite solid in gas or liquid phases. The said liquid phases are comprised of aqueous, organic liquids or mixture thereof containing reactants, products and promoters. The catalytic fomulation of this embodiment as a physically stable composite solid in gas or liquid phases over a temperature range of −78 to 300° C. and remain as a physically stable composite solid in gas or liquid phases over pressure ranging from 5 to 5000 psi. The catalytically active materials of the embodiment are insoluble salts comprising of gorup IIA metal, catalytically active inert additive and catalytically active entities. To state further the group IIA metal exists as a cation having +2 charge. The group IIA metal cation of the said catalytically active material is selected from calcium, strontium and barium. And specifically excludes magnesium. The group IIA metal forming catalytically active material may be selected independently or in combination with other group IIA metals. The said catalytic material is formed by precipitation of polyanionic catalytically active entity and catalytically inactive polyanionic entity along with earlier stated group IIA metal ions.

The addition of inert additive is strongly reasoned for reducing solubility of catalytically active solid in aqueous solvent. As said material is ionic tends to dissociate in water and thereby dissolved in liquid phase if it is incidentallly liquid. In order to suppress this, other ionic material is required to be additionally present for sacrificial solubility and reduction of solubility by common ion effect, phenomenon that is well known in the literature. Additionally it is also envisaged that addition of such additive provides a microporosity to this material. Addition of catalytically inert material, which by itself is one of the components of the metal ligand complex, provides a surplus coordination capacity to the solid material which acts as significant buffer permitting retention of coordinated transition metal in the complex. Conversely, it implies that presence of additional ligand as catalytically active additive prevents the loss of transition metal as well. It is further understood that catalytically inert additive may be present optionally depending on adsorptivity of the support, fluid stresses on the solid particles and coordination tendency of the reactants and solvents. The catalytically active entity or entities can be independently selected from emtal complexes, quaternary compounds, metal oxo anions and polyoxometalletes or combination thereof.

The metal complexes as described earlier has a general formula

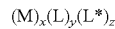

wherein M is catalytic metal atom or ion of corrdination complex is a transition metla from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VIII of periodic table of elements, the suffic x stands for number metal atoms or ions being present from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, aryloxy, cycloalkyl bearing at least one or more negative charged functional groups independently selected from $-SO_3^-, -SO_2^-, -PO_3^{2-}, -COO^-, -O^-, AsO_3^{2-}$ and $-S^-$; the suffix y is required to be at least one. L* is a radical selected from organic anion, inorganic anion and corrdinating compound containing at least one radical from O, N, S, Se, Te, P, As, Sb, Bi, Si, olefin, carbene, =C: having optionally attached thereto oxy, alkyl, aryl, arylalkyl, alkylaryl, alcoxy, aryloxy, cycloalkyl, hydrido, carbonyl, acyl and alkyl and Z is from 0 to 7

As described in earlier embodiment catalytically inert additive is optionally selected from ligand compounds wherein, ligand compounds contain at least one radical from O, N, S, Se, Te, P, As, Sb, Bi, Si, olefin, carbene having attached thereto oxy, alkyl, aryl, arylakyl, alkylaryl, alcoxy, aryloxy, cycloalkyl bearing at last one or more negatively charged functional groups independently selected from $-SO_3^-; -SO_2^- -PO_3^{2-}, -COO^-, -O^-, AsO_3^{2-}$ and $-S^-$ The quaternary compound of as described in one of the previous embodimetns has general formula $$[(Y^+)(R^*)_I][Z^-]$$

wherein, I=4 for $Y^+=N^+, P^+, As^+$ and I=3 for $Y^+=S^+$ and R* is selected independently from alkyl, aryl, arylalkyl, alkylaryl, alcoxy, aryloxy, cycloalkyl bearing at least one or more negatively charged functional groups independently selected from $-SO_3^-, -SO_2^- -PO_3^{2-}, -COO^-, -O^-, AsO_3^{2-}$ and $-S^-$ and Z is anion selected from organic anion, inorganic anion or coordination complex anion Such type of anionically charged ligands sulfonated tertiary phosphine metal salts ligands employable in this invention and/ or their methods for their manufacture are well known or obvious as seen e.g. by procedures described in "J. Chem. Soc.", pp. 276–288 (1958), U.S. Pat. Nos. 4,483,802 and 4,731,486 for instance such ligands can be prepared by sulfonating corresponding aromatic tertiary phosphine with fuming sulfuric acid under controlled temperature conditions to form predominantly protonated di or poly sulfonated phosphines, e.g.

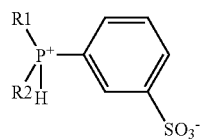

R1, R2 are aryl aryl alky or alkyl

For example the solid phosphine is added to fuming sulfuric acid in portions while controlling temperature below 5° C. and then heated, e.g. to 20–80° C. until desired degree of sulfonation is achieved. The reaction mixture is then cooled immediately to stop any further sulfonation or oxidation of phosphine and without waiting water is added to this avoiding temperature raising above 30° C. and said protonated phosphine salit is neutralized with alkali solution. The mixture containing alkali sulfonate and alkali sulfate is concentrated by evaporating water. During the evaporation of water alkali sulfate precipitate, which is removed by filtration and methanol, was mixed to this mother liquor. Most of the alkali sulfate precipitate and sulfonated phosphine is extracted in the methanol. Evaporation of methanol affords sulfonated phosphine as solid. Dissolving in suitable solvent such as water or ethanol and recrystallizing it therefrom may further purify the crude tertiary phosphine metal sulfonate.

The sulfonation can also be carried out in concentrated sulfuric acid media using boric acid and sulfur trioxide complex as described by Albanese et al U.S. Pat. No. 5,684,181 and U.S. Pat. No. 5,780,674. The advantage of such procedure is that it reduces phosphine oxide formation. Similarly work up of the sulfonation reaction may also be modified by extracting quenched sulfonation mixture by tributyl phosphite or tri iso octyl amine organic phase which is subsequently extracted with alkali solution advantage of such procedures being phosphines can be selectively separated from corresponding oxides. Oxides of phosphines are frequent contaminants in such sulfonated phosphine ligands. Presence of phosphine oxide as such doesn't affect catalytic behavior of the ligand in combination with transition metal. It is understood that such phosphine oxides don't coordinate with metal so contamination due to phosphine oxide may be tolerated for the purpose of catalyzing reactions. The presence of phosphine oxides may be intolerant in cases such as bidentate ligands and bidentate chiral ligands. Those experts in the field since can easily realize the situation since phosphine mono oxide of the bidentate ligand will display different coordination behavior. The situation is further complicated while preparing catalysts for enantio selective reactions. In such case phosphine oxide removal is desired and may be achieved by extractive separation from tributyl phosphite or tri iso octylamine solutions or by fractionating from gels of modified dextran such as SEPHADES G15 (TM) as described by Hermann et al Agnew. Chem. Int. Eng. Ed. 29 (1990) No (4) 391–393.

Such ligands that are sulfonated can be prepared by various methods employing lithium phosphides. Grignard reagent and phosphorus trichloride etc. Knowledge and understanding of such ligands is taught in literature known to artisan skilled in the art. For example Kosolapoft G. M., Maier L. Organic Phosphorus Comounds, Volume 1, 288, Wiley Interscience, New York © 1972./Engl R. synthesis of carbon phsophorus bonds, © CRC Press 1988./ Triplett S. A. A specialist Periodical Report of Organophosphorus Chemistry, Chemcial Society London © 1970/ specific example of such synthesis is expalined in (Mann, F. G. et al, J. Chem. Soc. 1937, 527–535; U.S. Pat. No. 4,483,802 and U.S. Pat. No. 4,731,486) Similarly nitrogen containing ligands can be prepared by specific chemical synthesis known in the art (Eit Drent, U.S. Pat. No. 5,166,411). Synthesis, manufacture and purification of such ligands is clearly out of purview of this application. It is clearly understood knowledge concerning sulfonation of such ligands is also well known. Similarly ligands bearing other anionically charged functional groups for example $-COO^-$, $-PO3^{2-}$ can also be prepared by sequence of specific organic synthesis (synthesis of phosphonic and carboxylic containing ligands). This invention claims further utilization of such well known ligands for preparation of generic catalyst formulation which is a solid and employed as a catalyst. This utilization of such known ligands by further processing is within the scope and purview of this application and is one of the preferred embodiments of this invention. Illustrative preferred anionic ligands and their transition metal complexes and quaternary compounds include, as follows. It is implicit that these are only illustrative and not comprehensive

| Anionic ligand |
| --- |

-continued
| Anionic ligand |
|---|
| 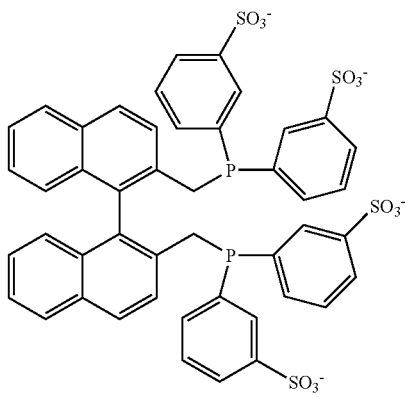 |
| 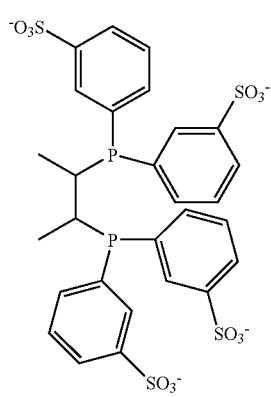 |
| 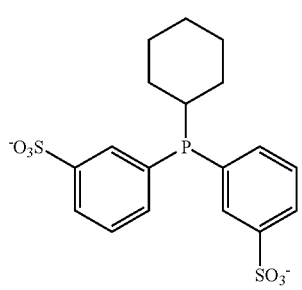 |
| 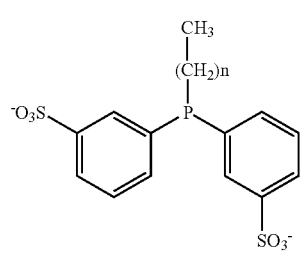 |
-continued
| Anionic ligand |
|---|
| 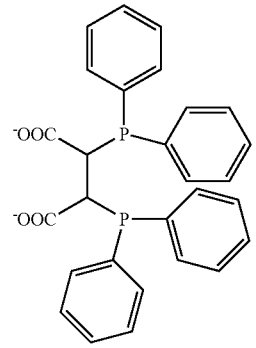 |
| 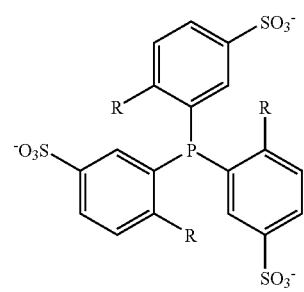 |
| 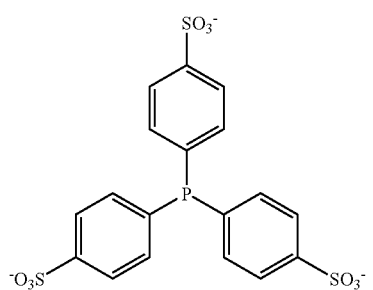 |
| 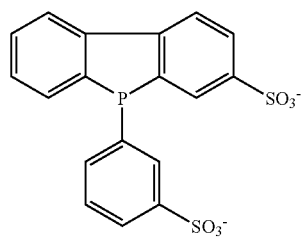 |
| 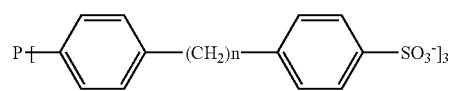 |

| Anionic ligand | Anionic ligand |
|---|---|
| 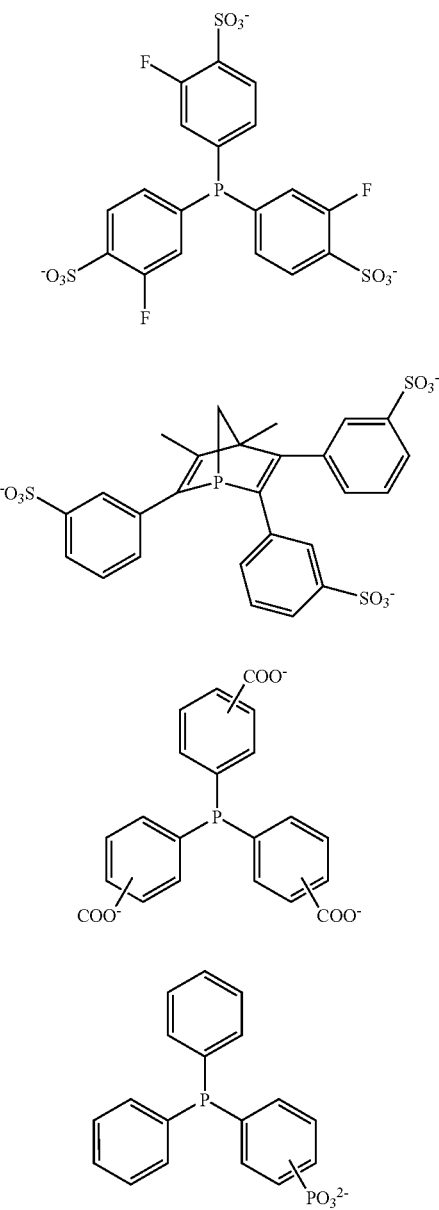 | 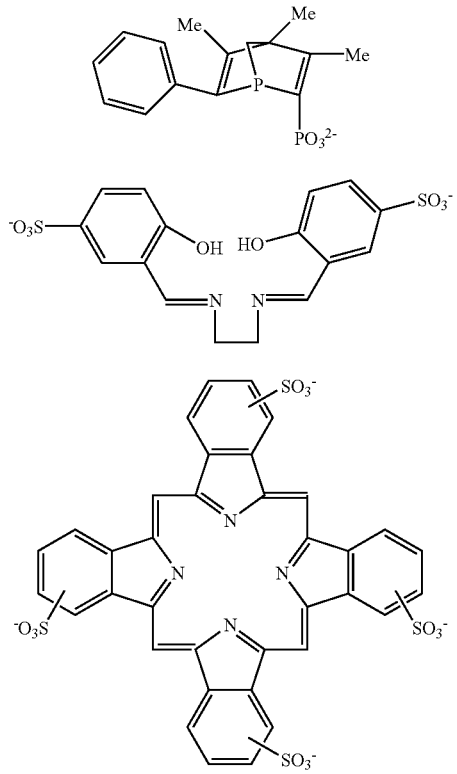 |
Some of the illustrative quaternary compounds are
| Anionic quaternary compounds |
|---|
| 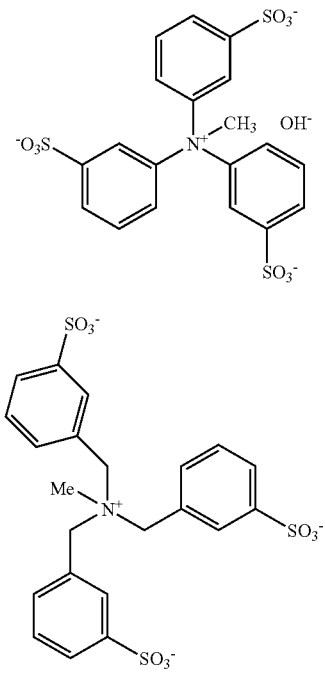 |

-continued

| Anionic quaternary compounds |
|---|

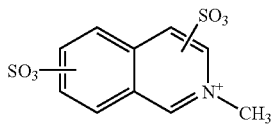

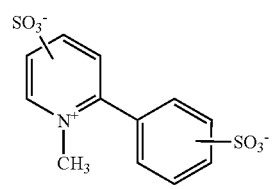

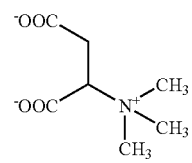

Poly anionic ligands and quaternary compounds as described above exist as salts of alkali metal, quaternary ammonium or proton. It is well known in the art that such compounds are water soluble combination of such ligands with transition metals provide access to their complexes. Some of illustrative catalytically active entities are:

| Catalytically active anionic entity |
|---|

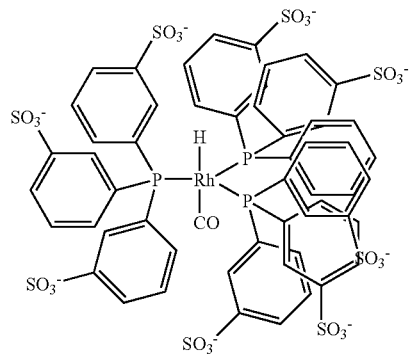

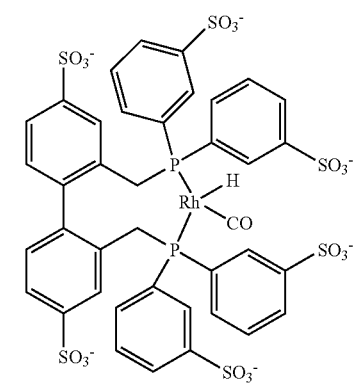

| Catalytically active anionic entity |
|---|

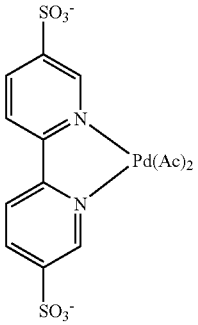

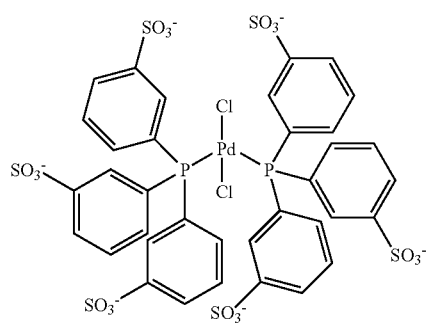

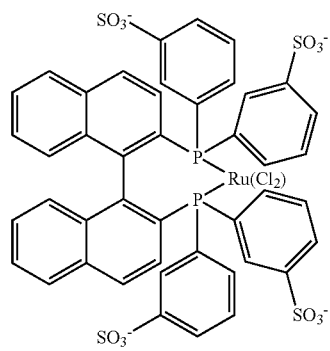

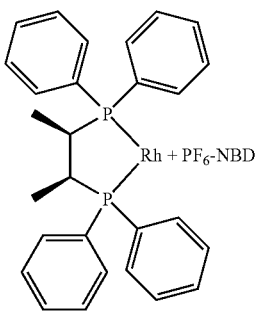

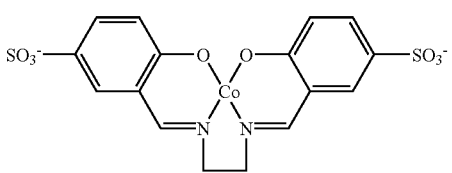

-continued

| Catalytically active anionic entity |
|---|

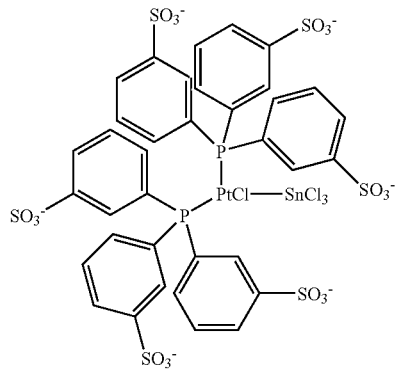

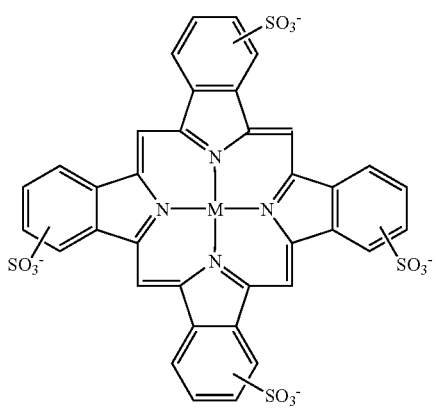

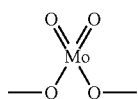

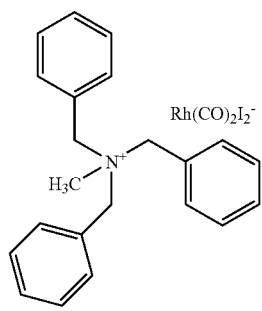

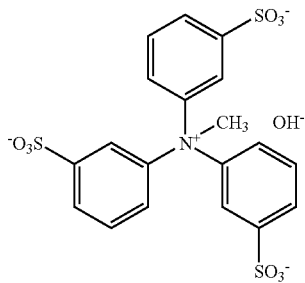

Complexes as said earlier can be prepared by various methods known in literature descriptions. Broadly such metal complexes can be classified as follows:
1. Synthesis of metal complexes from metal salts and anionic ligands
2. Displacement of a labile ligand by anionic ligand For example complexes such as $PdCl_2$ bis (triphenyl phosphine trisulfonate trisodium) is prepared by reacting $PdCl_4^{2-}$ with triphenyl triphenyl phosphine trisulfonate trisodium in aqueous ethanol, ruthenium chloride with triphenyl triphenyl phosphine trisulfonate trisodium, where as complexes such as $HRhCO(TPPTS)_3$, $RuCl_2BINAP$, are prepared by displacement of labile ligands such as cyclooctadiene or acetylacetonate. Complexes such as sulfonated pthalocynine are prepared by simultaneous formation of ligand and complex. As said earlier synthesis of such complexes is a well-known knowledge to those experts in the art. The synthesis of such complexes is beyond the scope and purview of this invention. Yet utilization of such complexes to form insoluble solid formulation for catalytic application is the explicit embodiment of this invention. Several different metal complexes containing different metals and diversity of ligands were synthesized. Such metal complexes whenever interacted with group IIA metal compounds except magnesium compounds provided solids, which were insoluble in water, organic solvents. The precipitates were solids up to 200° C. and were non-subliming. Several experiments as described in examples were carried out to verify proposed hypothesis to deduce a logical conclusion that when poly-anions when interacted with a group IIA metal, form a precipitate that is insoluble in variety of liquids. It is yet another preferred embodiment of this application that the admixture of catalytifcally active poly anion and catalytically inactive anion is preferred to form a precipitate that is insoluble in majority of liquids. Additional presence of catalytically inactive additive is reasoned to reduce solubility of precipitated complex in water by well-known phenomena of common ion effect. It is alos preferred to add additional ligand that is used to form complex. The presence of additional ligand is preferred especially in cases where catalytic formulation is intended to be used in liquid phases that are coordinating or ligand involved is monodentate.

The catalytically active material of the said catalyst formulation is formed from interaction of solution of catalytically inactive additive, catalytically active entity and a solution of group IIA metal cation by precipitation. The solution of catalytically inactive additive, catalytically active entity when contacted with a solution of group IIA metal cation, two solution start diffusing and subsequently whenever cation of group IIA metal encounters collision with poly anion solidification is initiated and cluster of solid is slowly formed. Such precipitation wherein, catalytically inactive additive is independently selected from anions having at least two or more negative charges, ligand compounds containing at least one radical from O, N, S, Se, Te, P, As, Sb, Bi, Si, olefin, having attached thereto oxy, alkyl, aryl, arylalkyl, alkylaryl, alcoxy, aryloxy, cycloalkyl bearing at least one or more negatively charged functional groups independently selected from $—SO_3^-$, $SO_2^-$—$PO_3^{2-}$, $—COO^-$, $—O^-$, $AsO_3^{2-}$ and $—S^-$, and combination thereof and catalytically active entity is independently selected from metal complexes, quaternary compounds, metal oxo anions and polyoxometallates or combinations thereof The catalytically active may be selected such that metal complexes has a general formula

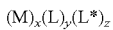

wherein M is catalytic metal atom or ion of coordination complex is a transition metal from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VII of periodic table of elements, x is from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, aryloxy, cycloalkyl bearing at least one or more negatively charged functional groups independently selected from $-SO_3^-$, $-SO_2^-$ $-PO_3^{2-}$, $-COO^-$, $-O^-$, $AsO_3^{2-}$ and $-S^-$, y is at least 1, L* is a radical selected from organic anion, inorganic anion and coordinating compound containing at least one radical from O, N, S, Se, Te, P, As, Sb, Bi, Si, olefin, carbine, =C: having attached thereto oxy, alkyl, aryl, arylalkyl, alkylaryl, alcoxy, arlyoxy, cycloalkyl, z is from 3 to 7 and quaternary ammonium compound has a general formual

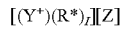

wherein, I=4 for $Y^+=N^+$, $P^+$, $As^+$ I=3 for $Y^+=S^+$ and R* is selected independently from alkyl, aryl, arylalkyl, alkylaryl, alcoxy, arlyoxy, cycloalkyl bearing at least one or more negatively charged functional groups independently selected from $-SO_3^-$, $-SO_2^-$, $-PO_3^{2-}$, $-COO^-$, $-O^-$, $AsO_3^{2-}$ and $-S^-$ and Z is anion selected from organic anion, inorganic anion or coordination complex anion.

Accordingly as described in earlier embodiment inventors have developed a common technique for solidification of pluralistic catalytic entities, functioning according to different theories and mechanisms. Such solidification is selected by incorporating earlier said catalytic entities in ionic solid, which by itself is formed by interaction of poly anionic catalytic entity, polyanionic additive and group IIA metal ion.

The catalytic formulation of this invention wherein earlier said catalytic material is supported on the surface of solid support. It is recalled that formed catalytic material being insoluble cannot be dissolved in liquid and then supported on the solid support accordingly technique was required to form such material directly on the surface of the solid support by precipitation.

The final formation of composite catalyst can thus be carried out by precipitation of catalytically active material on the support surface. The formation of catalyst by precipiation or co-precipitation is thus centrally important in this respect. However precipitation is a complex phenomenon and demand several ancillary techniques to be developed in order to deposit catalyst on the support surface. Nevertheless, for several catalytically relevant materials especially for support materials precipitation is most frequently applied method. In this respect such precipitation is troublesome as it may generate clusters and particles in the bulk of liquid. Dealing specifically formation of solid catalytically active material is better described by term co precipitation as two components categorized as group IIA metal ion and poly anionic entity when interacted yields a precipitate. Co-precipitation is extremely suitable technique for generation of uniform distribution of such material on the support material, as stoichiometry of interacting species is definite. Form earlier experiences it is known fact that co-precipitation can provide good dispersion of the support surface which is otherwise difficult to achieve catalyst assembly that is under consideration. Thus the bulk co-precipitation process needs to be modified to achieve assembly of composite catalyst system.

Preferably, the co precipitation is carried out in such a manner that precursor solutions containing anionic entities (catalytically active entity and catalytically inert additive) and group IIA salt solutions diffuse near the surface of the support or the formation of insoluble clusters initiate near the surface of the support. Hereinafter solution containing anionic component is designated as solution. A and solution containing group IIA metal is designated as solution B. It is another embodiment of the present invention that outlines various methods for assembling catalytic formulation of earlier said embodiments. These assembly techniques are broadly classified according to various techniques of precipitation and are described in ensuing description of embodiments.

One of the process for the preparation of a heterogeneous catalytic formulation as a solid composite comprising of porous solid support having deposited thereon a catalytically active solid is characterized by suspending insoluble solid support in a liquid phase to which a solution of catalytically inert additive and catalytically active entity and a solution of group IIA metal cation are added simultaneously or sequentially with vigorous agitation and allowed to age for 1 to 48 hours wherein, support is a mechanically robust and thermally stable solid in reaction media, having a mean pore diameter in the range of about 3–3000 A° and existing as powder, granules, flakes or pallets or regular or irregular shapes, sheets, monolith, ropes and woven fabric of fibrous solids and catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^-$$-PO_3^{2-}$, $-COO^-$, $-O^-$, $AsO_3^{2-}$ and $-S^-$.

The catalytically active entity is independently selected from metal complexes, quaternary compounds, metal oxo anions and polyoxometallates or combinations thereof such that metal complexes having a general formula

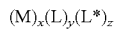

wherein M is catalytic metal atom or ion of coordination complex is transition metal from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VII of periodic table of elements, x is from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^-$$-PO_3^{2-}$, $-COO^-$, $-O^-$, $AsO_3^{2-}$ and $-S^-$ and y is at least 1 and L* is a radical selected from organic anion, inorganic anion and corrdinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl, z is from 0 to 7 and the quaternary ammonium compound has a general formula

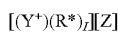

wherein, I=4 for Y⁺=N⁺,P⁺,As⁺, I=3 for Y⁺=S⁺ and R* is selected independently from alkyl, aryl, arylalkyl, alkylaryl, alcoxy, arlyoxy, cycloalkyl bearing at least one or more negatively charged functional groups independently selected from —SO₃⁻,—SO₂⁻ —PO₃²⁻, —COO⁻,—O⁻, AsO₃²⁻ and —S⁻ and Z is anion selected from organic anion, inorganic anion or coordination complex anion. The group IIA metal cation is selected from compounds of Ca²⁺, Sr²⁺ and Ba²⁺.

The above said process is carried out in the temperature ranging from −78 to 20° C. preferably between −5 to 100° C. The solvent for the process is selected from aqueous, water miscible organic or mixture thereof.

The process as described above wherein solution of catalytically inert additive and catalytically active entity and a solution of group IIA metal cation are added simultaneously over a period of 10 to 1500 min. After completion of this treatment the catalyst is recovered by centrifugation, decantation, gravity settling or other techniques of solid liquid separation and dried subsequently in vacuum. The method as described herein is employable when components of precipitate slowly produce solid material under the influence of viscosity, solvent media and solubility modifiers. As seeds of solid material develop slowly and there is enough time for seeds of the precipitate to settle on the support surface. Other methods described herein after are suitable for co-precipitation that occurs instantaneously. Such methods are usually critical due to specialized unit operation required for them and also require specific equipment for the manufacture.

Another process for the preparation of a heterogeneous catalytic formulation as a solid composite comprising of porous solid support having deposited thereon a catalytically active solid is characterized by impregnating the solid support with catalytically active entity and catalytically inert additive followed by drying, dried support having deposited thereon catalytically active entity and catalytically inert additive is added to a solution of group IIA metal compound, with simultaneous agitation. The suspension is aged for 1 to 48 hours with agitation, the process is accordingly carried out in the temperature ranging from −78 to 200° C. preferably between −5 to 100° C.

The support in this case is a mechanically robust and thermally stable solid in reaction media, having a mean pore diameter in the range of about 3–3000 A⁰ and existing as powder, granules, flakes or pallets of regular or irregular shapes, sheets, monolith, ropes and woven fabric of fibrous solids and catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO₃⁻, —SO₂⁻—PO₃²⁻, —COO⁻, —O⁻, AsO₃²⁻ and —S⁻

The catalytically active entity is independently selected from metal complexes, quaternary compounds, metal oxo anions and polyoxometallates or combinations thereof such that metal complexes having a general formula

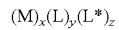

wherein M is catalytic metal atom or ion of coordination complex is a transition metal from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VIII of periodic table of elements, x is from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO₃⁻, —SO₂⁻—PO₃²⁻, —COO⁻, —O⁻, AsO₃²⁻ and —S⁻ and y is at least 1 and L* is a radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl, z is from 0 to 7 and quaternary ammonium compound has a general formula

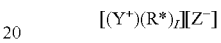

wherein, I=4 for Y⁺=N⁺, P⁺, As⁺; I=3 for Y⁺=S⁺ and R* is selected independently from alkyl, aryl, arylalkyl, alkylaryl, alcoxy, arlyoxy, cycloalkyl bearing at least one or more negatively charged functional groups independently selected from —SO₃⁻, —SO₂⁻, —PO₃²⁻, —COO⁻, —O⁻, AsO₃²⁻ and —S⁻ and Z is anion selected from organic anion, inorganic anion or coordination complex anion. The group IIA metal cation is selected from compounds Ca²⁺, Sr²⁺ and Ba²⁺. According to process under consideration solvents used to dissolve anionic components and group IIA metal cations are aqueous, water miscible organic or mixture thereof The process modification may be adopted wherein support having deposited thereon catalytically active entity and catalytically inert additive is added to a solution of group IIA metal compound, with simultaneous agitation over a period of 10 to 1500 min, depending upon specific process requirements. The process accordingly concludes by recovering catalyst by centrifugation, decantation, gravity settling or other techniques of solid liquid separation and drying subsequently in vacuum Yet according to another preferred process for the preparation of a heterogeneous catalytic formulation as a solid composite comprising of porous solid support having deposited thereon a catalytically active solid is characterized by impregnation of support with a solution of catalytically inactive additive and catalytically active entity followed by drying. Solid support having deposited thereon catalytically inactive additive and catalytically active entity is suspended in water immiscible solvent to which a solution of group IIA metal compound is added with vigorous agitation and concurrent removal of low boiling or azeotropic fraction of a solvent. Suspension is allowed to age for 1 to 48 hours, wherein the process is accordingly carried out in the temperature ranging from 70 to 200° C.

The support in this case is a mechanically robust and thermally stable solid in reaction media, having a mean pore diameter in the range of about 3–3000 A⁰ and existing as powder, granules, flakes or pallets of regular or irregular shapes, sheets, monolith, ropes and woven fabric of fibrous solids and catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO$_3^-$, —SO$_2^-$—PO$_3^{2-}$, —COO$^-$, —O$^-$, AsO$_3^{2-}$ and —S$^-$ The catalytically active entity is independently selected from metal complexes, quaternary compounds, metal oxo anions and polyoxometallates or combinations thereof such that metal complexes having a general formula

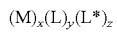

wherein M is catalytic metal atom or ion of coordination complex selected from a transition metal groups IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex contains metal atom or ion from group VIII of periodic table of elements, x is ranging from 1 to 60, L is selected from aliphatic, aromatic and heterocyclic compounds containing at least one radical from O, N, S, Si, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO$_3^-$, —SO$_2^-$—PO$_3^{2-}$, —COO$^-$, —O$^-$, AsO$_3^{2-}$ and —S$^-$ and y is at least 1 and L* is a radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl, z is from 0 to 7 and the quaternary ammonium compound has a general formula

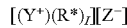

wherein, I=4 for Y$^+$=N$^+$, P$^+$, As$^+$, I=3 for Y$^+$=S$^+$ and R* is selected independently from alkyl, aryl, arylalkyl, alkylaryl, alcoxy, arlyoxy, cycloalkyl bearing at least one or more negatively charged functional groups independently selected from —SO$_3^-$, —SO$_2^-$, —PO$_3^{2-}$, —COO$^-$, —O$^-$, AsO$_3^{2-}$ and —S$^-$ and Z is anion selected from organic anion, inorganic anion or coordination complex anion. The group IIA metal cation is selected from compounds of Ca$^{2+}$, Sr$^{2+}$ and Ba$^{2+}$.

The solvents employed to form a solution of group IIA metal ion are aqueous, water miscible organic or mixture thereof and solvent employed to suspend support is water immiscible organic solvent having boiling point in the range 40 to 200° C., the present process is concludes by recovering catalyst by centrifugation, decantation, gravity settling or other techniques of solid liquid separation and dried subsequently in vacuum Process for the preparation of a heterogeneous catalytic formulation as a solid composite comprising of porous solid support having deposited thereon a group IIA metal compound followed by drying. Solid support having deposited thereon group IIA metal is suspended in water immiscible solvent to which a solution of catalytically active entity and catalytically inactive additive is added with vigorous agitation and concurrent removal of low boiling or azeotropic fraction of solvent. The process of azeotropic distillation is accordingly carried out in the temperature ranging from 70 to 200° C. The liquid medium employed for the process of azeotropic removal of solvent is water immiscible organic solvent having boiling point in the range 40 to 200° C. There after suspension is allowed to age for 1 to 48 hours.

The support in this case is a mechanically robust and thermally stable solid in reaction media, having a pore diameter in the range of about 3–3000 A$^0$ and existing as powder, granules, flakes or pallets of regular or irregular shapes, sheets, monolith, ropes and woven fabric of fibrous solids and catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO$_3^-$, —SO$_2^-$—PO$_3^{2-}$, —COO$^-$, —O$^-$, AsO$_3^{2-}$ and —S$^-$ The catalytically active entity is independently selected from metal complexes, quaternary compounds, metal oxo anions and polyoxometallates or combinations thereof such that metal complexes having a general formula

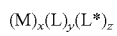

wherein M is catalytic metal atom or ion of coordination complex selected from transition metal group IIIB, IVB, VB, VIB, VIIB, IB or IIB of the periodic table of elements and is selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VIII of periodic table of elements, x is from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from —SO$_3^-$, —SO$_2^-$—PO$_3^{2-}$, —COO$^-$, —O$^-$, AsO$_3^{2-}$ and —S$^-$ and y is at least 1 and L* is a radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl, z is from 0 to 7 and the quaternary ammonium compound has a general formula

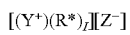

wherein, I=4 for Y$^+$=N$^+$, P$^+$, As$^+$; I=3 for Y$^+$=S$^+$ and R* is selected independently from alkyl, aryl, arylalkyl, alkylaryl, alcoxy, arlyoxy, cycloalkyl bearing at least one or more negatively charged functional groups independently selected from —SO$_3^-$, —SO$_2^-$, —PO$_3^{2-}$, —COO$^-$, —O$^-$, AsO$_3^{2-}$ and —S$^-$ and Z is anion selected from organic anion, inorganic anion or coordination complex anion. The group IIA metal cation is selected from compounds of Ca$^{2+}$, Sr$^{2+}$ and Ba$^{2+}$. And solvent employed to form a solution of group IIA metal ion is aqueous, water miscible organic or mixture thereof. After removal of organic immiscible and low boiling liquids, centrifugation, decantation, gravity settling or other techniques of solid liquid separation and dried subsequently in vacuum to recover the catalyst Process for the preparation of a heterogeneous catalytic formulation as a solid composite comprising of fluidizing solid support in the current of gasses. Solution of catalytically active entity and catalytically inert additive is sprayed in such a way that catalytically active entity and catalytically inert additive is deposited on the solid support the fluidization of solid is continued for 1 to 48 hours. Solution of group IIA metal compound is subsequently sprayed and fluidization of solid is further continued for 1 to 48 hours and solids are recovered. The process of fluidization is carried out in the temperature ranging from 20 to 200° C., wherein the support in this case is a mechanically robust and thermally stable solid in reaction media, having a mean pore diameter in the range of about 3–3000 A° and existing as powder, granules, flakes or pallets of regular or irregular shapes, sheets, monolith, ropes and woven fabric of fibrous solids and catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^--PO_3^{2-}$, $-COO^-$, $-O^-$, $AsO_3^{2-}$ and $-S^-$ the catalytically active entity is independently selected from metal complexes, quaternary compounds, metal oxo anions and polyoxometallates or combinations thereof such that metal complexes has a general formula

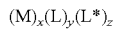

$$(M)_x(L)_y(L^*)_z$$

wherein M is catalytic metal atom or ion of coordination complex is a transition metal from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VIII of periodic table of elements, x is from 1 to 60, L is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^--PO_3^{2-}$, $-COO^-$, $-O^-$, $AsO_3^{2-}$ and $-S^-$ and y is at least 1 and $L^*$ is radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl, z is from 0 to 7 and quaternary ammonium compound has a general formula

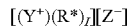

$$[(Y^+)(R^*)_I][Z^-]$$

wherein, I=4 for $Y^+=N^+$, $P^+$, $As^+$, I=3 for $Y^+=S^+$ and $R^*$ is selected independently from alkyl, aryl, arylalkyl, alkylaryl, alcoxy, arlyoxy, cycloalkyl bearing at least one or more negatively charged functional groups independently selected from $-SO_3^-$, $-SO_2^--PO_3^{2-}$, $-COO^-$, $-O^-$, $AsO_3^{2-}$ and $-S^-$ and Z is anion selected from organic anion, inorganic anion or coordination complex anion. The group IIA metal cation is selected from compounds of $Ca^{2+}$, $Sr^{2+}$ and $Ba^{2+}$. The solvent employed to form a solution of group IIA metal ion is aqueous, water miscible organic or mixture thereof.

This invention further extends another preferred method for making catalysts according to present invention. According to this method an anionically charged entity and anionically charged additive are deposited on the solid support and are subsequently cured by spraying group IIA metal salt solution with simultaneous removal of solvent.

Figure 5:
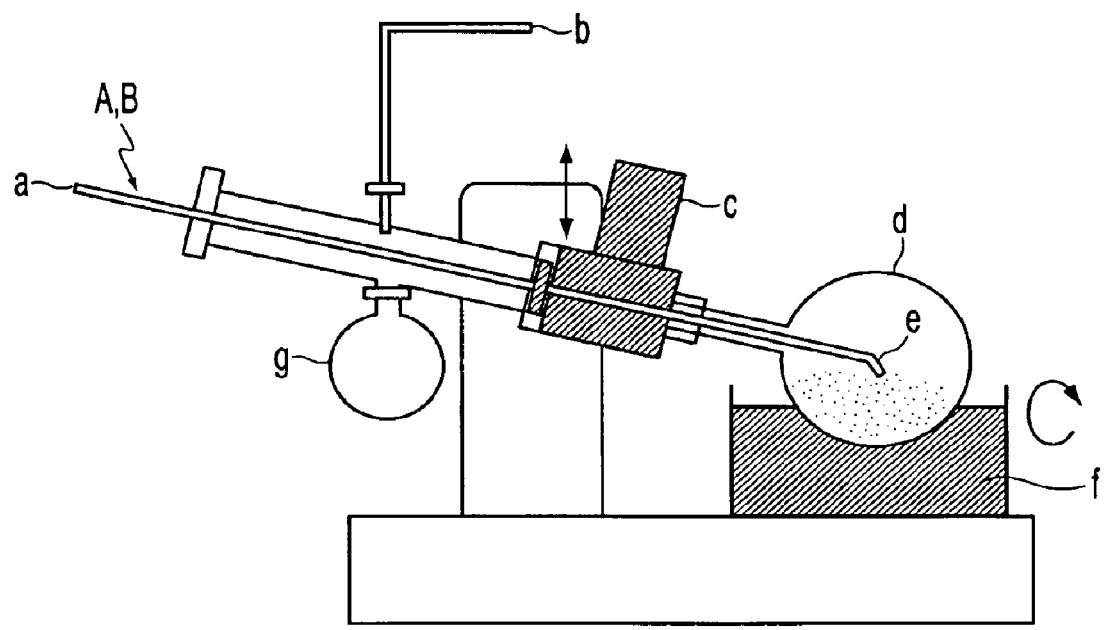
FIG. 5 is the schematic of the catalyst preparation unit wherein, a is the inlet for solution A and B, b is the vacuum line, c motor for coating pan, d is the coating pan, e is the nozzle for liquids A and B, f is the high temperature bath, g is the collection vessel for condensed liquid

Accordingly, process for the preparation of a heterogeneous catalytic formulation as a solid composite comprises of tumbling solid support in the rotating pan under current of inert gasses. Solution of catalytically active entity and catalytically inert additive is sprayed in such a way that catalytically active entity and catalytically inert additive is uniformly deposited on the solid support the tumbling of solid is continued for 1 to 48 hours. Solution of group IIA metal compound is subsequently sprayed and tumbling of wet solid is further continued for 1 to 48 hours and solids are recovered. The process described accordingly is carried out in the temperature ranging from 20 to 200° C. Either heating the inert gas stream or rotating pan, which contains support, may achieve the process temperature. The laboratory apparatus employed to form present formulation is represented in FIG. 5 and such apparatus may be suitably scaled depending upon volume requirements.

The support material employable herein is a mechanically robust and thermally stable solid in reaction media, having a mean pore diameter in the range of about 3–3000 A° and existing as powder, granules, flakes or pallets of regular or irregular shapes, sheets, monolith, ropes and woven fabric of fibrous solids.

The catalytically inactive additive is independently selected from anions having at least two or more negative charges which may be organic, inorganic, or a compound containing at least one radical form O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^--PO_3^{2-}$, $-COO^-$, $-O^-$, $AsO_3^{2-}$ and $-S^-$. Additionally this catalytically inactive additive may be polymer bearing multiple anionic charges.

Catalytically active entity is independently selected from metal complexes, quaternary compounds, metal oxo anions and polyoxometallates or combinations thereof The metal complex entity that is catalytically active can be selected such that metal complexes have a general formula

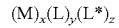

$$(M)_x(L)_y(L^*)_z$$

wherein M is catalytic metal atom or ion of coordination complex is a transition metal from group IIIB, IVB, VB, VIB, VIIB, IB or IIB of the periodic table of elements and may be selected independently suitable transition metal ions and atoms include Sc, Y, Ti, Zr, Hf, V, Cr, Mo, W, Mn, Re, Fe, Ru, Os, Co, Rh, Ir, Ni, Pd, Pt, Cu, Ag, Au, Zn. Preferably the metal complex will contain metal atom or ion from group VIII of periodic table of element. The suffix x indicates number of such catalytic transition metal present in the complex. The number of such metal entities ranges from 1 to 60. The component L of the metal complex is aliphatic, aromatic and heterocyclic compounds containing at least one radical from O, N, S, Se, Te, P, As, Sb, Bi, Si, olefin, carbene having attached thereto oxy, alkyl, aryl, arylalkyl, alkylaryl, alcoxy, arlyoxy, cycloalkyl bearing at least one or more negatively charged functional groups independently selected from $-SO_3^-$, $-SO_2^--PO_3^{2-}$, $-COO^-$, $-O^-$, $AsO_3^{2-}$ and $-S^-$. The suffix y indicate the number of coordinating ligands that hold metal in the lower oxidation state and it is necessary that y is at least 1. $L^*$ is a radical selected from organic anion, inorganic anion and coordinating compound containing at least one radical from O, N, S, Se, Te, P, As, Sb, Bi, Si, olefin, carbene, =C: having attached thereto oxy, alkyl, aryl, arylalkyl, alkylaryl, alcoxy, arlyoxy, cycloalkyl. Suffix z indicates number of such non-participating ligands. These ligands may be identical if present in multiple or different but total number ranges from 0 to 7. Alternatively another class of catalytically active entity, which is employable alone or in combination with above said transition metal complex, is quaternary compound which, has a general formula

[(Y⁺)(R*)$_I$][Z⁻]

wherein, compounds that are elected can belong to quaternized compounds of nitrogen phosphorus, arsenic and sulfur. Instances when quaternary compound belongs to nitrogen, phosphorus, arsenic containing compounds suffix I=4 for Y⁺=N⁺, P⁺, and for sulfur compounds I=3 for Y⁺=S⁺ R* is selected independently from alkyl, aryl, arylalkyl, alkylaryl, alcoxy, arlyoxy, cycloalkyl bearing at least one or more negatively charged functional groups independently selected from —SO$_3$⁻, —SO$_2$⁻, —PO$_3$²⁻, —COO⁻, —O⁻, AsO$_3$²⁻ and —S⁻, Z is anion selected from organic anion, inorganic anion or coordination complex anion. In majority cases it is implicit that actual catalytic entity is anion Z⁻ Quaternary compound provides an anchor for solidification as well as for providing required electrostatic field such that anion z- does not get away The group IIA metal cation is selected from compounds of Ca²⁺, Sr²⁺ and Ba²⁺. The process for formation of catalyst in coating pan as described earlier wherein the solvent employed to form solutions is preferably aqueous, water miscible organic or mixture thereof. Such solutions according to the process are sprayed simultaneously or sequentially.

Irrespective of the processes employed to form catalytic formulation said solid catalytic ensemble could be employed to catalyze diversity of reactions in gas phase or in liquid slurry. The catalyst being robust solid provides an opportunity to select suitable reactor configuration for manufacture of organic compounds in variety of reactor configurations such as fixed bed, trickle bed, fluidized bed and slurry reactors depending on the physical state and properties of reactants and products.

The solid catalyst of the present invention can be optionally modified wherein a film of high boiling liquid or low melting solid is optionally deposited on the solid catalyst. This modification can be adopted to enhance local solubility of reactants or modify environment of the catalytic sites to obtain high selectivity for required products.

The catalyst to be formulated according to earlier described embodiments for particular reaction is selected from analogous catalysts that catalyze such reaction in liquid phase; analogues entity is derived from such parent catalyst of homogeneous system by appropriate functionalization so as to introduce negative charges on it. Catalytically active entity is independently derived from metal complexes, quaternary compounds, metal oxo anions and polyoxometallates or combinations thereof depending upon requirement. Except anionic functional groups rest structure of catalytic entity in immaterial for solidification of such entity. Some of illustrative derivations of anionically charged entities from respective soluble catalysts are displayed in following table. Reaction classes represented are exemplary only and catalytic entities are within the purview of appended claims. It is thus explicit clarification of the embodiment that solid catalyst formulation is described wherein the catalytic entities are solidified by generic technique irrespective of reaction they catalyze. Such catalytic entities are clearly claimed in claims.

Some of the illustrative examples of anionically functionalized soluble catalytic entities and their applications are listed in following table.

| Reaction type | Soluble catalyst | Analogous anionic entity |
|---|---|---|
| Hydro-formylation | HRhCO(TPP)$_3$ | HRhCO(TPPTS)$_3$ |
| | HRhCO(BISBI)$_3$ | HRhCO(BISBIS)$_3$ |
| | Co$_2$CO$_4$[P($_n$Bu)$_3$]$_2$ | Co$_2$CO$_4$[TPPTS]$_2$ |
| | SnCl$_3$PtCl (TPP)$_2$ | SnCl$_3$PtCl (TPPTS)$_2$ |
| Hydro-genation | RhCl(TPP)$_3$ | RhCl(TPPTs)$_3$ |
| | RuCl$_2$(C$_6$H$_5$)BINAP(S) | RuCl$_2$(C$_6$H$_5$)BINAP(S) |
| | RhClO$_4$Chiraphos (S,S) | RhClO$_4$Chiraphossulfo-nated (S,S) |
| Carbo-nylation | PdAcPTSA(TPP)$_2$ | PdAcPTSA(TPP)$_2$ |
| | Rh(CO)$_2$I$_2$⁻[MeN⁺(Ph)$_3$] | Rh(CO)$_2$I$_2$⁻[MeN⁺(Phm SO$_3$⁻)$_3$] |
| Heck olefination | PdCl$_2$(PPh$_3$)$_2$ | PdCl$_2$(TPPTS)$_2$ |
| Suzuki coupling | PdCl$_2$(PPh$_3$)$_2$ | PdCl$_2$(TPPTS)$_2$ |
| Isomar-ization | PtCl$_2$(PPh$_3$)$_2$ | PtCl$_2$(TPPTS)$_2$ |
| | RhCl(TPP)$_3$ | RhCl(TPPTS)$_3$ |
| Wacker oxidation | Pd(Ac)$_2$BIPY | Pd(Ac)$_2$BIPYDS |
| Oxidation | CoPthalocynine | CoPthalocyninetetrasulfo-nated |
| Michel and Knovengel reactions | NaOH | OH⁻[MeN⁺(PhmSO$_3$⁻)$_3$] |
| | NaOMe | MeO⁻[MeN⁺(PhmSO$_3$⁻)$_3$] |

The supported catalysts according to the invention are extremely active as is born out by the tests in the description, which is given in the examples, which follow. In fact these examples relate to the application of such supported catalysts to the diversity of reactions catalyzed by different mechanisms and according to known theories of molecular catalysts. A comparison of the reactions of these supported catalysts in homogeneous phase establishes that while retaining catalyst activity to considerable extent facile separation can be easily achieved. This makes catalyst suitable for continuous process thereby enhancing catalyst process economics. The said catalyst formulation being inherently solid can be easily recovered after the desired catalytic conversion in the heterogeneous phase. They can then be reused to catalyze new charge of reactants, this operation being either continuous or repeatable wherein the catalyst can be recycled for several times. The advantageous fact is catalytic formulation being repeatable several times without their activity being appreciably degenerating.

Before subjecting catalysts for purpose of catalyzing reactions it is essential that stability and incompatibilities be assessed. For this reason various chemical stresses were applied to stimulate stresses encountered by the catalytic formulation when they are applied to actual reaction. The stresses encountered during reaction or during post processing are solvation stresses due to solvents and media. Ranges of solvents that are applicable are liquids employed for reaction and post processing such as washing. Washing is preferred process to regenerate catalyst to remove adsorbed material and for activation by other chemical treatment.

Figure 2:
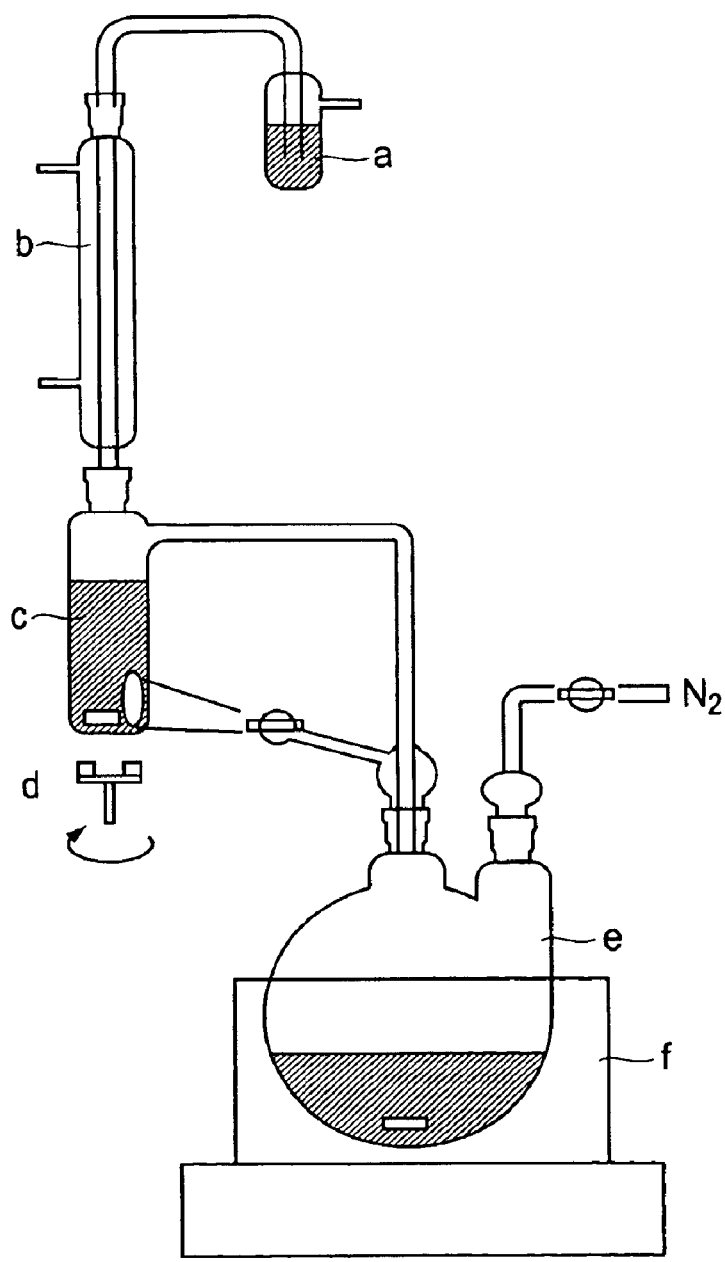
FIG. 2 is the schematic of the continuous liquid extractor for solids wherein, a is the unidirectional gas bubbler connected to condenser, b is the condenser, c is the extraction vessel holding magnetic needle and solid to be leached/ extracted, d is the magnetic stirrer unit, e is the vessel holding extraction liquid, and f is the high temperature bath
Figure 3:
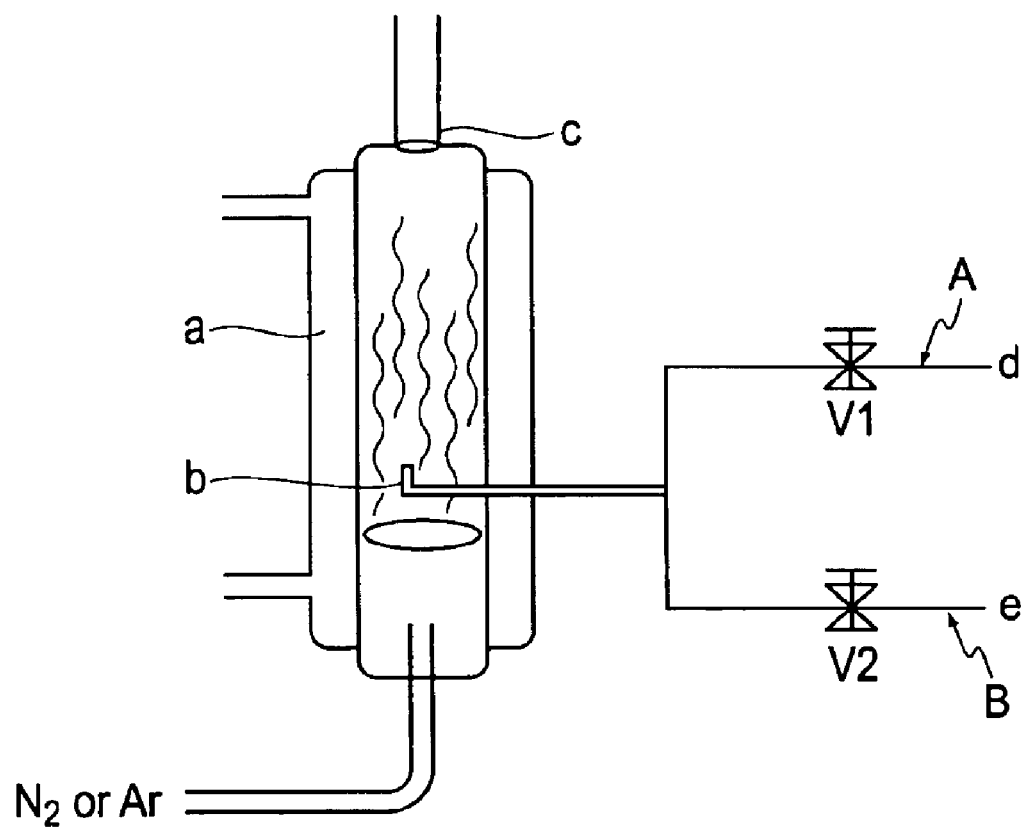
FIG. 3 is the schematic of the fluidized bed in which catalyst formulation is processed wherein, a is the jacket through which constant temperature fluid is circulated, b is the atomizer through which liquids are sprayed in the fluidized bed, c is the gas solid separation mesh, d is the inlet for solution A, e is the inlet for solution B, V1 and V2 are valves
Figure 4:
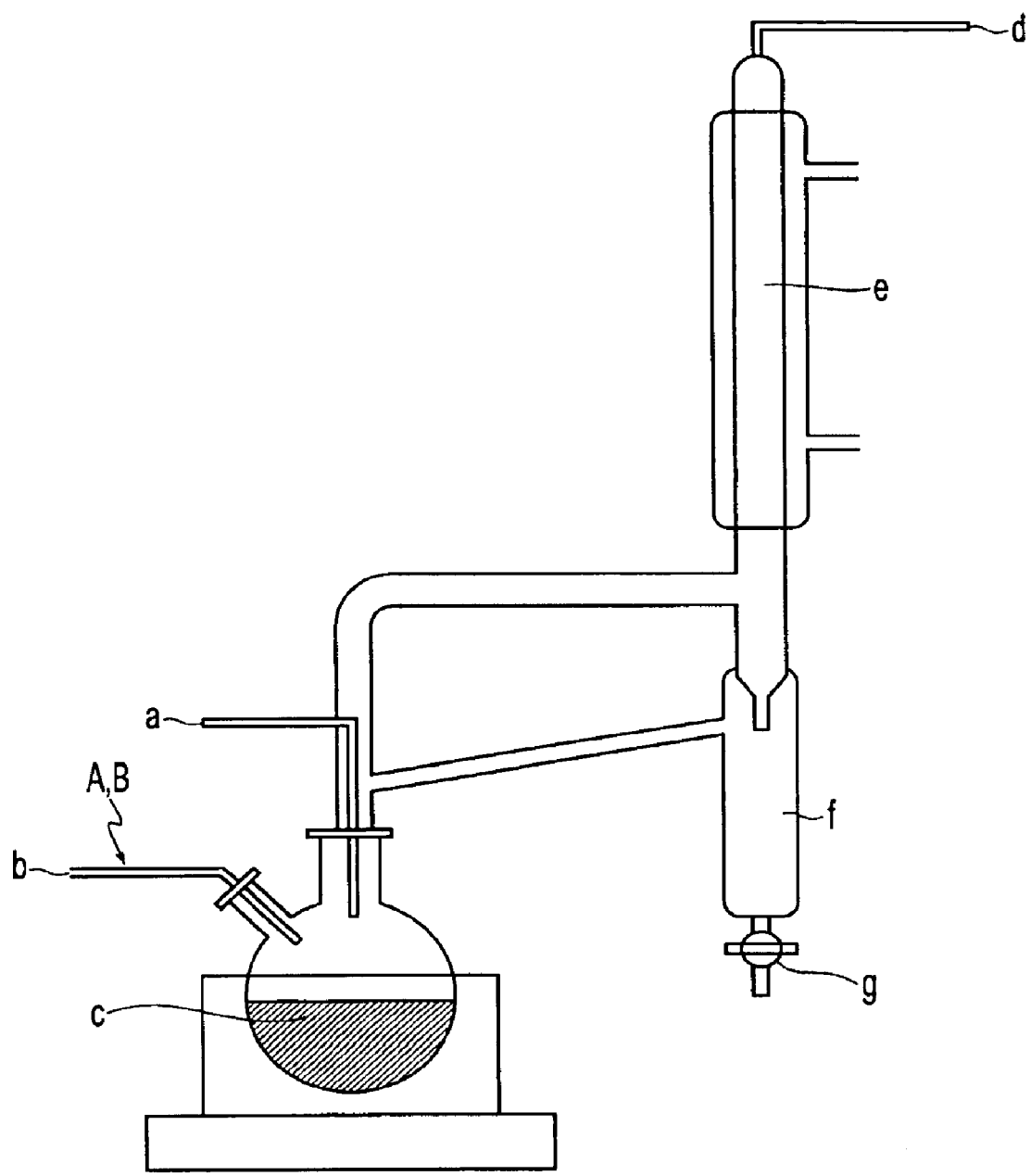
FIG. 4 is the schematic of the catalyst preparation unit with simultaneous removal of liquid wherein, a is the inert gas inlet, b is the inlet for solutions A and B, c is the vessel holding magnetic needle, support and liquid, d inert gas outlet, e is the condenser, f is the liquid collector, g is the collection arm for liquid.

For this reason various catalysts containing different metals such as rhodium, ruthenium, iridium, palladium, platinum, cobalt, nickel, molybdenum and iron were prepared according to methods described earlier and extracted at boiling temperatures of the solvents like, water, acetic acid, methanol, isopropanol, ether, tetrahydrofuran, ethyl acetate, acetone, acetonitrile, toluene, cyclohexane in the apparatus detailed in FIG. 2. The extraction was continued for several hours and subsequently solvent was changed. No appreciable loss of metal content was and physical morphology by visual comparison was detected. It is obviously true that sites containing hydroxy, methoxy and other basic radicals would be destroyed. These experiments indicate that catalyst would be stable in diverse range of solvents and need not be restricted to particular class of solvents. Similarly, catalysts were leached in aqueous acids and alkaline solutions and loss of metals including transition metal or group IIA metal was detected.

The activity of the catalyst studied has been measured in the examples in conventional manner by the turnover number which defines number of molecules converted by the catalytic reaction for a catalytically active entity per unit time under idealized conditions or as yield over a defined period of time.

Various exploratory experiments were carried out to ascertain applicability of the catalyst of the invention. The exploratory experiments were aimed at understanding molecular catalysis. Due to this reason reaction was selected where two products are formed with dissymetric regioselectivity. Hydroformylation is one such reaction wherein; reaction rates and regioselectivities are significantly altered because of variation of molecular environment. Due to these reasons hydroformylation of hexene with $HRhCO(TPPTS)_3$ was considered as suitable probe to understand catalysis in reaction conditions.

Hydroformylation reaction was carried out for hexene as substrate and $HRhCO(TPPTS)_3$ as active catalytic entity (g of rhodium/g of support), moisture content (ppm), silica as support and no excess of ligand. Total conversion was obtained and the catalyst was recovered by centrifugation, washed with toluene, and dried in vacuum. Dry catalyst powder was reused for hydroformylation of allyl alcohol in water catalyst was active for hydroformylation providing aldehydes. Catalyst after reaction was recovered by centrifugation, dried in vacuum, reused for hexene hydroformylation, and found to produce aldehydes. This experiment indicated feasibility of catalyzing reaction in various solvents successively irrespective of substrate.

Accordingly need of support was identified by precipitating $HRhCO(TPPTS)_3$ with barium nitrate precipitate was used to catalyze hexene hydroformylation. After 24 hours, conversion was below 1%.

In order to identify that reactions take place in solid state and not by leaching of complex under reaction conditions, which eventually return to solid. This is verified by using criteria of mobility of catalyst species and additional ligand. In case of soluble catalyst wherein additional ligand is in mobile condition due to which it can interact with active species and there by giving lower rates and high n/I ratio. When catalysts were prepared with additional ligand present no change in activity and selectivity was observed. This observation was attributed to immobile state of ligands and catalyst. Due to immobility of ligands their interaction with active species is totally retarded thereby not affecting rates and n/i ratio.

Immobility of catalyst was further verified by addition of water to the solid catalyst. At lower water content (ppm/g) high conversions were obtained. When moisture content was increased activity was considerably reduced. Same catalyst when dried resumed its original activity. This experiment conclusively verifies that reaction occurs in solid state.

Accordingly the crucial evaluation indicating life of the catalyst, its stability and the durability was performed in a tubular fixed bed reactor by subjecting catalyst to hydroformylation in tubular trical bed reactor ($\phi\frac{1}{2}$") at 80° C. and 300 psi $H_2/CO$ (1:1) using 5 g. of catalyst. 5% decene in toluene was pumped continuously at the feed rate of 10 ml/hr conversion levels were 20% for aldehydes (n/i 2.1) after attaining steady state. The reaction was continued for 72 hr without loss of activity. Reaction was arrested by discontinuing the liquid feed and water was pumped for 1 hr. thereafter reactant feed was resumed. Initially there was no conversion, which was steadily resumed over the period of 10 hr. This observation was attributed to formation of water film on the catalyst surface, which physically retards contact of decene with catalyst surface. Moreover water does not wash out complex catalyst, which provides conclusive proof that reaction occurs in the solid state.

The technique of solid catalyst formulation is established in the present invention according to which the solid catalyst can be formulated and applied for catalyzing reactions in a diversity of solvents. The catalytic formulation referred herein was applied to a variety of reactions according to yet another embodiment. An exemplary reaction class for which catalytic formulation was employable is described in subsequent sections. Reaction classes that are described here are only exemplary and limited by scope of catalytically active entity as said earlier. Variety of reaction classes described herein are intended to outline the scope of catalytic formulation that is under consideration wherein emphasis given on catalyst separation, stability and convenience of operation when applied to manufacture of plurality of organic compounds. Classes of reaction described herein are hydroformylation, hydrogenation, carbonylation, carbon-carbon bond formation by Heck and Suziki type reactions, isomerization, epoxidation, Wacker oxidation, Michel addition and Knovengel condensation.

Metal catalyzed addition of carbon monoxide and hydrogen to olefin provides access to aldehydes and in certain cases followed by hydrogenation. Wide diversity of olefins can be hydroformylated to corresponding aldehydes various olefins were hydroformylated with analogue of classical Wilkinson's catalyst. Various olefins such as hexene, styrene, cyclohexene and vinylacetate were hydroformylated. Similarly hexene was hydroformylated with rhodium modified with different ligands to control selectivity. Accordingly other metals active for hydroformylation were also tested such as cobalt and platinum.

Palladium phosphine complexes catalyze Carbonylation of halides, alcohols and olefins in homogeneous reaction systems. Analogues of such palladium complexes were formulated and tested for styrene, styryl alcohol, phenyl acetylene and bromobenzene. Reasonable activities were obtained in each case and catalyst can be reused.

Various phosphine amines, phosphite complexes of Zr, Hf, V, Cr, Mo, W, Mn, Re, Fe, Ru, Os, Co, Rh, Ir, Ni, Pd, Pt, are useful for hydrogenation of variety of functional groups. Hydrogenation of olefins, carbonyl, and nitroaromatics were tested with the catalyst formulated with this invention.

The extension of substituted alkenes by direct carbon—carbon bond formation at vinylic carbon center is useful reaction for manufacture of variety of organic synthesis. Such synthetic procedure is difficult to achieve by conventional organic synthesis. The palladium complexes (Pd0) have proved to be effective in this sense. Various palladium complexes including phosphine, metalated phosphine and phosphites are useful catalysts other metal such, as nickel and platinum are also useful in this respect. Olefination of aryl bromides was demonstrated with catalytic formulation of the invention.

Palladium catalyzed cross-coupling reactions of aryl or vinyl boronic acids with aryl halides are well known in the art. Such coupling reactions are carried out in polar as well as non-polar media. Palladium phosphine complexes are useful in this respect. Varieties of biaryl compounds are accessible through this reaction. The catalytic formulation of this invention is also suitable for this class of reactions.

Double bond isomerization is useful reaction in converting olefins to isomerized olefins. Various transition metal complexes catalyze this type of reaction. Metal complexes useful in this respect are platinum, palladium, rhodium and cobalt. The catalytic formulation of present invention is also useful in catalyzing this reaction.

Present catalytic formulation is also suitable for oxidation of olefins to epoxides and acids. For example molybdate ion when hetereogenized as quaternary ammonium ion pair can catalyze epoxidation of olefins. Various pthalocyanines are also useful in this respect.

Nucleophilic addition of mesomeric anion to activated olefins such as $\alpha\beta$ unsaturated olefins is known as Michel reaction. Compounds containing electron-withdrawing groups having relatively acidic protons are suitable compounds to form mesomeric anions such compounds are for example R—$CH_2$—Z wherein Z is electron-withdrawing group such as CN, COOR, $NO_2$, CHO etc. and R may be alky aryl or Z as defined earlier. In presence of strong base these compounds for anion R—$CH^{(-)}$—Z which adds to $\alpha$-$\beta$- unsaturated olefins at $\beta$ position. The activated olefins may be represented as C=C—Z where in carbon attached to Z is $\alpha$ and adjacent carbon is $\beta$.

Generally catalyst employed to form said mesomeric ions are strong bases such as $H^-$, $OH^-$, $MeO^-$, etc. Anion fragments as such are difficult to solidify therefore counter cation selected for such is quaternary ammonium compounds, which are functionalized with anionic functional groups, and ion pair as a whole is precipitated on solid support. In cases where quaternary ammonium compounds exist as alcoxy ion pair, solidified quaternary compound formulation is successively washed with solution of alcoxy anion prior to use. Condensation of diethyl malonate with ethyl acrylate, diethyl maleate, acrylonitrile, are demonstrated in examples appended hereinafter.

Condensation of aldehydes or ketones, usually not containing an $\alpha$ hydrogen with compounds of the form R—$CH_2$—Z to form olefins is called as Knovengel reaction (Jones, *Org. react.* 1967, 15, 204–599) wherein Z may be CHO, COR, COOH, COOR, CN, $NO_2$. The catalysts generally employable for this reaction are basic amines, hydroxyl anion or alcoxy anion. Anion fragments as such are difficult to solidify therefore counter cation selected for such is quaternary ammonium compound, which is functionalized with anionic functional groups, and ion pair as a whole is precipitated on solid support. In cases where quaternary ammonium compounds exist as alkoxy ion pair, solidified quaternary compound formulation is successively washed with solution of alcoxy anion prior to use. Condensation of butyraldehyde to 2-ethylhexenal, benzaldehyde and acetone to dibenzyledene acetone, benzaldehyde and acetonitrile to cinnamonitrile are demonstrated in examples appended hereinafter It would be evident from these descriptions that wide diversity of soluble catalysts can be formulated by appropriately forming catalytic entities that are anionically charged. These entities are structurally analogues to the soluble catalytic entities. The catalysts that are employable in this context are metal complexes, quaternary ammonium compounds wherein complimentary anion is catalyst (complimentary anion can be metal complex, organometallic anion or inorganic anion).

The present invention was conceived without limiting the said solid catalytic formulation to one particular class of complexes or reaction catalyzed by them following certain mechanism, according to some particular theory. It is perceived that solid support having high surface area provides a mechanical strength and a surface upon which insoluble catalytic material is physically implanted. The insoluble material is generated from interaction of otherwise soluble complex catalyst containing two or more anionic functional groups and calcium, strontium and barium salt solutions. This material is formed on the surface of the solid support as a vehicle. The composite solid assembly resulting therefrom can be suitably used as solid catalyst.

Moreover, recycling and regeneration of applicants' preferred catalytic formulations is readily accomplished using known methods and procedures, for example when acceptable conversion level has occurred in a given batch run whether it is determined by elapsed time or monitored by consumption of substrate or some other parameter. The vessel need only be brought to ambient temperatures and vented off residual pressure if any. The reaction mixture thereafter may simply be separated from catalyst by simple decanting. The catalytic formulation is filtered and possibly washed with suitable liquid for later reuse or simply recharged with feedstock as needed and a subsequent reaction begun.

As catalyst lifetimes are better understood through working with a particular catalyst formulation in repeated recycling in either laboratory or in commercial settings it may be further desirable to regenerate catalyst time to time either by washing with suitable liquid or by specific chemical treatment. Continuous reaction processes are also practicable for applicants preferred catalysts in view of their insolubility and resistance to leaching or other disintegration. Such processes can be designed and implemented using common and known procedures in the art.

For the purpose of further promoting a better understanding of the catalysts and processes of the present invention, reference will now be made in the examples below to specific instances of their preparation and use. These examples are exemplary only and no limitation of the scope or breadth of applicants' invention is intended thereby. Various modifications and variations of this invention will be obvious to a worker skilled in the art and it is to be understood that such modifications and variations are to be included within the purview of this application and the spirit and the scope of the appended claims

EXAMPLES

Experiment 1
(Verification of the hypothesis)

This comparative example illustrates the validation of the hypothesis that anions having two or more negative charges when interacted with group IIA metal cations except $Mg^{+2}$ invariably result in to a precipitate which is practically insoluble in organic solvents (including nonpolar, polar (protic and aprotic) and sparingly soluble in aqueous solvent in certain cases). This hypothesis was verified as follows. Solutions of different anions were interacted with group IIA metal ions. 0.1 molar solutions of anionic component (solution A) and 0.1 molar solutions of group IIA cation (solution B) component were prepared. 10 ml of solution B was mixed with 50 ml of solution A in boiling tubes solutions were thoroughly mixed on shaker for 10 hr. resulting suspensions were centrifuged and precipitate was removed by decanting supernatant liquid. Residual precipitate was diluted with distilled water followed by centrifugation and decantation was repeated thrice. To this precipitate 10 ml methanol was added and centrifugation and decantation procedure was repeated resulting wet precipitates were vacuum dried at 50° C. Mixtures where precipitate was not observed were discarded. Dried precipitate barium and strontium were found insoluble in water, methanol, ethanol, propanol, butanol, acetic acid, benzene xylene, petroleum ether, ethyl acetate, acetone methyl ethyl ketone, acetonitrile, dimethylformamide, chloroform, tetrahydrofuran. Where as some salts of calcium were found sparingly soluble.

Results are summarized in following table.

| Solution of group IIA metal cation (0.1 molar) | Solution of anion (0.1 molar) | observation |
|---|---|---|
| Magnesium chloride | Sodium nitrate | No precipitate |
| Calcium chloride | Sodium nitrate | No precipitate |
| Strontium chloride | Sodium nitrate | No precipitate |
| Barium chloride | Sodium nitrate | No precipitate |
| Magnesium chloride | Sodium propionate | No precipitate |
| Calcium chloride | Sodium propionate | No precipitate |
| Strontium chloride | Sodium propionate | No precipitate |
| Barium chloride | Sodium propionate | No precipitate |
| Magnesium chloride | p-toluene sulfonate sodium | No precipitate |
| Calcium chloride | p-toluene sulfonate sodium | No precipitate |
| Strontium chloride | p-toluene sulfonate sodium | No precipitate |
| Barium chloride | p-tolune sulfonate sodium | No precipitate |
| Magnesium chloride | m-benzene di-sulfonate disodium | No precipitate |
| Calcium chloride | m-benzene di-sulfonate disodium | White precipitate |
| Strontium chloride | m-benzene di-sulfonate disodium | White precipitate |
| Barium chloride | m-benzene di-sulfonate disodium | White precipitate |
| Magnesium chloride | di-sodium oxalate | No precipitate |
| Calcium chloride | di-sodium oxalate | White precipitate |
| Strontium chloride | di-sodium oxalate | White precipitate |
| Barium chloride | di-sodium oxalate | White precipitate |
| Magnesium chloride | Sodium Sulfate | No precipitate |
| Calcium chloride | Sodium Sulfate | White precipitate |
| Strontium chloride | Sodium Sulfate | White precipitate |
| Barium chloride | Sodium Sulfate | White precipitate |
| Magnesium chloride | di-sodium phenyl phosphonate | No precipitate |
| Calcium chloride | di-sodium phenyl phosphonate | White precipitate |
| Strontium chloride | di-sodium phenyl phosphonate | White precipitate |
| Barium chloride | di-sodium phenyl phosphonate | White precipitate |
| Magnesium chloride | $Na_2HPO_4$ | No precipitate |
| Calcium chloride | $Na_2HPO_4$ | White precipitate |
| Strontium chloride | $Na_2HPO_4$ | White precipitate |
| Barium chloride | $Na_2HPO_4$ | White precipitate |

-continued

| Solution of group IIA metal cation (0.1 molar) | Solution of anion (0.1 molar) | observation |
|---|---|---|
| Magnesium chloride | di-sodium phthalate | No precipitate |
| Calcium chloride | di-sodium phthalate | White precipitate |
| Strontium chloride | di-sodium phthalate | White precipitate |
| Barium chloride | di-sodium phthalate | White precipitate |
| Magnesium chloride | Ammonium molybdate | No precipitate |
| Calcium chloride | Ammonium molybdate | White precipitate |
| Strontium chloride | Ammonium molybdate | White precipitate |
| Barium chloride | Ammonium molybdate | White precipitate |
| Magnesium chloride | Sodium carboxy methyl cellulose | No precipitate |
| Calcium chloride | Sodium carboxy methyl cellulose | White precipitate |
| Strontium chloride | Sodium carboxy methyl cellulose | White precipitate |
| Barium chloride | Sodium carboxy methyl cellulose | White precipitate |
| Magnesium chloride | Sodium poly-vinyl sulfonate | No precipitate |
| Calcium chloride | Sodium poly-vinyl sulfonate | White precipitate |
| Strontium chloride | Sodium poly-vinyl sulfonate | White precipitate |
| Barium chloride | Sodium poly-vinyl sulfonate | White precipitate |

In addition to these, EDTA acetyl acetonate, hydride compounds of calcium were interacted with sodium sulfate, sodium phosphate to yield insoluble precipitate.

Experiment 2

Synthesis of high purity oleum 2 lit. Three-necked flask was attached with distillation condenser, addition funnel and to another end collection vessel with bottom drain valve. Distillation condenser was also provided with pressure relief non-return valve. In flask magnetic bar was placed and 500 g. $P_2O_5$ was charged. 45 ml conc. $H_2SO_4$ was placed in collection vessel. 400 ml conc. $H_2SO_4$ was placed in addition funnel. Addition was started with simultaneous magnetic agitation over the period of 2 hours. Temperature of flask was raised slowly until slow distillation of sulfur trioxide was started. Sulfur trioxide was collected in conc. $H_2SO_4$ in collection vessel after total volume of liquid in collection vessel reached to 148 ml, heating was stopped and assembly was dismantled.

Experiment 3

Synthesis of Triphenyl phosphine trisulfonate

Triphenyl phosphine trisulfonate was synthesized by following procedure. Triphenylphosphine 50 g. was placed in sulfonation reaction followed by vacuum argon degassing and blanketed with argon. Sulfonation reactor was cooled to 5° C. and 200 g sulfuric acid was charged in the sulfonation reactor without allowing temperature of reactor to cross 10° C. Addition of sulfuric acid was carried out with constant stirring with mechanical stirrer over a period of 2 hours. Reaction mixture assumed pale yellow color. To this reactor 280 g of 65% oleum prepared as per previous experiment was charged over a period of 60 min. temperature of the sulfonation reactor was raised to 22° C. and reaction was continued for 76 hours. There after temperature of the reaction was lowered to 0° C. and 50 ml distilled and degassed water was introduced in the sulfonation reactor without allowing temperature to rise beyond 5° C. over a period of three to four hours. This solution was further diluted with 500 ml water. The diluted solution was transferred to 3-lit jacketed vessel and chilled to 5° C. and consequently neutralized with 50% w/w NaOH in water, which was previously degassed. At neutralization point solution assumed distinct yellow color at this instance NaOH addition was discontinued and pH was lowered to 6 by addition of con sulfuric acid. During neutralization formed sodium sulfate partially precipitates which was removed by filtration and resulting solution was concentrated under vacuum to 300 ml. formed sodium sulfate was removed by filtration. Mother liquor containing TPPTS was further diluted with 2000 ml degassed methanol and refluxed for two hours during which most of the sodium sulfate precipitated, supernatant extract of TPPTS in methanol was removed by filtration TPPTS extract in methanol was evaporated to dryness and white colored solid was obtained (purity above 95% by $P^{31}NMR$). This solid was dissolved in minimum amount of water and reprecipitated with degassed ethanol to obtain TPPTS with purity >99%.

Experiment 4

Synthesis of disodium P-phenyl-3,3'-phosphine dialy bis (benzene sulfonate)

Orthoboric acid (48 g) was dissolved in concentrated sulfuric acid 98% (200 ml) to this was added 65% oleum 200 ml. the temperature of the solution was raised to 60° C. and excess sulfur trioxide was removed in high vacuum by providing a gas trap attachment containing calcium oxide (trap was chilled to −10° C.) solution of orthoboric acid and sulfur trioxide was cooled to 5° C. and 30 g triphenyl phosphine was added under argon blanket. Resulting mixture was agitated by mechanical stirrer and temperature of the reactor was raised to 58° C. and reaction was continued for 90 hours. The temperature was reduced to 0° C. and hydrolyzed with 500 ml degassed water. This solution was neutralized with 50% w/w sodium hydroxide in water until neutralization and formed precipitate was removed by filtration and mother liquor was concentrated to 300 ml and diluted with 1000 ml methanol and refluxed for 2 hours. Resulting precipitate was removed by filtration. The extract in methanol was evaporated to obtain a solid which was suspended in 1000 ml methanol and to this 50 g microcrystalline cellulose avicel was added followed by 20 ml conc. $H_2SO_4$ and refluxed for 6 hours under argon blanket. Solution was cooled and filtered to remove avicel. To this 50 g. Avicel™ was again added and refluxed for another 6 hours suspension was filtered and methanolic extract was neutralized with 50% NaOH w/w and filtered. Solution was evaporated to obtain white compound correct elemental analysis.

Experiment 5

Synthesis of trisodium 3,3',3''-phosphine trial tris (4 methyl benzene sulfonate)

Orthoboric acid (g., 6.6 mmol) was dissolved in concentrated sulfuric acid (96%, 3.75 ml) to this (2-methylphenyl) phosphine (0.50 g., 1.4 mmol) was dissolved in reaction mixture. Oleum (6.75 ml, 65% w/w) was added drop wise while temperature of reaction mixture was 0° C. After stirring for 72 hours at 25° C., the temperature was lowered to 0° C. and the mixture was hydrolyzed by addition of 5 ml degassed water. This solution was neutralized with 50% w/w sodium hydroxide in water until neutralization and formed precipitate was removed by filtration and mother liquor was concentrated to 3 ml and diluted with 10 ml methanol and refluxed for 2 hours. Resulting precipitate was removed by filtration. The extract in methanol was evaporated to obtain a solid which was suspended in 10 ml methanol and to this 0.5 g microcrystalline cellulose avicel was added followed by 0.5 ml conc. $H_2SO_4$ and refluxed for 6 hours under argon blanket. Solution was cooled and filtered to remove avicel. To this 0.5 g. aviel was again added and refluxed for another 6 hours suspension was filtered and methanolic extract was neutralized with 50% NaOH w/w and filtered. Solution was evaporated to obtain white compound correct elemental analysis.

Experiment 6

Synthesis of sodium salt of sulfonated tribenzyl phosphine

Sulfonation of tribenzyl phosphine was carried out analogous to triphenyl phosphine except exact degree of sulfonation was not established reaction mixture containing di and tri sulfonated phosphine was used for further experiment.

Experiment 7

Sulfonation of 1-3 bis-diphenyl phosphino propane 4.95 g. (12 mmol) of diphenylphosphino propane was dissolved in a solution of 4 g. (64.7 mmol) orthoboric acid in 37.5 ml (98%) reaction mixture was cooled to 0° C., to this 65% oleum 67.5 ml was added drop wise over a period of 2 hours. After addition reaction mixture was brought to 25° C. and stirred for 48 hours. After this reaction mixture was brought to 0° C. and hydrolyzed with 50 ml degassed water. This solution was neutralized with 50% w/w sodium hydroxide in water until pH 7 and formed precipitate was removed by filtration and mother liquor was concentrated to 30 ml and diluted with 100 ml methanol and refluxed for 2 hours. Resulting precipitate was removed by filtration. The extract in methanol was evaporated to obtain a solid which was suspended in 100 ml methanol and to this 5 g microcrystalline cellulose avicel was added followed by 1 ml conc $H_2SO_4$ and refluxed for 6 hours under argon blanket. Solution was cooled and filtered to remove avicel. To this 5 g. avicel was again added and refluxed for another 6 hours suspension was filtered and methanolic extract was neutralized with 50% NaOH w/w and filtered. Solution was evaporated to obtain a white compound.

Experiment 8

Sulfonation of 1-2 bis-diphenyl phosphino ethane

Preparation was carried out in analogous manner as explained in previous experiment Experiment 9

2,2'-bis(diphenylphosphinomethyl)-1,1'biphenyl (Bisbi) synthesis and sulfonation Equip a three liter three-necked flask with a sealed mechanical stirrer, a reflux condenser and a thermometer. Dissolve 89 g. (0.5 mol) of phenanthrene in one liter glacial acetic acid in the flask and warm to 85° C. on a water bath. Introduce 345 ml of 30% hydrogen peroxide solution (4 mol) during 40 min. temperature falls to about 80° C. continue for 6 hr. remove acetic acid and water under reduced pressure to obtain brown color solid digest this residue in 2N sodium hydroxide solution and add 4 g of powdered charcoal and warm the mixture to 75° C. and filter. Filtrate was acidified to pH 2 with the conc. HCl white precipitate was filtered and dried at 50° C. MP 109° C., 83 g 69% material obtained is of sufficient purity for further synthesis.

Equip a three liter three-necked flask with a sealed mechanical stirrer, a reflux condenser and a thermometer.

Flask was cooled to 0° C. in ice salt bath. Reaction vessel was charged with 24.2 g (0.1 mol) diphenic acid and 15.12 g (0.4 mol) sodium borohydride to this solid powder 200 ml dry tetrahydro furan was added in such a way that there is minimum effervescence. After 1 hour suspension becomes uniform and to this (0.2 mol $H_2SO_4$ in 100 ml tetrahydrofuran was added over a period of 2 hours while maintaining temperature at 0° C. after addition was over mixture was allowed to stir for 24 hours at room temperature. To this white suspension 100 ml 30% NaOH was added and refluxed for 4 hours and liquid was brought to room temperature and extracted with chloroform to yield white solid. Which was used further without purification.

Diol intermediate (0.08 mol) from above said preparation was dissolved in chloroform and transferred to two necked flask attached with condenser and guard tube, pressure equalizing addition vessel. One drop of pyridine was added to flask and (0.2 mol) thionyl chloride was dissolved in 25 ml chloroform and charged in addition vessel. Thionyl chloride was added to round bottom flask at room temperature. During addition considerable amount of sulfur dioxide and hydrogen chloride escaped from guard tube. The temperature of the flask was raised until chloroform started refluxing. After 5 hours reaction was quenched by addition of water. Chloroform was extracted with bicarbonate solution followed by water and dried by passing through bed of sodium sulfate. Chloroform was evaporated under vacuum at 50° C. to yield yellow colored oil (irritant and inflammatory to skin), which was distilled, in high vacuum to yield pale yellow colored oil.

(Following procedure was adopted from U.S. Pat. No. 4,879,416).

To a 500 ml flask equipped with a mechanical stirrer, thermowell, addition funnel and condencer was added triphenyl phosphine 16.77 g, 0.064 mols, tetrahydrofuran 64 ml and lithium wire 0.88 g, 0.128 atoms. The flask was cooled to 15° C. reaction mixture was stirred overnight to yield red colored solution with complete dissolution of lithium. The flask was cooled further to 5° C. and tertiary butyl chloride 5.92 g 0.064 mols was added and temperature was raised to 50° C. and maintained for 2 hours. Reaction mixture was cooled and to this 7.5 g of above said dichloride was slowly added. Temperature of the reaction mixture was raised such that it gently boils. Reaction was quenched by addition of 5 ml methanol. The reaction mixture was evaporated to yield sticky mass, which was dissolved in sufficient diethyl ether and washed with water. Evaporation of diethyl ether yields pale yellow colored sticky mass, which was recrystallized from THF/Methanol to yild fine crystals of white material.

This material was sulfonated according to method described for diphenyl phosphino propane. To produce white coloured compound, which was soluble in water.

Experiment 10
Sulfonation of (R) BINAP (2,2'-bisdiphenylphosphino-1,1'binapthyl)

Procedure of sulfonation was adopted from U.S. Pat. No. 5,756,838. 0.5 g. of (R) BINAP was dissolved in 1.75 ml of concentrated sulfuric acid at 10° C. under argon. Afterwards, 7.5 ml of oleum 40% w/w was added dropwise over 2–3 hours the resulting mixture was stirred at 10° C. for 76 hours. After stirring this mixture was slowly poured over 100 g ice followed by dropwise addition of 50% w/w NaOH until solution was neutralized to pH 7. The resulting solution was concentrated under vacuum to 30 ml. to this 100 ml methanol was added in order to precipitate sodium sulfate. Methanolic extracted was evaporated under vacuum to obtain solid, which was dissolved in methanol and filtered. Methanol was evaporated to obtain white solid.

Experiment 11
Sulfonation of (S, S chiraphos) (S) (S) 2,3 bisdiphenylphosphino butane.

Procedure of sulfonation was adapted from Alario et al, J. Chem. Soc., Chem. Commun., 1986, 202

Experiment 12
Sulfonation of R prophos 1,2 (S) bisdiphenylphosphino propane

Procedure of sulfonation was adapted from Amrani et al Organometallics 1989, 8, 542

Experiment 13
Sulfonation of R, R 2-5,bis diphenylphosphino penatne

Procedure of sulfonation was adapted from Amrani et al Organometallics 1989, 8, 542 Sulfonation of 2-pyridyl phosphine

Experiment 14
Synthesis of sodium salt of sulphonate of triphenylamine.

2 g of Triphenyl amine was charged into a reactor, and 20 cc of concentrated sulfuric acid was added to it. This mixture was stirred until the amine dissolved. 20 cc of oleum 65% was added to this mixture under rapid stirring, and the reactor was cooled to about 20° C. After the addition of oleum, the reactants and contents were heated to 50° C. and maintained at this temperature for 48 hours. The reactor and its contents were cooled, and distilled water (10 cc) was added to the reaction mixture to quench the oleum. 50% NaOH solution was added to this solution, under cooling (10° C.) until the sulfuric acid solution was neutralized. The solution was concentrated and then methanol was added to extract the water-soluble ligand from the sodium sulfate powder. The methanol was evaporated to yield the water-soluble sodium salt of triphenyl amino sulfonic acid [1.6 g]. The product consists of mixtures of the bis and grater than 95% tris sulfonation products. These can be used as such in synthesis of metal complexes for catalysis.

Experiment 15
Trisodium salt of tribenzylamine trisulfonate 2 g of Tribenzyl amine was charged into a reactor, and 20 cc of concentrated sulfuric acid was added to it. This mixture was stirred until the amine dissolved. 20 cc of oleum 65% was added to this mixture under rapid stirring, and the reactor was cooled to about 20° C. After the addition of oleum, the reactants and contents were heated to 50° C. and maintained at this temperature for 48 hours. The reactor and its contents were cooled, and distilled water (10 cc) was added to the reaction mixture to quench the oleum. 50% NaOH solution was added to this solution, under cooling (10° C.) until the sulfuric acid solution was neutralized. The solution was concentrated and then methanol was added to extract the water-soluble ligand from the sodium sulfate powder. The methanol was evaporated to yield the water-soluble sodium salts of Tribenzyl amino sulfonic acid [1.7 g] degree of sulfonation was established by H1 NMR and elemental analysis.

Experiment 16
Synthesis of sodium salt of sulphonate of 2,2'bipyridine.

2 g of 2,2'Bipyridine was charged into a reactor, and 20 cc of concentrated sulfuric acid was added to it. This mixture was stirred until the amine dissolved. 20 cc of oleum 65% was added to this mixture under rapid stirring, and the reactor was cooled to about 20° C. After the solution of oleum, the reactants and contents were heated to 50° C. and maintained at this temperature for 48 hours. The reactor and its contents were cooled, and distilled water (10 cc) was added to the reaction mixture to quench the oleum. 50% NaOH solution was added to this solution, under cooling (10° C.) until the sulfuric acid solution was neutralized. The solution was concentrated and then methanol was added to extract the water-soluble ligand from the sodium sulfate powder. The methanol was evaporated to yield the water-soluble sodium salt of 2,2'bipyridine di sulfonic acid. [1.2 g] The product consists of mixtures of the bis sulfonation products as indicated by elemental analysis and 1h NMR. These can be used as such in synthesis of metal complexes for catalysis.

Experiment 17
Sulfonation of 2 phenyl pyridine 2 g of 2,phenylpyridine was charged into a reactor, and 20 cc of concentrated sulfuric acid was added to it. This mixture was stirred until the amine dissolved. 20 cc of oleum 65% was added to this mixture under rapid stirring, and the reactor was cooled to about 20° C. After the addition of oleum, the reactants and contents were heated to 50° C. and maintained at this temperature for 48 hours. The reactor and its contents were cooled, and distilled water (10 cc) was added to the reaction mixture to quench the oleum. 50% NaOH solution was added to this solution, under cooling (10° C.) until the sulfuric acid solution was neutralized. The solution was concentrated and then methanol was added to extract the water-soluble ligand from the sodium sulfate powder. The methanol was evaporated to yield the water-soluble sodium salt of 2-phenylpyridine sulfonic acid. [1.2 g] The product consists of mixtures of the bis sulfonation products as indicated by elemental analysis. These can be used as such in synthesis of metal complexes for catalysis.

Experiment 18
Synthesis of 2-3 bisdiphenylphosphino, succinic acid sodium salt

To a reaction system comprising a solution of dimethyl maleate (50 g.) in chloroform (100 ml) was added a solution of bromine (15 ml) in chloroform 100 ml over a period of 2 hours. The reaction mixture was stirred for 2 hours at the end of reaction mixture was washed twice with 100 ml saturated sodium thiosulphate and then twice with 100 ml water. Organic part was passed through 5 g. sodium sulphate and subsequently treated with activated charcoal. Chloroform was stripped off to yield 60 g oil.

Subsequent reaction was set up with 250 ml. three necked glass vessel equipped with addition funnel magnetic stirrer and rubber septum. Assembly was flushed with argon. To this vessel finely cut lithium ribbon (500 mg.) was added and assembly was evacuated and refilled with argon. To this assembly, 50 ml tetra hydrofuran was added with gas tight syringe maintaining argon blanket 8.3 ml chlorodiphenyl phosphine was placed in addition funnel set up was evacuated and refilled with argon contents of addition funnel were dropped in the lithium suspension, during lithium dissolution solution started assuming red color and reaction mixture was stirred for 4 hours after complete dissolution of lithium.

To another 250 ml vessel equipped with reflux condenser and rubber septum 30 ml dry tetrahydrofuran was placed by syringe and assembly was evaccuated and refilled with argon. To this 4.52 g of brominated diethyl maleate was transferred by syringe followed by 30 ml of lithium phosphied soultion (red colored). Contents of the reaction mixture were maintained at 80° C. for 12 hours. To this reaction mixture 1 ml methanol was added and tetrahydrofuran was removed under vacuum. Syrupy orange coloured liquid was washed twice with 25 ml ether. 1 g of this syrupy orange product was transferred to three necked round bottomed flask attached with reflux condenser the set up was thoroughly flushed with argon and 20 ml 2% sodium hydroxide were refluxed the reaction mixture was cooled to 5° C. and precipitated white material of diphosphine was recovered by filtration yield 1 g.

Experiment 19
Quaternization of tribenzyl amine tri sulfonate with benzyl chloride To a mixture of (0.1 mol) tribenzylamine trisulfonate and benzyl chloride (0.2 mol) was added 50 ml water and 50 ml dimethyl formamide. Solution was stirred at 70° C. for 76 hours and reaction was monitored by disappearance of benzyl chloride. Reaction mixture was evaporated under vacuum to yield a solid mass, which was dissolved in minimal amount of water, and aqueous solution was washed with diethyl ether. Aqueous extract was dried under vacuum and solid was stored in dry condition.

Experiment 20
Synthesis of quaternary ammonium hydroxide 17 g. (0.1 mol) of silver nitrate was dissolved in 170 ml of distilled water and warmed to 85° C. and 3.9 g (0.097 mol) sodium hydroxide was added to it. Mixture was agitated vigorously until coagulation of precipitation is complete. Precipitate was recovered by centrifugation and suspended in 100 ml water to which was added (0.09 mol) of above quaternaryammonium compound. Reaction mixture was stirred for 3 hours under nitrogen and filtured. Liquid was evaporated under vacuum at room temperature to obtain a solid.

Experiment 21
Quaternization of triphenyl amine with benzyl chloride

To a mixture of (0.1 mol) triphenylamine trisulfonate and benzyl chloride (0.2 mol) was added 50 ml water and 50 ml dimethyl formamide. Solution was stirred at 70° C. for 76 hours and reaction was monitored by disappearance of benzyl chloride. Reaction mixture was evaporated under vacuum to yield a solid mass, which was dissolved in minimal amount of water, and aqueous solution was washed with diethyl ether. Aqueous extract was dried under vacuum and solid was stored in dry condition.

Experiment 22
Formation of quaternary ammonium hydroxide of quaternary ammonium salt of n benzyl triphenyl amine.

Experiment 23
Synthesis of hydridocarbonyl tris (trisodiumtriphenylphosphine trisulfonate) rhodium (I)

The procedure was adopted from U.S. Pat. No. 4,994,427 dated Feb. 19, 1991 to Davis et al. 500 mg. Acetyl acetonate dicarbonyl rhodium (I) was added to vigorously stirred 10 ml deaerated solution of 4 g. of sodium triphenylphosphine trisulfonate in water. After dissolution was complete stirring was continued for six hours under atmosphere of 1:1 $H_2/CO$. The solution was then centrifuged to remove precipitated rhodium. To this solution 80 ml absolute ethanol saturated with 1:1 $H_2/CO$ were added to precipitate desired complex. Precipitate was recovered and vacuum dried.

Experiment 24
Dichloro bis (tris triphenylphosphine sulfonato trisodium) palladium (II)

This procedure was adapted from Jiang et al J. Mol. Catal. A: Chemical 130 (1998) 79–84, 100 mg $PdCl_2$ and 2 ml 2

M HCl were added to a schlenk flask and the mixture was stirred at 50° C. until PdCl$_2$ was dissolved completely. After the flask was cooled to room temperature and flushed with argon, 0.80 g. TPPTS was added in to the flask under stirring. The color of the solution changed from dark red to yellow immediately. After 10 min stirring, 15-ml ethanol was added, alight yellow powder precipitated and mixture was stirred for 30 min. The filtered precipitate was washed three times with 30-ml. warm 95% ethanol and dried in vacuum.

Experiment 25
Synthesis of trans-PtCl$_2$ (TPPTS)$_2$

The platinum complex PtCl$_2$ (NCPh)$_2$ 235 mg (0.5 mmol) was dissolved in 10 ml toluene to this solution was added to aqueous solution of TPPTS (568 mg 1 mmol) in 10 ml water to this mixture isopropanol 3 ml was added and reaction mixture was stirred at 50° C. for 10 h complex was recovered from aqueous phase by evaporation 620 mg of PtCl$_2$ (TPPTS)$_2$. 6 H$_2$O.

Experiment 26
Synthesis of NiCl$_2$/TPPTS

Nickel chloridehexahydrate (0.05 mols) was reacted with tppts (0.12 mols) in water sufficient to dissolve and formed complex was precipitated by ethanol

Experiment 27
Synthesis of IrCl (COD)/TPPTS

IrCl (COD) (0.01 mol) was dissolved in minimum amount of tolune and exchanged with). 04 mols of tppts dissolved in minimum amound of water. Tolune layer was removed and aqueous layer was dried.

Experiment 28
Synthesis of [Ru (Cl) (μ-Cl) (TPPTS)$_2$]

The method was adopted from M. Hernandez et al, J. Mol. Catal. A: Chemical 116 (1997) 117–130. RuCl$_2$ (PPh$_3$)$_3$ 5.8 g. 6 mmol was dissolved in 150 ml of tetrahydrofuran and heated to 60° C. A 30 ml water solution of TPPTS (6.3 g 10.1 mol was added drop wise under vigorous stirring. The biphasic medium was stirred further for 30 min at 60° C. After cooling to room temperature, 140 ml of orange layer was removed. The resulting solution was filtered out. Then the deep red aqueous phase was evaporated to dryness and further dried in vacuum.

Experiment 29
Synthesis of [Ru(H)(Cl)(TPPTS)$_3$]

The method was adopted from M. Hernandez et al, J. Mol. Catal. A: Chemical 116 (1997) 117–130. This complex was prepared from [Ru(H)(Cl)(PPh$_3$)$_3$]. PhCH$_3$ 3 g. 3.3 mmol dissolved in 120 ml tetra hydrofuran; TPPTS 5 g. (8 mmol); H$_2$O 30 ml. a bright purple coloured solid was recovered from aqueous layer.

Experiment 30
Synthesis of [Ru(H)$_2$(TPPTS)$_4$]

0.1 g. (0.38 mmol) of RuCl$_3$. 3H$_2$O and 1.07 g TPPTS 1.72 mmol were dissolved in 10 ml of distilled water. The deep brown coloured solution was stirred at room temperature while passing stream of hydrogen. After 10 min 0.17 g. (~4.5 mmol) of NaBH$_4$ were added. Solution turned instantaniously brown yellow with vigorous effervescence. The mixture was heated to 50° C. for 10 min after cooling and evaporation to dryness solid was obtained

Experiment 31
Synthesis of Ru/Binapts complex

Ruthenium binap 4 SO$_3$Na catalyst was prepared by reacting (0.01 g) of [Ru(benzene)Cl$_2$]$_2$ with two equivalents of (0.05 g) R- binap 4 SO$_3$Na in a 1:8 benzene ethanol mixture 4.5 ml to yield [Ru(benzene)Cl] R- binap 4 SO$_3$Na. Resulting solution was vacuum dried.

Experiment 32
Synthesis of Rh$^+$/chiraphos tetra sulfonate complex

Rh$^+$/chiraphos tetra sulfonate catalyst was prepared by reacting [Rh (COD) Cl]$_2$, with two mole equivalents of sulfonated ligand in water at room temperature in presence of excess sodium perchlorate to form cationic complex

Experiment 33
Synthesis of palladium acetate sulfonated bypyridyl complex

Synthesis procedure was adopted from brink et al Chem. Commun, 1998, 2359–2360. Pd(OAc)$_2$ 0.1 mmol and sulfonated bypyridyl 0.1 mmol were stirred overnight with 42.5 g of water to afford a clear orange colored solution which was evaporated to dryness.

Experiment 34
Tetrasodium salt of Cobalt (II) 4,4',4",4'",-Tetrasulfophthalocynine (procedure is adopted from Inorg. Chem. Vol 4, No. 4 April 1965, 469–471)

The monosodium salt of 4-sulfopthalic acid (4.32 g., 0.0162 mol.), ammonium chloride (0.47 g., 0.009 mol.), urea (5.8 g., 0.097 mol.) ammonium molybdate (0.068 g., 0.00006 mol), and cobalt (II) sulfate 2 H$_2$O (1.36 g., 0.0048 mol) and 100 ml celite were ground together in nitrobenzene to form a homogeneous paste and diluted to 50 ml with nitrobenzene in round bottomed flask attached with reflux condenser. The reaction mixture was heated to 180° C. The reaction mixture was heated slowly with overhead stirring while maintaining temperature 180–190° C. The heterogeneous mixture was heated for 6 hours at 180° C. The crude product was recovered by cooling reaction mixture and removing nitrobenzene. Solid cake was washed with hexane followed by methanol until nitrobenzene was removed. The solid residue was transferred to 110 ml 1 N hydrochloric acid saturated with sodium chloride. The mixture was heated briefly to boiling, cooled to room temperature and filtered. The resulting solution was dissolved in 10 ml of 0.1 N NaOH. The solution was heated to 80° C. and insoluble impurities were immediately separated by filtration. Sodium chloride (27 g. was added to solution and slurry was heated to 80° C. until ammonia evolution ceased. Reaction mixture was cooled to room temperature and filtered. This re-precipitation process was repeated twice and solid was filtered and washed with 80% ethanol until filtrate was chloride free as tested by silver nitrate solution. This solid was refluxed in 20-ml ethanol for 4 hours to get pure product, which was dried over P$_2$O$_5$ yield 65% correct elemental

Experiment 35
Tetrasodium salt of copper(II) 4,4',4",4'",-Tetrasulfophthalocynine The compound was prepared using similar mole ratios of the reactant except 0.0048 mol of copper sulfate 5.H$_2$O. and purified as described for Tetrasodium salt of Cobalt(II)4,4', 4",4'",-Tetrasulfophthalocynine

Experiment 36
Tetrasodium salt of Manganese(II) 4,4',4'',4''',-Tetrasulfophthalocynine The compound was prepared using similar mole ratios of the reactant except 0.0048 mol of manganese acetate and purified as described for Tetrasodium salt of Cobalt(II)4,4',4'',4''',-Tetrasulfophthalocynine.

Experiment 37
Tetrasodium salt of iron(III) 4,4',4'',4''',-Tetrasulfophthalocynine oxygen adduct The compound was prepared using similar mole ratios of the reactant except 0.0048 mol of Fe (III) chloride and purified as described for Tetrasodium salt of Cobalt (II) 4,4',4'',4''',-Tetrasulfophthalocynine.

Experiment 38
Water soluble cobalt II complex N,N'-ethylenebis (salycyldiamine 5-sodium sulfonate) Synthesis of this comples was performed according to Kevin et al. J. Chem. Soc., Dalton Trans. 1982, 109.

N-phenyl salicyldimine (35 g.) was added to concentrated sulfuric acid 95 cm$^3$ and mixture was heated for two hours, with occasional stirring while keeping temperature in the range of 100+-5° C. and after cooling solution was slowly poured over ice water to obtain yellow precipitate which was subsequently recrystallized from water to obtain crystalline yellow compound (20 g).

25.5 g of above product was dissolved in 500 ml water and to this solution 8.4 g. anhydrous sodium carbonate was slowly added and stirred until effervescence ceased aniline was steam distilled aqueous solution was vacuum dried to obtain a solid which was purified by precipitation from water and ethanol.

$Na_2[Co(SO_3sal)]. 3 H_2O$

The compound $CoCl_2. 6H_2O$ (6 g. 25 mmol) was dissolved in 30 cc ater and added to a solution of disodium salicsyldehyde 5 sulfonic acid (13.2 g 50 mmol) in 20 cc water and mixture was heated for 10 min. After filtration solution was concentrated and cooled to obtain 12 g of crystalline complex.

N,N'-ethylenebis (salycyldiamine 5-sodium sulfonate)

Ethanol 100 cc water 15 cc and ethylene diamine (0.6 g. 10 mmol) were added to $Na_2[Co(SO_3sal)]_2. 3 H_2O$ (5.5 g. 10 mmol and mixture was refluxed under nitrogen atmosphere for 1 hr. dark brown feathery precipitate was recovered

Experiment 39
Preparation of supports for catalyst preparation

All support materials were sourced from commercial suppliers and were used without further size reduction. Specifications of supports are provided with appropriate specifications. Support materials were extracted with hexane, ether methanol and water using assembly described in FIG. 2.

Surface saturation with group IIA ions

Each support was divided in to a lot of 25 g and suspended in 500 ml solution of 5% barium nitrate solution. The suspension was refluxed for 24 hours. Suspension was brought to room temperature and solid were filtered and transferred to extractor described in FIG. 2 and extracted with 500 ml of water, acetone and petroleum ether (bp 60–80° C.) solids were vacuum dried and stored for further use.

Degassing supports as described above were degassed immediately before use by following procedure. Required amount was transferred to round bottomed flask equipped with two-way valve and evacuated at 0.1 mm Hg and temperature was raised to 150° C. and kept at this temperature for 1 hour at this temperature while maintaining vacuum. Vacuum inlet was closed and argon was introduced and flask was cooled to room temperature. The procedure was repeated at least thrice and solid was stored under argon for further use.

Following supports were prepared accordingly, silica, gamma alumina, zirconia, titania, keisulghur, bentonite, hyflosupercel, asbestos powder, magnesium hydrotalcite, barium sulfate, charcoal, bone ash.

Example 1 to 84
Preparation of catalytic formulation by co-precipitation

The following examples illustrate one of the procedures for the preparation of the catalytic formulation of the invention in accordance with the method of formulation known as co precipitation in bulk liquid.

The general procedure for the preparation of heterogeneous catalytic formulation is described herein as making of a solution of anionically charged catalytic entity, catalytically inert anionic additive (termed as solution A) and solution of group II A metal ions (termed as solution B). A support pretreated as described in earlier is suspended in aqueous or water miscible solvent and resulting suspension is vigorously agitated to this suspension solution A and solution B were added over a prolonged period of time and resulting suspension is further agitated for specified time. Suspension was centrifuged and solids were repeatedly washed with water, methanol and diethyl ether followed by drying in vacuum. Dry powder was stored under argon in gas tight vessel and can be used for appropriate reaction depending upon catalytically active entity incorporated in it.

Note 1: solution A is prepared by dissolving anionic components including anionic complex and additives to make homogeneous solution in degassed solvents. The resulting solution is also degassed by purging argon.

Note 2: solution B is prepared by dissolving dissolving group IIA metal salts. Solution was degassed prior to use.

Note 3 addition of A and B is carried out at ambient temperature unless stated.

| Example | Solution A | Solution B | Procedure |
|---|---|---|---|
| 1 | HRhCO(TPPTS)3, 50 mg, TPPTS 200 mg. Dissolved in water 2 ml | Saturated barium nitrate in water 2 ml | A suspension of 2 gm Davisil in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder. |

-continued

| Example | Solution A | Solution B | Procedure |
|---|---|---|---|
| 2 | HRhCO(TPPTS) 3, 50 mg, TPPTS 200 mg. Dissolved in water 2 ml | Saturated strontium chloride in water 2 ml | Solution A and solution B were added to a suspension of 2 gm Davisil in 10 ml water and resulting suspension is vigorously agitated to this suspension solution A and solution B were added simultaneously over a 3 hours in 50 μl portions resulting suspension is further agitated for 10 hours to yield pale yellow colored solid powder. |
| 3 | HRhCO(TPPTS)3, 50 mg, TPPTS 200 mg. Dissolved in water 2 ml | 500 mg of calcium chloride in 2 ml water | Solution A and solution B were added to a suspension of 5 gm Davisil in 10 ml water and resulting suspension is vigorously agitated to this suspension solution A and solution B were added simultaneously over a 3 hours in 50 μl portions resulting suspension is further agitated for 10 hours to yield pale yellow colored solid powder. |
| 4 | HRhCO(TPPTS)3 50 mg, TPPTS 200 mg. Dissolved in water 2 ml | Barium nitrate saturated solution in water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield pale yellow colored solid powder |
| 5 | HRhCO(TPPTS)3, 50 mg, TPPTS 200 mg. Dissolved in water 2 ml | Strontium chloride saturated solution in water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield pale yellow color solid powder |
| 6 | HRhCO(TPPTS)3 50 mg, TPPTS 200 mg. Dissolved in water 2 ml | Calcium chloride 500 mg solution in 2 ml water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield pale yellow color solid powder |
| 7 | HRhCO(TPPTS)3, 50 mg, TPPTS 200 mg. Dissolved in water 2 ml | Barium nitrate saturated solution in water | Solution A and solution B were added to a suspension of 2 gm bentonite in 10 ml water and resulting suspension is vigorously agitated to this suspension solution A and solution B were added simultaneously over a 3 hours in 50 μl portions resulting suspension is further agitated for 10 hours to yield pale yellow colored solid powder |
| 8 | HRhCO(TPPTS)3, 50 mg, TPPTS 200 mg. Dissolved in water 2 ml | Strontium chloride saturated solution in water | Solution A and solution B were added to a suspension of 2 gm bentonite in 10 ml water and resulting suspension is vigorously agitated to this suspension solution A and solution B were added simultaneously over a 3 hours in 50 μl portions resulting suspension is further agitated for 10 hours to yield pale yellow color solid powder |
| 9 | HRhCO(TPPTS)3, 50 mg, TPPTS 200 mg. Dissolved in water 2 ml | Calcium chloride 500 mg solution in 2 ml water | Solution A and solution B were added to a suspension of 2 gm bentonite in 10 ml water and resulting suspension is vigorously agitated to this suspension solution A and solution B were added simultaneously over a 3 hours in 50 μl portions resulting suspension is further agitated for 10 hours to yield pale yellow color solid powder |
| 10 | HRhCO(TPPTS)3, 50 mg, TPPTS 200 mg. Dissolved in water 2 ml | Barium nitrate saturated solution in water | Solution A and solution B were added to a suspension of 2 gm charcoal in 10 ml water and resulting suspension is vigorously agitated to this suspension solution A and solution B were added simultaneously over a 3 hours in 50 μl portions resulting suspension is further agitated for 2 hours to yield black colored solid powder |
| 11 | HRhCO(TPPTS)3, 50 mg, TPPTS 200 mg. Dissolved in water 2 ml | Strontium chloride saturated solution in water | Solution A and solution B were added to a suspension of 2 gm charcoal in 10 ml water and resulting suspension is vigorously agitated to this suspension solution A and solution B were added simultaneously over a 3 hours in 50 μl portions resulting suspension is further agitated for 2 hours to yield black colored solid powder. |
| 12 | HRhCO(TPPTS)3, 50 mg, TPPTS 200 mg. Dissolved in 2 ml water | Calcium chloride 500 mg solution in 2 ml water | Solution A and solution B were added to a suspension of 2 gm charcoal in 10 ml water and resulting suspension is vigorously agitated to this suspension solution A and solution B were added simultaneously over a 3 hours in 50 μl portions resulting suspension is further agitated for 2 hours to yield black colored solid powder |

-continued

| Example | Solution A | Solution B | Procedure |
|---|---|---|---|
| 13 | Ru(H)(Cl)(TPPTS)$_3$ 50 mg<br>TPPTS 200 mg<br>Dissolved in 2 ml water | Barium nitrate<br>saturated solution in<br>2 ml water | Solution A and solution B were added to a suspension of 2 gm Davisil in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 14 | Ru(H)(Cl)(TPPTS)$_3$ 50 mg<br>TPPTS 200 mg<br>Dissolved in 2 ml water. | Strontium chloride<br>saturated solution in<br>2 ml water | Solution A and solution B were added to a suspension of 2 gm Davisil in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 15 | Ru(H)(Cl)(TPPTS)$_3$ 50 mg<br>TPPTS 200 mg Dissolved in<br>2 ml water | Barium nitrate<br>saturated solution in<br>2 ml water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 16 | Ru(H)(Cl)(TPPTS)$_3$ 50 mg<br>TPPTS 200 mg Dissolved in<br>2 ml water | Strontium chloride<br>saturated solution in<br>2 ml water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 17 | Ru(H)(Cl)(TPPTS)$_3$ 50 mg<br>TPPTS 200 mg<br>Sodium polyvinylsulfonate<br>500 mg Dissolved in 2 ml<br>water | Strontium chloride<br>saturated solution in<br>2 ml water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 18 | Ru (H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | Solution A and solution B were added to a suspension of 2 gm γ-alumina in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 19 | Ru (H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | Solution A and solution B were added to a suspension of 2 gm titania in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 20 | Ru (H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | Solution A and solution B were added to a suspension of 2 gm zirconia in 10 ml water and resulting suspension is vigorously agitated to this suspension solution A and solution B were added simultaneously over a 3 hours in 50 μl portions resulting suspension is further agitated for 10 hours to yield light brown colored solid powder. |
| 21 | Ru (H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | Solution A and solution B were added to a suspension of 2 gm activated charcoal in 10 ml water and resulting suspension is vigorously agitated to this suspension solution A and solution B were added simultaneously over a 3 hours in 50 μl portions resulting suspension is further agitated for 10 hours to yield black colored solid powder. |
| 22 | PdCl$_2$ (TPPTS)$_2$ 10 mg<br>TPPTS 100 mg<br>Poly acrylic acid sodium salt<br>in 5 ml | Barium nitrate<br>saturated solution 5<br>ml | Solution A and solution B were added to a suspension of 2 gm shredded asbestos rope in 20 ml water and resulting suspension is vigorously agitated to this suspension solution A and solution B was added s over a period of 3 hours in 50 μl portions resulting suspension is further agitated for 10 hours to yield yellow gray colored solid powder. |
| 23 | PdCl$_2$ (TPPTS)$_2$ 10 mg<br>TPPTS 100 mg<br>Poly acrylic acid sodium salt<br>in 5 ml | Strontium chloride<br>saturated solution 5<br>ml | Solution A and solution B were added to a suspension of 2 gm shredded asbestos rope in 20 ml water and resulting suspension is vigorously agitated to this suspension solution A and solution B was added over a 3 hours in 50 μl portions resulting suspension is further agitated for 10 hours to yield yellow gray colored solid powder. |

-continued

| Example | Solution A | Solution B | Procedure |
|---|---|---|---|
| 24 | PdCl$_2$ (TPPTS)$_2$ 10 mg<br>TPPTS 100 mg<br>Poly acrylic acid sodium salt in 5 ml | 500 mg calcium chloride in 5 ml water. | Solution A and solution B were added to a suspension of 2 gm shredded asbestos rope in 20 ml water and resulting suspension is vigorously agitated to this suspension solution A and solution B was added over a 3 hours in 50 μl portions resulting suspension is further agitated for 10 hours to yield yellow gray colored solid powder. |
| 25 | PdAc$_2$BYPYDS 25 mg<br>BYPYDS 100 mg<br>Dissolved in 2 ml water | Barium nitrate saturated solution 5 ml | Solution A and solution B were added to a suspension of 2 gm davisil in 20 ml water and resulting suspension is vigorously agitated to this suspension solution A and solution B was added over a 3 hours in 50 μl portions resulting suspension is further agitated for 10 hours to yield pale orange colored solid powder. |
| 26 | PdAc$_2$BYPYDS 25 mg<br>BYPYDS 100 mg<br>Dissolved in 2 ml water | Strontium chloride saturated solution 5 ml | Solution A and solution B were added to a suspension of 2 gm davisil in 20 ml water and resulting suspension is vigorously agitated to this suspension solution A and solution B was added over a 3 hours in 50 μl portions resulting suspension is further agitated for 10 hours to yield pale orange colored colored solid powder. |
| 27 | PdAc$_2$BYPYDS 25 mg<br>BYPYDS 100 mg<br>Dissolved in 2 ml water | 500 mg calcium chloride in 5 ml water | Solution A and solution B were added to a suspension of 2 gm davisil in 20 ml water and resulting suspension is vigorously agitated to this suspension solution A and solution B was added over a 3 hours in 50 μl portions resulting suspension is further agitated for 10 hours to yield pale orange colored solid powder. |
| 28 | PdAc$_2$BYPYDS 25 mg<br>BYPYDS 100 mg<br>Dissolved in 2 ml water | Barium nitrate saturated solution 5 ml | Solution A and solution B were added to a suspension of 2 gm bentonite in 20 ml water and resulting suspension is vigorously agitated to this suspension solution A and solution B was added over a 3 hours in 50 μl portions resulting suspension is further agitated for 10 hours to yield light orange colored solid powder. |
| 29 | PdAc$_2$ tri (o) tolyl phosphine trisulfonated 25 mg<br>Tri (o) tolyl phosphine trisulfonated 100 mg<br>Dissolved in 2 ml water | Barium nitrate saturated solution 5 ml | Solution A and solution B were added to a suspension of 2 gm bentonite in 20 ml water and resulting suspension is vigorously agitated to this suspension, solution A and solution B was added over a 3 hours in 50 μl portions resulting suspension is further agitated for 10 hours to yield pale yellow ocher colored solid powder. |
| 30 | PdAc$_2$ tri (o) tolyl phosphine trisulfonated 25 mg<br>Tri (o) tolyl phosphine trisulfonated 100 mg<br>Dissolved in 2 ml water | Strontium chloride saturated solution 5 ml | Solution A and solution B were added to a suspension of 2 gm bentonite in 20 ml water and resulting suspension is vigorously agitated to this suspension solution A and solution B was added over a 3 hours in 50 μl portions resulting suspension is further agitated for 10 hours to yield pale yellow ocher colored solid powder. |
| 31 | PdAc$_2$ trio tolyl phosphine trisulfonated 25 mg<br>Tri ortho tolyl phosphine trisulfonated 100 mg<br>Dissolved in 2 ml water | Barium nitrate saturated solution 5 ml | Solution A and solution B were added to a suspension of 2 gm alumina in 20 ml water and resulting suspension is vigorously agitated to this suspension solution A and solution B was added over a 3 hours in 50 μl portions resulting suspension is further agitated for 10 hours to yield pale yellow ocher colored solid powder. |
| 32 | PdAc$_2$ tri ortho tolyl phosphine trisulfonated 25 mg<br>Tri ortho tolyl phosphine trisulfonated 100 mg<br>Dissolved in 2 ml water | Barium nitrate saturated solution 5 ml | Solution A and solution B were added to a suspension of 2 gm charcoal in 20 ml water and resulting suspension is vigorously agitated to this suspension solution A and solution B was added over a 3 hours in 50 μl portions resulting suspension is further agitated for 10 hours to yield black colored solid powder. |
| 33 | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | A suspension of 1 gm davisil in 5 ml water was formed and resulting suspension was vigorously agitated to this suspension solution A and solution B were added simultaneously over a 3 hours in 50 μl portions resulting suspension is further agitated for 10 hours to yield solid powder almost white with blue tinge. |
| 34 | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | A suspension of 1 gm alumina in 5 ml water was formed and resulting suspension was vigorously agitated to this suspension solution A and solution B were added simultaneously over a 3 hours in 50 μl portions resulting suspension is further agitated for 10 hours to yield solid powder almost white with blue tinge. |

-continued

| Example | Solution A | Solution B | Procedure |
|---|---|---|---|
| 35 | NiCl$_2$.(TPPTS)$_2$ 25 mg<br>TPPTS 100 mg<br>Sodium carboxy methyl<br>cellulose 100 mg<br>Dissolved in 2 ml | Saturated barium<br>nitrate in 2 ml water | A suspension of 1 gm zirconia in 5 ml water was<br>formed and resulting suspension was vigorously<br>agitated to this suspension solution A and solution B<br>were added simultaneously over a 3 hours in 50 μl<br>portions resulting suspension is further agitated for 10<br>hours to yield solid powder almost white with blue<br>tinge. |
| 36 | NiCl$_2$.(TPPTS)$_2$ 25 mg<br>TPPTS 100 mg<br>Sodium carboxy methyl<br>cellulose 100 mg<br>Dissolved in 2 ml | Saturated strontium<br>chloride in 2 ml<br>water | A suspension of 1 gm zirconia in 5 ml water was<br>formed and resulting suspension was vigorously<br>agitated to this suspension solution A and solution B<br>were added simultaneously over a 3 hours in 50 μl<br>portions resulting suspension is further agitated for 10<br>hours to yield solid powder almost white with blue<br>tinge. |
| 37 | NiCl$_2$.(TPPTS)$_2$ 25 mg<br>TPPTS 100 mg<br>Sodium carboxy methyl<br>cellulose 100 mg<br>Dissolved in 2 ml | Saturated strontium<br>chloride in 2 ml<br>water | A suspension of 1 gm titania in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield solid powder almost white with blue tinge. |
| 38 | NiCl$_2$.(TPPTS)$_2$ 25 mg<br>TPPTS 100 mg<br>Sodium carboxy methyl<br>cellulose 100 mg<br>Dissolved in 2 ml | Saturated strontium<br>chloride in 2 ml<br>water | A suspension of 1 gm asbestos in 5 ml water was<br>formed and resulting suspension was vigorously<br>agitated to this suspension solution A and solution B<br>were added simultaneously over a 3 hours in 50 μl<br>portions resulting suspension is further agitated for 10<br>hours to yield gray colored solid powder. |
| 39 | (IrClCOD) 5 mg exchanged<br>with TPPTS 100 mg.<br>Poly acrylic acid sodium salt<br>100 mg<br>In 2 ml water | Saturated strontium<br>chloride in 2 ml<br>water | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |
| 40 | (IrClCOD) 5 mg exchanged<br>with TPPTS 100 mg.<br>Poly acrylic acid sodium salt<br>100 mg<br>In 2 ml water | Saturated strontium<br>chloride in 2 ml<br>water | A suspension of 1 gm keisulghur in 5 ml water was<br>formed and resulting suspension was vigorously<br>agitated to this suspension solution A and solution B<br>were added simultaneously over a 3 hours in 50 μl<br>portions resulting suspension is further agitated for 10<br>hours to yield pale yellow colored solid powder. |
| 41 | (IrClCOD) 5 mg exchanged<br>with TPPTS 100 mg.<br>Poly acrylic acid sodium salt<br>100 mg<br>In 2 ml water | Saturated strontium<br>chloride in 2 ml<br>water | A suspension of 1 gm bentonite in 5 ml water was<br>formed and resulting suspension was vigorously<br>agitated to this suspension solution A and solution B<br>were added simultaneously over a 3 hours in 50 μl<br>portions resulting suspension is further agitated for 10<br>hours to yield pale yellow colored solid powder. |
| 42 | (RuCl$_2$COD) 5 mg exchanged<br>with diphenyl phosphino<br>ethane tetrasulfonate 100 mg.<br>Poly acrylic acid sodium salt<br>100 mg<br>In 2 ml water | Saturated strontium<br>chloride in 2 ml<br>water | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |
| 43 | (RuCl$_2$COD) 5 mg exchanged<br>with diphenyl phosphino<br>ethane tetrasulfonate 100 mg.<br>Poly acrylic acid sodium salt<br>100 mg<br>In 2 ml water | Saturated strontium<br>chloride in 2 ml<br>water | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |
| 44 | (RuCl$_2$COD) 5 mg exchanged<br>with diphenyl phosphino<br>ethane tetrasulfonate 100 mg.<br>Poly acrylic acid sodium salt<br>100 mg<br>In 2 ml water | 500 mg calcium<br>chloride in 2 ml<br>water | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |
| 45 | Rh(COD)PF$_6$/S,S chiraphos<br>tetrasulfonate 25 mg<br>S,S chiraphos tetrasulfonate<br>25 mg<br>Sodium alginate 100 mg<br>dissolved in 2 ml water | Saturated strontium<br>chloride solution 2<br>ml | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |
| 46 | Rh(COD)PF$_6$/S,S chiraphos<br>tetrasulfonate 25 mg<br>S,S chiraphos tetrasulfonate<br>25 mg<br>Sodium alginate 100 mg<br>dissolved in 2 ml water | Saturated barium<br>nitrate solution 2 ml | A suspension of 1 gm davisil in 5 ml water was formed<br>and resulting suspension was vigorously agitated to this<br>suspension solution A and solution B were added<br>simultaneously over a 3 hours in 50 μl portions<br>resulting suspension is further agitated for 10 hours to<br>yield pale yellow colored solid powder. |

-continued

| Example | Solution A | Solution B | Procedure |
|---|---|---|---|
| 47 | Rh (COD) PF6/S,S chiraphos tetrasulfonate 25 mg S,S chiraphos tetrasulfonate 25 mg Sodium alginate 100 mg dissolved in 2 ml water | Saturated barium nitrate solution 2 ml | A suspension of 1 gm alumina in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 48 | Rh(COD)PF$_6$/S,S chiraphos tetrasulfonate 25 mg S,S chiraphos tetrasulfonate 25 mg Sodium alginate 100 mg dissolved in 2 ml water | Saturated barium nitrate solution 2 ml | A suspension of 1 gm titania in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 49 | HRhCO (TPATS)$_3$ 10 mg 100 mg TPATS Carboxy methyl cellulose sodium 100 mg in 1 ml water | 500 mg Calcium chloride solution in water 5 ml | A suspension of 1 gm titania in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 50 | HRhCO (TPATS)$_3$ 10 mg 100 mg TPATS carboxy methyl cellulose sodium 100 mg in 1 ml water | Strontium chloride saturated solution in water 5 ml | A suspension of 1 gm alumina in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 51 | HRhCO (TPATS)$_3$ 10 mg 100 mg TPATS carboxy methyl cellulose sodium 100 mg in 1 ml water | Barium nitrate saturated solution in water 5 ml | A suspension of 1 gm bentonite in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 52 | HRhCO (TPATS)$_3$ 10 mg 100 mg TPATS Carboxy methyl cellulose sodium 100 mg in 1 ml water | Strontium chloride saturated solution in water 5 ml | A suspension of 1 gm titania in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 53 | HRhCO (TPATS)$_3$ 10 mg 100 mg TPATS Carboxy methyl cellulose sodium 100 mg in 1 ml water | Strontium chloride saturated solution in water 5 ml | A suspension of 1 gm Davisil in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 54 | HRhCO(BISBIS) 50 mg BISBIS 200 mg 200 mg sodium sulfate Dissolved in 2 ml water | Saturated barium nitrate solution is 5 ml water | A suspension of 2 gm Davisil in 5 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 55 | HRhCO(BISBIS) 50 mg BISBIS 200 mg 200 mg polyvinyl sulfonic acid dissolved in 2 ml water | 1 g calcium chloride solution In 5 ml water | A suspension of 2 gm Davisil in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 56 | HRhCO(BISBIS) 50 mg BISBIS 200 mg 200 mg polyacrylic acid sodium salt dissolved in 2 ml water | Saturated barium nitrate solution is 5 ml water | A suspension of 2 gm titania in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder.7 |
| 57 | HRhCO(BISBIS) 50 mg BISBIS 200 mg 200 mg polyvinyl sulfonic acid dissolved in 2 ml water | Saturated strontium chloride solution is 5 ml water | A suspension of 2 gm alumina in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 58 | HRhCO(BISBIS) 50 mg BISBIS 200 mg 200 mg polyvinyl sulfonic acid dissolved in 2 ml water | Saturated barium nitrate solution is 5 ml water | A suspension of 2 gm bentonite in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder. |

-continued

| Example | Solution A | Solution B | Procedure |
|---|---|---|---|
| 59 | HRhCO(BISBIS) 50 mg<br>BISBIS 200 mg<br>200 mg polyvinyl sulfonic acid dissolved in 2 ml water | Saturated barium nitrate solution is 5 ml water | A suspension of 2 gm Davisil in 10 ml water was formed and resulting suspension was vigorously agitated to this suspension solution A and solution B were added simultaneously over a 3 hours in 50 μl portions resulting suspension is further agitated for 10 hours to yield pale yellow colored solid powder. |
| 60 | $PtCl_2(TPPTS)_2$ 50 mg<br>TPPTS 100 mg<br>100 mg sodium alginate dissolved in 2 ml water | Saturated solution of barium nitrate 5 ml | A suspension of 2 gm of davisil in 10 ml butane diol was formed and resulting suspension was vigorously agitated to this suspension solution A was added over a period of 2 hours and further agitated for 5 hours solution B was then added in portions of 50 μl over a period of 3 hours resulting suspension is further agitated for 24 hours to yield gray colored solid powder. |
| 61 | $PtCl_2(TPPTS)_2$ 50 mg<br>TPPTS 100 mg<br>100 mg oxalic acid sodium salt<br>Dissolved in 2 ml water | Saturated solution of barium nitrate 5 ml | A suspension of 2 gm of γ-alumina in 10 ml butane diol was formed and resulting suspension was vigorously agitated to this suspension solution A was added over a period of 2 hours and further agitated for 5 hours solution B was then added in portions of 50 μl over a period of 3 hours resulting suspension is further agitated for 24 hours to yield pale yellow colored solid powder. |
| 62 | $PtCl_2(TPPTS)_2$ 50 mg<br>TPPTS 100 mg<br>100 mg citric acid<br>Dissolved in 2 ml water | Saturated solution of strontium chloride 5 ml | A suspension of 2 gm of davisil in 10 ml ethylene glycol was formed and resulting suspension was vigorously agitated to this suspension solution A was added over a period of 2 hours and further agitated for 5 hours solution B was then added in portions of 50 μl over a period of 3 hours resulting suspension is further agitated for 24 hours to yield pale yellow colored solid powder. |
| 63 | $PtCl_2(TPPTS)_2$ 50 mg<br>TPPTS 100 mg<br>100 mg polyacrylic acid sodium salt<br>Dissolved in 2 ml water | Saturated solution of barium nitrate 5 ml | A suspension of 2 gm of davisil in 10 ml butane diol was formed and resulting suspension was vigorously agitated to this suspension solution A was added over a period of 2 hours and further agitated for 5 hours solution B was then added in portions of 50 μl over a period of 3 hours resulting suspension is further agitated for 24 hours to yield pale yellow colored solid powder. |
| 64 | $PtCl_2(TPPTS)_2$ 50 mg<br>TPPTS 300 mg<br>Dissolved in 2 ml water | Saturated solution of barium nitrate 5 ml | A suspension of 2 gm of shredded asbestos rope in 10 ml butane diol was formed and resulting suspension was vigorously agitated to this suspension solution A was added over a period of 2 hours and further agitated for 5 hours solution B was then added in portions of 50 μl over a period of 3 hours resulting suspension is further agitated for 24 hours to yield gray colored solid powder. |
| 65 | Cobalt N, N'ethylene bis (salicyldiamine) 5-sulfonato sodium 100 mg.<br>Sodium phosphate. 500 mg.<br>In 5 ml water | Saturated barium nitrate solution in water 5 ml | A suspension of 2 gm davisil in 10 ml tetrahydrofuran 50% in water was formed and resulting suspension was vigorously agitated to this suspension solution A and solution B were added at simultaneously in portions of 50 μl over a period of 3 hours resulting suspension is further agitated for 24 hours to yield pale brown colored solid powder. |
| 66 | Cobalt N, N'ethylene bis (salicyldiamine) 5-sulfonato sodium 100 mg.<br>Sodium silicate 500 mg.<br>In 5 ml water | Saturated barium nitrate solution in water 5 ml | A suspension of 2 gm alumina in 10 ml tetrahydrofuran 50% in water was formed and resulting suspension was vigorously agitated to this suspension solution A and solution B were added at simultaneously in portions of 50 μl over a period of 3 hours resulting suspension is further agitated for 24 hours to yield pale brown colored solid powder. |
| 67 | Cobalt N, N'ethylene bis (salicyldiamine) 5-sulfonato sodium 100 mg.<br>Polyvinyl sulfonate sodium. 500 mg.<br>In 5 ml water | Saturated barium nitrate solution in water 5 ml | A suspension of 2 gm titania in 10 ml tetrahydrofuran 50% in water was formed and resulting suspension was vigorously agitated to this suspension solution A and solution B were added at simultaneously in portions of 50 μl over a period of 3 hours resulting suspension is further agitated for 24 hours to yield pale brown colored solid powder. |
| 68 | Cobalt N, N'ethylene bis (salicyldiamine) 5-sulfonato sodium 100 mg.<br>Polyvinyl sulfonate sodium. 500 mg.<br>In 5 ml water | Saturated barium nitrate solution in water 5 ml | A suspension of 2 gm zirconia asbesto rope in 10 ml tetrahydrofuran 50% in water was formed and resulting suspension was vigorously agitated to this suspension solution A and solution B were added at simultaneously in portions of 50 μl over a period of 3 hours resulting suspension is further agitated for 24 hours to yield pale brown colored solid powder. |

-continued

| Example | Solution A | Solution B | Procedure |
|---|---|---|---|
| 69 | Cobalt N, N'ethylene bis (salicyldiamine) 5-sulfonato sodium 100 mg. Polyvinyl sulfonate sodium. 500 mg. In 5 ml water | 2 g calcium chloride solution in water 5 ml | A suspension of 2 gm shredded asbesto rope in 10 ml tetrahydrofuran 50% in water was formed and resulting suspension was vigorously agitated to this suspension solution A and solution B were added at simultaneously in portions of 50 µl over a period of 3 hours resulting suspension is further agitated for 24 hours to yield pale brown colored solid powder. |
| 70 | Cobalt (II), 4, 4', 4", 4'"-tetrasulfopthalocynine oxygen adduct. 500 mg. And 500 mg sodium sodium poly vinyl sulfonate in 5 ml water | Saturated strontium chloride in 5 ml water | A suspension of 2 gm shredded asbesto rope in 10 ml methanol was formed and resulting suspension was vigorously agitated to this suspension solution A was added and stirred for 15 min and solution B was added at once resulting suspension is further agitated for 3 hours to yield steel gray colored solid powder. |
| 71 | Cobalt (II), 4, 4', 4", 4'"-tetrasulfopthalocynine. 500 mg And 500 mg sodium phosphate in 5 ml water | Saturated barium nitrate in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 72 | Cobalt (II), 4, 4', 4", 4'"-tetrasulfopthalocynine . 500 mg And 500 mg sodium phosphate in 5 ml water | Saturated strontium chloride in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 73 | Cobalt (II), 4, 4', 4", 4'"-tetrasulfopthalocynine. 500 mg And 500 mg sodium phosphate in 5 ml water | 500 mg. $CaCl_2$ in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 74 | Copper (II), 4, 4', 4", 4'"-tetrasulfopthalocynine. 500 mg And 500 mg sodium sulfate in 5 ml water | 500 mg. $CaCl_2$ in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 75 | Copper (II), 4, 4', 4", 4'"-tetrasulfopthalocynine. 500 mg And 500 mg sodium silicate in 5 ml water | Saturated strontium chloride in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 76 | Copper (II), 4, 4', 4", 4'"-tetrasulfopthalocynine. 500 mg And 500 mg sodium silicate in 5 ml water | Saturated barium nitrate in 5 ml water | A suspension of 2 gm keisulghur in 10 ml methanol was formed and resulting suspension was vigorously agitated to this suspension solution A was added and stirred for 15 min and solution B was added at once resulting suspension is further agitated for 3 hours to yield light blue colored solid powder. |
| 77 | Copper (II), 4, 4', 4", 4'"-tetrasulfopthalocynine . 500 mg And 500 mg sodium silicate in 5 ml water | Saturated barium nitrate in 5 ml water | A suspension of 2 gm bentonite in 10 ml methanol was formed and resulting suspension was vigorously agitated to this suspension solution A was added and stirred for 15 min and solution B was added at once resulting suspension is further agitated for 3 hours to yield light blue colored solid powder. |
| 78 | Copper (II), 4, 4', 4", 4'"-tetrasulfopthalocynine. 500 mg And 500 mg sodium silicate in 5 ml water | Saturated strontiun chloride in 5 ml water | A suspension of 2 gm bentonite in 10 ml methanol was formed and resulting suspension was vigorously agitated to this suspension solution A was added and stirred for 15 min and solution B was added at once resulting suspension is further agitated for 3 hours to yield light blue colored solid powder. |
| 79 | Manganese(II), 4, 4', 4", 4'"-tetrasulfopthalocynine. 500 mg And 500 mg sodium silicate in 5 ml water | Saturated strontiun chloride in 5 ml water | A suspension of 2 gm Davisil in 10 ml methanol was formed and resulting suspension was vigorously agitated to this suspension solution A was added and stirred for 15 min and solution B was added at once resulting suspension is further agitated for 3 hours to yield light blue colored solid powder. |
| 80 | Manganese(II), 4, 4', 4", 4'"-tetrasulfopthalocynine. 500 mg And 500 mg sodium silicate in 5 ml water | Saturated barium nitrate in 5 ml water | A suspension of 2 gm Davisil in 10 ml methanol was formed and resulting suspension was vigorously agitated to this suspension solution A was added and stirred for 15 min and solution B was added at once resulting suspension is further agitated for 3 hours to yield light blue colored solid powder. |

-continued

| Example | Solution A | Solution B | Procedure |
|---|---|---|---|
| 81 | Manganese(II), 4, 4', 4'', 4'''-tetrasulfopthalocynine. 500 mg And 500 mg sodium silicate in 5 ml water | Saturated barium nitrate in 5 ml water | A suspension of 2 gm γ-alumina in 10 ml methanol was formed and resulting suspension was vigorously agitated to this suspension solution A was added and stirred for 15 min and solution B was added at once resulting suspension is further agitated for 3 hours to yield light blue colored solid powder. |
| 82 | Manganese(II), 4, 4', 4'', 4'''-tetrasulfopthalocynine 500 mg And 500 mg sodium polyvinyl sulfonate in 5 ml water | Saturated barium nitrate in 5 ml water | A suspension of 2 gm γ-alumina in 10 ml methanol was formed and resulting suspension was vigorously agitated to this suspension solution A was added and stirred for 15 min and solution B was added at once resulting suspension is further agitated for 3 hours to yield light blue colored solid powder. |
| 83 | Iron (III), 4, 4', 4'', 4'''-tetrasulfopthalocynine oxygen adduct. 500 mg And 500 mg sodium sulfate in 5 ml water | Saturated strontium chloride in 5 ml water | A suspension of 2 gm Davisil in 10 ml methanol was formed and resulting suspension was vigorously agitated to this suspension solution A was added and stirred for 15 min and solution B was added at once resulting suspension is further agitated for 3 hours to yield light blue colored solid powder. |
| 84 | Iron (III), 4, 4', 4'', 4'''-tetrasulfopthalocynine oxygen adduct. 500 mg And 500 mg sodium sulfate in 5 ml water | Saturated barium nitrate in water 5 ml | A suspension of 2 gm Davisil in 10 ml methanol was formed and resulting suspension was vigorously agitated to this suspension solution A was added and stirred for 15 min and solution B was added at once resulting suspension is further agitated for 3 hours to yield light blue colored solid powder. |

Note 1: solution A is prepared by dissolving anionic components including anionic complex and additives to make homogeneous solution in degassed solvents. The resulting solution is also degassed by purging argon.
Note 2: solution B is prepared by dissolving dissolving group IIA metal salts. Solution was degassed prior to use.
Note 3 addition of A and B is carried out at ambient temperature unless stated.

Examples 85 to 168
Preparation of catalytic formulation by deposition precipitation The following examples illustrate one of the procedures for the preparation of the catalytic formulation of the invention in accordance with the method of formulation known as co precipitation near the surface of the solid support.

The general procedure for the preparation of heterogeneous catalytic formulation is described herein as making of a solution of anionically charged catalytic entity, catalytically inert anionic additive (termed as solution A) and solution of group II A metal ions (termed as solution B). The specified amount of support pretreated as described in earlier is impregnated with solution A by wetting solids with solution followed by evaporation to obtain dry solid support bearing anionic components of solution A. This solid powder is gradually added to the solution B over a specified period of time. Restating Suspension is further agitated for specified titre. Suspension was centrifuged and solids were repeatedly washed with water and dried in vacuum. Dry powder was stored under argon in gas tight vessel These solid catalytic formulations can be used for appropriate reactions depending upon catalytically active entity incorporated in it.

Note 1: solution A is prepared by dissolving anionic components including anionic complex and additives to make homogeneous solution in degassed solvents. And resulting solution is also degassed by purging argon.

Note 2: solution B is prepared by dissolving dissolving group IIA metal salts. Solution was degassed prior to use Note 3: the impregnation of solution on solid support is carried out by wetting solids with solution A and evaporating in vacuum at 50° C. unless stated Note 4: addition of impregnated solids with components of A to solution B is carried out at ambient temperature unless stated.

| Example | Solution A | Solution B | Procedure |
|---|---|---|---|
| 85. | HRhCO(TPPTS)$_3$ 50 mg, TPPTS 200 mg. Dissolved in water 2 ml | Saturated barium nitrate in water 2 ml | 2 gm Davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 86. | HRhCO(TPPTS)$_3$ 50 mg, TPPTS 200 mg. Dissolved in water 2 ml | Saturated strontium chloride in water 2 ml | 2 gm Davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |

-continued

| Example | Solution A | Solution B | Procedure |
|---|---|---|---|
| 87. | HRhCO(TPPTS)3, 50 mg, TPPTS 200 mg. Dissolved in water 2 ml | 500 mg of calcium chloride in 2 ml water | 2 gm Davisil was wetted, with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 88. | HRhCO(TPPTS)3, 50 mg, TPPTS 200 mg. Dissolved in water 2 ml | Barium nitrate saturated solution in water | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 89. | HRhCO(TPPTS)3, 50 mg, TPPTS 200 mg. Dissolved in water 2 ml | Strontium chloride saturated solution in water 2 ml | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 90. | HRhCO(TPPTS)3, 50 mg, TPPTS 200 mg. Dissolved in water 2 ml | Calcium chloride 500 mg solution in 2 ml water | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours, filtered to yield pale yellow colored solid powder. |
| 91. | HRhCO(TPPTS)3, 50 mg, TPPTS 200 mg. Dissolved in water 2 ml | Barium nitrate saturated solution in water 2 ml | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 92. | HRhCO(TPPTS)3, 50 mg, TPPTS 200 mg. Dissolved in water 2 ml | Strontium chloride saturated solution in water | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 93. | HRhCO(TPPTS)3, 50 mg, TPPTS 200 mg. Dissolved in water 2 ml | Calcium chloride 500 mg solution in 2 ml water | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield pale yellow colored solid powder. |
| 94. | HRhCO(TPPTS)3, 50 mg, TPPTS 200 mg. Dissolved in water 2 ml | Barium nitrate saturated solution in water | 2 gm charcoal was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield black colored solid powder. |
| 95. | HRhCO(TPPTS)3, 50 mg, TPPTS 200 mg. Dissolved in water 2 ml | Strontium chloride saturated solution in water | 2 gm charcoal was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield black colored solid powder. |

-continued

| Example | Solution A | Solution B | Procedure |
|---|---|---|---|
| 96. | HRhCO(TPPTS)3, 50 mg, TPPTS 200 mg. Dissolved in 2 ml water | Calcium chloride 500 mg solution in 2 ml water | 2 gm charcoal was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours to yield black colored solid powder. |
| 97. | Ru(H)(Cl)(TPPTS)$_3$ 50 mg TPPTS 200 mg Dissolved in 2 ml water | Barium nitrate saturated solution in 2 ml water | 2 gm Davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder.. |
| 98. | Ru(H)(Cl)(TPPTS)$_3$ 50 mg TPPTS 200 mg Dissolved in 2 ml water. | Strontium chloride saturated solution in 2 ml water | 2 gm Davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder. |
| 99. | Ru(H)(Cl)(TPPTS)$_3$ 50 mg TPPTS 200 mg Dissolved in 2 ml water | Barium nitrate saturated solution in 2 ml water | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder. |
| 100. | Ru(H)(Cl)(TPPTS)$_3$ 50 mg TPPTS 200 mg Dissolved in 2 ml water | Strontium chloride saturated solution in 2 ml water | 2 gm γ-alumina was wetted with 100 in portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder. |
| 101. | Ru(H)(Cl)(TPPTS)$_3$ 50 mg TPPTS 200 mg Sodium polyvinylsulfonate 500 mg Dissolved in 2 ml water | Strontium chloride saturated solution in 2 ml water | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder. |
| 102. | Ru(H)(Cl)(TPPTS)$_3$ 50 mg TPPTS 200 mg Sodium polyvinylsulfonate 500 mg Dissolved in 2 ml water | Barium nitrate saturated solution in 2 ml water | 2 gm γ-alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder.. |
| 103. | Ru(H)(Cl)(TPPTS)$_3$ 50 mg TPPTS 200 mg Sodium polyvinylsulfonate 500 mg Dissolved in 2 ml water | Barium nitrate saturated solution in 2 ml water | 2 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light brown colored solid powder. |
| 104. | Ru(H)(Cl)(TPPTS)$_3$ 50 mg TPPTS 200 mg Sodium polyvinylsulfonate 500 mg Dissolved in 2 ml water | Barium nitrate saturated solution in 2 ml water | 2 gm zirconia was wetted with 100 μl portion of solution A and evaporated under vaccuum 10 mm Hg with simultaneous tumbling remitting solution A was added in 100 μl fractions and solid was isolated (moisture content ~20%) this powder was added to solution B in equal fractions over a period of 2 hours and suspension was further agitated for 10 hours filtered to yield light brown colored solid powder.. |

-continued

| Example | Solution A | Solution B | Procedure |
|---|---|---|---|
| 105. | Ru(H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | 2 gm activated charcoal was wetted with 100 μl portion of solution A and evaporated under vaccuum 10 mm Hg with simultaneous tumbling remitting solution A was added in 100 μl fractions and solid was isolated (moisture content ~20%) this powder was added to solution B in equal fractions over a period of 2 hours and suspension was further agitated for 10 hours filtered to yield black colored solid powder. |
| 106. | PdCl$_2$(TPPTS)$_2$ 10 mg<br>TPPTS 100 mg<br>Poly acrylic acid sodium salt<br>in 5 ml | Barium nitrate<br>saturated solution 5<br>ml | 2 gm shredded asbestos rope was wetted with 100 μl portion of solution A and evaporated under vaccuum 10 mm Hg with simultaneous tumbling remitting solution A was added in 100 μl fractions and solid was isolated (moisture content ~20%) this powder was added to solution B in equal fractions over a period of 2 hours and suspension was further agitated for 10 hours filtered to yield yellow gray colored solid powder. |
| 107. | PdCl$_2$(TPPTS)$_2$ 10 mg<br>TPPTS 100 mg<br>Poly acrylic acid sodium salt<br>in 5 ml | Strontium chloride<br>saturated solution 5<br>ml | 2 gm shredded asbestos rope was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield yellow gray colored solid powder. |
| 108. | PdCl$_2$(TPPTS)$_2$ 10 mg<br>TPPTS 100 mg<br>Poly acrylic acid sodium salt<br>in 5 ml | 500 mg calcium<br>chloride in 5 ml<br>water. | 2 gm shredded asbestos rope was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield yellow gray colored solid powder. |
| 109. | PdAc$_2$BYPYDS 25 mg<br>BYPYDS 100 mg<br>Dissolved in 2 ml water | Barium nitrate<br>saturated solution<br>5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light orange colored solid powder. |
| 110. | PdAc$_2$BYPYDS 25 mg<br>BYPYDS 100 mg<br>Dissolved in 2 ml water | Strontium chloride<br>saturated solution<br>5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light orange colored solid powder. |
| 111. | PdAc$_2$BYPYDS 25 mg<br>BYPYDS 100 mg<br>Dissolved in 2 ml water | 500 mg calcium<br>chloride in 5 ml<br>water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light orange colored solid powder. |
| 112. | PdAc$_2$BYPYDS 25 mg<br>BYPYDS 100 mg<br>Dissolved in 2 ml water | Barium nitrate<br>saturated solution<br>5 ml | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield light orange colored solid powder. |
| 113. | PdAc$_2$ trio tolyl phosphine<br>trisulfonated 25 mg<br>trio tolyl phosphine<br>trisulfonated 100 mg<br>Dissolved in 2 ml water | Barium nitrate<br>saturated solution<br>5 ml | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale brown colored solid powder. |

-continued

| Example | Solution A | Solution B | Procedure |
|---|---|---|---|
| 114. | PdAc$_2$ trio tolyl phosphine trisulfonated 25 mg<br>trio tolyl phosphine trisulfonated 100 mg<br>Dissolved in 2 ml water | Strontium chloride saturated solution<br>5 ml | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale brown colored solid powder. |
| 115. | PdAc$_2$ trio tolyl phosphine trisulfonated 25 mg<br>trio tolyl phosphine trisulfonated 100 mg<br>Dissolved in 2 ml water | Barium nitrate saturated solution<br>5 ml | 2 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale brown colored solid powder. |
| 116. | PdAc$_2$ trio tolyl phosphine trisulfonated 25 mg<br>trio tolyl phosphine trisulfonated 100 mg<br>Dissolved in 2 ml water | Barium nitrate saturated solution<br>5 ml | 2 gm charcoal was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 24 hours filtered to yield black colored solid powder. |
| 117. | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 118. | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | 1 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 119. | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | 1 gm zirconia was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 120. | NiCl$_2$.(TPPTS)$_2$ 25 mg<br>TPPTS 100 mg<br>Sodium carboxy methyl cellulose 100 mg<br>Dissolved in 2 ml | Saturated strontium chloride in 2 ml water | 1 gm zirconia was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 121. | NiCl$_2$.(TPPTS)$_2$ 25 mg<br>TPPTS 100 mg<br>Sodium carboxy methyl cellulose 100 mg<br>Dissolved in 2 ml | Saturated strontium chloride in 2 ml water | 1 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 122. | NiCl$_2$.(TPPTS)$_2$ 25 mg<br>TPPTS 100 mg<br>Sodium carboxy methyl cellulose 100 mg<br>Dissolved in 2 ml | Saturated strontium chloride in 2 ml water | 1 gm asbestos was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |

-continued

| Example | Solution A | Solution B | Procedure |
|---|---|---|---|
| 123. | (IrClCOD) 5 mg exchanged with TPPTS 100 mg. Poly acrylic acid sodium salt 100 mg In 2 ml water | Saturated strontium chloride in 2 ml water | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 124. | (IrClCOD) 5 mg exchanged with TPPTS 100 mg. Poly acrylic acid sodium salt 100 mg In 2 ml water | Saturated strontium chloride in 2 ml water | 1 gm keisulghur was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 125. | (IrClCOD) 5 mg exchanged with TPPTS 100 mg. Poly acrylic acid sodium salt 100 mg In 2 ml water | Saturated strontium chloride in 2 ml water | 1 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 126. | (RuCl$_2$COD) 5 mg exchanged with diphenyl phosphino ethane tetrasulfonate 100 mg. Poly acrylic acid sodium salt 100 mg In 2 ml water | Saturated strontium chloride in 2 ml water | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 127. | (RuCl$_2$COD) 5 mg exchanged with diphenyl phosphino ethane tetrasulfonate 100 mg. Poly acrylic acid sodium salt 100 mg In 2 ml water | Saturated strontium chloride in 2 ml water | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 128. | (RuCl$_2$COD) 5 mg exchanged with diphenyl phosphino ethane tetrasulfonate 100 mg. Poly acrylic acid sodium salt 100 mg In 2 ml water | 500 mg calcium chloride in 2 ml water | 1 gm davisil was wetted with 100 μl portion of solution A and evaporated under vaccuum 10 mm Hg with simultaneous tumbling returning solution A was added in 100 μl fractions and solid was isolated (moisture content ~20%) this powder was added to solution B in equal fractions over a period of 2 hours and suspension was further agitated for 10 hours filtered to yield light brown-yellow colored solid powder. |
| 129. | Rh(COD)PF$_6$/S,S chiraphos tetrasulfonate 25 mg S,S chiraphos tetrasulfonate 25 mg Sodium alginate 100 mg dissolved in 2 ml water | Saturated strontium chloride solution 2 ml | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 130. | Rh(COD)PF$_6$/S,S chiraphos tetrasulfonate 25 mg S,S chiraphos tetrasulfonate 25 mg Sodium alginate 100 mg dissolved in 2 ml water | Saturated barium nitrate solution 2 ml | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 131. | Rh(COD)PF$_6$/S,S chiraphos tetrasulfonate 25 mg S,S chiraphos tetrasulfonate 25 mg Sodium alginate 100 mg dissolved in 2 ml water | Saturated barium nitrate solution 2 ml | 1 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |

-continued

| Example | Solution A | Solution B | Procedure |
|---|---|---|---|
| 132. | Rh(COD)PF$_6$/S,S chiraphos tetrasulfonate 25 mg<br>S,S chiraphos tetrasulfonate 25 mg<br>Sodium alginate 100 mg<br>dissolved in 2 ml water | Saturated barium nitrate solution 2 ml | 1 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 133. | HRhCO(TPATS)$_3$ 10 mg<br>100 mg TPATS<br>carboxy methyl cellulose sodium 100 mg in 1 ml water | 500 mg Calcium chloride solution in water 5 ml | 1 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 134. | HRhCO(TPATS)$_3$ 10 mg<br>100 mg TPATS<br>carboxy methyl cellulose sodium 100 mg in 1 ml water | Strontium chloride saturated solution in water 5 ml | 1 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 135. | HRhCO(TPATS)$_3$ 10 mg<br>100 mg TPATS<br>carboxy methyl cellulose sodium 100 mg in 1 ml water | Barium nitrate saturated solution in water 5 ml | 1 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 136. | HRhCO(TPATS)$_3$ 10 mg<br>100 mg TPATS<br>carboxy methyl cellulose sodium 100 mg in 1 ml water | Strontium chloride saturated solution in water 5 ml | 1 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 137. | HRhCO(TPATS)$_3$ 10 mg<br>100 mg TPATS<br>carboxy methyl cellulose sodium 100 mg in 1 ml water | Strontium chloride saturated solution in water 5 ml | 1 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 138. | HRhCO(BISBIS) 50 mg<br>BISBIS 200 mg<br>200 mg sodium sulfate dissolved in 2 ml water | Saturated barium nitrate solution is 5 ml water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 139. | HRhCO(BISBIS) 50 mg<br>BISBIS 200 mg<br>200 mg polyvinyl sulfonic acid<br>dissolved in 2 ml water | 1 g calcium chloride solution In 5 ml water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 140. | HRhCO(BISBIS) 50 mg<br>BISBIS 200 mg<br>200 mg polyacrylic acid sodium salt<br>dissolved in 2 ml water | Saturated barium nitrate solution is 5 ml water | 2 gm titania was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |

-continued

| Example | Solution A | Solution B | Procedure |
|---|---|---|---|
| 141. | HRhCO(BISBIS) 50 mg<br>BISBIS 200 mg<br>200 mg polyvinyl sulfonic acid<br>dissolved in 2 ml water | Saturated strontium chloride solution is 5 ml water | 2 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 142. | HRhCO(BISBIS) 50 mg<br>BISBIS 200 mg<br>200 mg polyvinyl sulfonic acid<br>dissolved in 2 ml water | Saturated barium nitrate solution is 5 ml water | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow colored solid powder. |
| 143. | HRhCO(BISBIS) 50 mg<br>BISBIS 200 mg<br>200 mg polyvinyl sulfonic acid<br>dissolved in 2 ml water | Saturated barium nitrate solution is 5 ml water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 144. | $PtCl_2(TPPTS)_2$ 50 mg<br>TPPTS 100 mg<br>100 mg sodium alginate<br>Dissolved in 2 ml water and 0.5 ml butane diol | Saturated solution of barium nitrate 5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 145. | $PtCl_2(TPPTS)_2$ 50 mg<br>TPPTS 100 mg<br>100 mg oxalic acid sodium salt<br>Dissolved in 2 ml water and 0.5 ml butane diol | Saturated solution of barium nitrate 5 ml | 2 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 146. | $PtCl_2(TPPTS)_2$ 50 mg<br>TPPTS 100 mg<br>100 mg citric acid<br>Dissolved in 2 ml water and 0.5 ml ethylene glycol | Saturated solution of strontium chloride 5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 147. | $PtCl_2(TPPTS)_2$ 50 mg<br>TPPTS 100 mg<br>100 mg polyacrylic acid sodium salt<br>Dissolved in 2 ml water and 0.5 ml butane diol | Saturated solution of barium nitrate 5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 148. | $PtCl_2(TPPTS)_2$ 50 mg<br>TPPTS 300 mg<br>Dissolved in 2 ml water | Saturated solution of barium nitrate 5 ml | 2 gm shredded asbestos rope was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale yellow-green colored solid powder. |
| 149. | Cobalt N, N'ethylene bis (salicyldiamine) 5-sulfonato sodium 100 mg.<br>Sodium phosphate. 500 mg.<br>In 5 ml water | Saturated barium nitrate solution in water 5 ml | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale brown colored solid powder. |

-continued

| Example | Solution A | Solution B | Procedure |
|---|---|---|---|
| 150. | Cobalt N, N'ethylene bis (salicyldiamine) 5-sulfonato sodium 100 mg. Sodium silicate 500 mg. In 5 ml water | Saturated barium nitrate solution in water 5 ml | 2 gm alumina was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale brown colored solid powder. |
| 151. | Cobalt N, N'ethylene bis (salicyldiamine) 5-sulfonato sodium 100 mg. Polyvinyl sulfonate sodium. 500 mg. In 5 ml water | Saturated barium nitrate solution in water 5 ml | 2 gm titania was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale brown colored solid powder. |
| 152. | Cobalt N, N'ethylene bis (salicyldiamine) 5-sulfonato sodium 100 mg. Polyvinyl sulfonate sodium. 500 mg. In 5 ml water | Saturated barium nitrate solution in water 5 ml | 2 gm zirconia was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale brown colored solid powder. |
| 153. | Cobalt N, N'ethylene bis (salicyldiamine) 5-sulfonato sodium 100 mg. Polyvinyl sulfonate sodium. 500 mg. In 5 ml water | 2 g calcium chloride solution in water 5 ml | 2 gm shreded asbestos rope was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield gray colored solid powder. |
| 154. | Cobalt (II), 4, 4', 4'', 4'''-tetrasulfopthalocynine. 500 mg And 500 mg sodium sodium poly vinyl sulfonate in 5 ml water | Saturated strontium chloride in 5 ml water | 2 gm shreded asbestos rope was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield blue-gray colored solid powder. |
| 155. | Cobalt (II), 4, 4' 4'', 4'''-tetrasulfopthalocynine. 500 mg And 500 mg sodium phosphate in 5 ml water | Saturated barium nitrate in 5 ml water | 2 gm kesilghur was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale blue colored solid powder. |
| 156. | Cobalt (II), 4, 4', 4'', 4'''-tetrasulfopthalocynine. 500 mg And 500 mg sodium phosphate in 5 ml water | Saturated strontium chloride in 5 ml water | 2 gm kesilghur was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale blue colored solid powder. |
| 157. | Cobalt (II), 4, 4', 4'', 4'''-tetrasulfopthalocynine. 500 mg And 500 mg sodium phosphate in 5 ml water | 500 mg. $CaCl_2$ in 5 ml water | 2 gm kesilghur was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale blue colored solid powder. |
| 158. | Copper (II), 4, 4', 4'', 4'''-tetrasulfopthalocynine. 500 mg And 500 mg sodium sulfate in 5 ml water | 500 mg. $CaCl_2$ in 5 ml water | 2 gm kesilghur was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale blue colored solid powder. |

-continued

| Example | Solution A | Solution B | Procedure |
|---|---|---|---|
| 159. | Copper (II), 4, 4', 4'', 4'''-tetrasulfopthalocynine. 500 mg And 500 mg sodium sulfate in 5 ml water | Saturated strontium chloride in 5 ml water | 2 gm kesilghur was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 160. | Copper (II), 4, 4', 4'', 4'''-tetrasulfopthalocynine. 500 mg And 500 mg sodium sulfate in 5 ml water | Saturated barium nitrate in 5 ml water | 2 gm kesilghur was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 161. | Copper (II), 4, 4', 4'', 4'''-tetrasulfopthalocynine. 500 mg And 500 mg sodium sulfate in 5 ml water | Saturated barium nitrate in 5 ml water | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 162. | Copper (II), 4, 4', 4'', 4'''-tetrasulfopthalocynine. 500 mg And 500 mg sodium sulfate in 5 ml water | Saturated strontium chloride in 5 ml water | 2 gm bentonite was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 163. | Manganese(II), 4, 4', 4'', 4'''-tetrasulfopthalocynine. 500 mg And 500 mg sodium silicate in 5 ml water | Saturated strontiun chloride in 5 ml water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 164. | Manganese(II), 4, 4', 4'', 4'''-tetrasulfopthalocynine. 500 mg And 500 mg sodium silicate in 5 ml water | Saturated barium nitrate in 5 ml water | 2 gm davisil was wetted with 100 μl portion of solution A and evaporated under vaccuum 10 mm Hg with simultaneous tumbling remitting solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 165. | Manganese(II), 4, 4', 4'', 4'''-tetrasulfopthalocynine. 500 mg And 500 mg sodium silicate in 5 ml water | Saturated barium nitrate in 5 ml water | 2 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 166. | Manganese(II), 4, 4', 4'', 4'''-tetrasulfopthalocynine. 500 mg And 500 mg sodium polyvinyl sulfonate in 5 ml water | Saturated barium nitrate in 5 ml water | 2 gm alumina was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |
| 167. | Iron (III), 4, 4', 4'', 4'''-tetrasulfopthalocynine oxygen adduct. 500 mg And 500 mg sodium sulfate in 5 ml water | Saturated strontium chloride in 5 ml water | 2 gm davisil was wetted with 100 μl portion of solution A and evaporated under vaccuum 10 mm Hg with simultaneous tumbling remaining solution A was added in 100 μl fractions and solid was isolated (moisture content ~20%) this powder was added to solution B in equal fractions over a period of 2 hours and suspension was further agitated for 10 hours filtered to yield pale blue colored solid powder. |

-continued

| Example | Solution A | Solution B | Procedure |
|---|---|---|---|
| 168. | Iron (III), 4, 4', 4'', 4'''-tetrasulfopthalocynine oxygen adduct. 500 mg And 500 mg sodium sulfate in 5 ml water | Saturated barium nitrate in water 5 ml | 2 gm davisil was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield pale blue colored solid powder. |

Note 1: solution A is prepared by dissolving anionic components including anionic complex and additives to make homogeneous solution in degassed solvents. And resulting solution is also degassed by purging argon.
Note 2: solution B is prepared by dissolving dissolving group IIA metal salts. Solution was degassed prior to use
Note 3: the impregnation of solution on solid support is carried out by wetting solids with solution A and evaporating in vacuum at 50° C. unless stated
Note 4: addition of impregnated solids with components of A to solution B is carried out at ambient temperature unless stated.

Examples 169 to 252

Preparation of catalytic formulation by deposition precipitation with simultaneous removal of water.

The following examples illustrate one of the procedures for the preparation of the catalytic formulation of the invention in accordance with the method of formulation known as co precipitation near the surface of the solid support.

The general procedure for the preparation of heterogeneous catalytic formulation is described herein as making of a solution of anionically charged catalytic entity, catalytically inert anionic additive (termed as solution A) and solution of group II A metal ions (termed as solution B). The specified amount of support pretreated as described in earlier is impregnated with solution A by wetting solids with solution followed by evaporation to obtain dry solid support bearing anionic components of solution A. This solid powder was suspended in water immiscible solvent or a solvent that forms azeotrope with solvent component of solution B, the suspension was agitated and temperature was raised such that solvent starts distilling. Under this condition solution B was slowly pumped in simultaneously solvent in which solids are suspended is also pumped in with rate similar to that of distillation. Once all solution B was added suspension was stirred for specified period of time. Resulting suspension is further agitated for specified time. Suspension was centrifuged and solids were repeatedly washed with water and dried in vacuum. Dry powder was stored under argon in gas tight vessel. These solid catalytic formulations can be used for appropriate reactions depending upon catalytically active entity incorporated in it.

Note 1: solution A is prepared by dissolving anionic components including anionic complex and additives to make homogeneous solution in degassed solvents. And purging argon also degasses resulting solution.

Note 2: solution B is prepared by dissolving dissolving group IIA metal salts. Solution was degassed prior to use Note 3: the impregnation of solution on solid support is carried out by wetting solids with solution A and evaporating in vacuum at 50° C. unless stated Note 4: addition of impregnated solids with components of A to solution B is carried out at ambient temperature unless stated.

Note 5: the impregnation of solution A may be bypassed instead following procedure may be employed. Support is suspended in solvent to which solution is pumped in with simultaneous removal of solvent component of solution A, solvent is also pumped in such a rate that liquid volume of the container remain same. After this solution B addition aging and solid isolation is carried out as described earlier.

| Example | Solution A | Solution B | Procedure |
|---|---|---|---|
| 169. | HRhCO(TPPTS)3, 50 mg, TPPTS 200 mg. Dissolved in water 2 ml | Saturated barium nitrate in water 2 ml | 2 gm Davisil was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 170. | HRhCO(TPPTS)3, 50 mg, TPPTS 200 mg. Dissolved in water 2 ml | Saturated strontium chloride in water 2 ml | 2 gm Davisil was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |

| Example | Solution A | Solution B | Procedure |
|---|---|---|---|
| 171. | HRhCO(TPPTS)3, 50 mg, TPPTS 200 mg. Dissolved in water 2 ml | 500 mg of calcium chloride in 2 ml water | 2 gm Davisil was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 172. | HRhCO(TPPTS)3, 50 mg, TPPTS 200 mg. Dissolved in water 2 ml | Barium nitrate saturated solution in water | 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 173. | HRhCO(TPPTS)3, 50 mg, TPPTS 200 mg. Dissolved in water 2 ml | Strontium chloride saturated solution in water 2 ml | 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 174. | HRhCO(TPPTS)3, 50 mg, TPPTS 200 mg. Dissolved in water 2 ml | Calcium chloride 500 mg solution in 2 ml water | 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 175. | HRhCO(TPPTS)3, 50 mg, TPPTS 200 mg. Dissolved in water 2 ml | Barium nitrate saturated solution in water 2 ml | 2 gm bentonite was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 176. | HRhCO(TPPTS)3, 50 mg, TPPTS 200 mg. Dissolved in water 2 ml | Strontium chloride saturated solution in water | 2 gm bentonite was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |
| 177. | HRhCO(TPPTS)3, 50 mg, TPPTS 200 mg. Dissolved in water 2 ml | Calcium chloride 500 mg solution in 2 ml water | 2 gm bentonite was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield pale yellow colored solid powder. |

-continued

| Example | Solution A | Solution B | Procedure |
|---|---|---|---|
| 178. | HRhCO(TPPTS)3, 50 mg, TPPTS 200 mg. Dissolved in water 2 ml | Barium nitrate saturated solution in water | 2 gm charcoal was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield black colored solid powder. |
| 179. | HRhCO(TPPTS)3, 50 mg, TPPTS 200 mg. Dissolved in water 2 ml | Strontium chloride saturated solution in water | 2 gm charcoal was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield black colored solid powder. |
| 180. | HRhCO(TPPTS)3, 50 mg, TPPTS 200 mg. Dissolved in 2 ml water | Calcium chloride 500 mg solution in 2 ml water | 2 gm charcoal was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours to yield black colored solid powder. |
| 181. | Ru(H)(Cl)(TPPTS)$_3$ 50 mg TPPTS 200 mg Dissolved in 2 ml water | Barium nitrate saturated solution in 2 ml water | 2 gm davisil was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 182. | Ru(H)(Cl)(TPPTS)$_3$ 50 mg TPPTS 200 mg Dissolved in 2 ml water. | Strontium chloride saturated solution in 2 ml water | 2 gm davisil was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder.. |
| 183. | Ru(H)(Cl)(TPPTS)$_3$ 50 mg TPPTS 200 mg Dissolved in 2 ml water | Barium nitrate saturated solution in 2 ml water | 2 gm γ-alumina was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 184. | Ru(H)(Cl)(TPPTS)$_3$ 50 mg. TPPTS 200 mg Dissolved in 2 ml water | Strontium chloride saturated solution in 2 ml water | 2 gm γ-alumina was wetted with 100 µl portion of solution A and evaporated under vacuum 10 mm Hg with simultaneous tumbling remaining solution A was added in 100 µl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |

-continued

| Example | Solution A | Solution B | Procedure |
|---|---|---|---|
| 185. | Ru(H)(Cl)(TPPTS)$_3$ 50 mg<br>TPPTS 200 mg<br>Sodium polyvinylsulfonate<br>500 mg Dissolved in 2 ml<br>water | Strontium chloride<br>saturated solution in<br>2 ml water | 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 186. | Ru(H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 187. | Ru(H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | 2 gm titania was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 188. | Ru(H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | 2 gm zirconia 2 gm γ-alumina was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield light brown colored solid powder. |
| 189. | Ru(H)(Cl)(TPPTS)$_3$ 50 mg<br>TPPTS 200 mg<br>Sodium polyvinylsulfonate<br>500 mg Dissolved in 2 ml<br>water | Barium nitrate<br>saturated solution in<br>2 ml water | 2 gm activated charcoal was wetted with 100 μl portion of solution A and evaporated under vacuum 10 mm Hg with simultaneous tumbling remaining solution A was added in 100 μl fractions and solid was isolated this powder was added to benzene 25 ml in apparatus described in fig.reflux was started and solution B was added in equal fractions over a period of 2 hours while simultaneous removal of azeotropic water and suspension was further agitated for 10 hours filtered to yield black colored solid powder. |
| 190. | PdCl$_2$(TPPTS)$_2$ 10 mg<br>TPPTS 100 mg<br>Poly acrylic acid sodium salt<br>in 5 ml | Barium nitrate<br>saturated solution 5<br>ml | 2 gm shredded asbestos rope was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene. soultion B was added in equal fractions over a period of 2 hours and simultaneous removal of azeotropic water and suspension was further continued. Formed suspension was agitated.10 hours filtered to yield yellow gray colored solid powder. |
| 191. | PdCl$_2$(TPPTS)$_2$ 10 mg<br>TPPTS 100 mg<br>Poly acrylic acid sodium salt<br>in 5 ml | Strontium chloride<br>saturated solution 5<br>ml | 2 gm shredded asbestos rope was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield yellow gray colored solid powder. |

| Example | Solution A | Solution B | Procedure |
|---|---|---|---|
| 192. | PdCl$_2$(TPPTS)$_2$ 10 mg<br>TPPTS 100 mg<br>Poly acrylic acid sodium salt<br>in 5 ml | 500 mg calcium<br>chloride in 5 ml<br>water. | 2 gm shredded asbestos rope was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours filtered to yield yellow gray colored solid powder. |
| 193. | PdAc$_2$ BYPYDS 25 mg<br>BYPYDS 100 mg<br>Dissolved in 2 ml water | Barium nitrate<br>saturated solution<br>5 ml | 2 gm davisil was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield light orange colored solid powder. |
| 194. | PdAc$_2$ BYPYDS 25 mg<br>BYPYDS 100 mg<br>Dissolved in 2 ml water | Strontium chloride<br>saturated solution<br>5 ml | 2 gm davisil was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield light orange colored solid powder. |
| 195. | PdAc$_2$ BYPYDS 25 mg<br>BYPYDS 100 mg<br>Dissolved in 2 ml water | 500 mg calcium<br>chloride in 5 ml<br>water | 2 gm davisil was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield light orange colored solid powder. |
| 196. | PdAc$_2$ BYPYDS 25 mg<br>BYPYDS 100 mg<br>Dissolved in 2 ml water | Barium nitrate<br>saturated solution<br>5 ml | 2 gm bentonite was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield light orange colored solid powder. |

-continued

| Example | Solution A | Solution B | Procedure |
|---|---|---|---|
| 197. | PdAc$_2$ tri ortho tolyl phosphine trisulfonated 25 mg<br>Tri ortho tolyl phosphine trisulfonated 100 mg<br>Dissolved in 2 ml water | Barium nitrate saturated solution 5 ml | 2 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow brown colored solid powder. |
| 198. | PdAc$_2$ tri ortho tolyl phosphine trisulfonated 25 mg<br>Tri ortho tolyl phosphine trisulfonated 100 mg<br>Dissolved in 2 ml water | Strontium chloride saturated solution 5 ml | 2 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Fanned suspension was agitated for .10 hours filtered to yield pate yellow brown colored solid powder. |
| 199. | PdAc$_2$ trio tolyl phosphine trisulfonated 25 mg<br>Tri ortho tolyl phosphine trisulfonated 100 mg<br>Dissolved in 2 ml water | Barium nitrate saturated solution 5 ml | 2 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow brown colored solid powder. |
| 200. | PdAc$_2$ tri ortho tolyl phosphine trisulfonated 25 mg<br>Tri ortho tolyl phosphine trisulfonated 100 mg<br>Dissolved in 2 ml water | Barium nitrate saturated solution 5 ml | 2 gm charcoal was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 24 hours filtered to yield black colored solid powder. |
| 201. | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale solid powder of white color with blue tinge. |
| 202. | NiCl$_2$.(TPPTS)$_2$ 25 mg<br>TPPTS 100 mg<br>Sodium carboxy methyl cellulose 100 mg<br>Dissolved in 2 ml | Saturated barium nitrate in 2 ml water | 1 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield solid powder of white color with blue tinge. |

| Example | Solution A | Solution B | Procedure |
|---|---|---|---|
| 203 | $NiCl_2.(TPPTS)_2$ 25 mg<br>TPPTS 100 mg<br>Sodium carboxy methyl cellulose 100 mg<br>Dissolved in 2 ml | Saturated barium nitrate in 2 ml water | 1 gm zirconia was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale blue colored solid powder. |
| 204. | $NiCl_2.(TPPTS)_2$ 25 mg<br>TPPTS 100 mg<br>Sodium carboxy methyl cellulose 100 mg<br>Dissolved in 2 ml | Saturated strontium chloride in 2 ml water | 1 gm zirconia was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield solid powder of white color with slight blue tinge. |
| 205. | $NiCl_2.(TPPTS)_2$ 25 mg<br>TPPTS 100 mg<br>Sodium carboxy methyl cellulose 100 mg<br>Dissolved in 2 ml | Saturated strontium chloride in 2 ml water | 1 gm titania was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield solid powder of white color with blue tinge. |
| 206. | $NiCl_2.(TPPTS)_2$ 25 mg<br>TPPTS 100 mg<br>Sodium carboxy methyl cellulose 100 mg<br>Dissolved in 2 ml | Saturated strontium chloride in 2 ml water | 1 gm asbestos was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield gray colored solid powder. |
| 207. | (IrClCOD) 5 mg exchanged with TPPTS 100 mg.<br>Poly acrylic acid sodium salt 100 mg<br>In 2 ml water | Saturated strontium chloride in 2 ml water | 1 gm davisil was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 208. | (IrClCOD) 5 mg exchanged with TPPTS 100 mg.<br>Poly acrylic acid sodium salt 100 mg<br>In 2 ml water | Saturated strontium chloride in 2 ml water | 1 gm keisulghur was suspended in benzene 25 ml in apparatus described in fig agitated. The temperature of the suspension was slowly raised such that it gently refluxes to which was added 100 µl portion of solution A and solvent component was azeotropically removed, remaining solution A was added in 100 µl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |

-continued

| Example | Solution A | Solution B | Procedure |
|---|---|---|---|
| 209. | (IrClCOD) 5 mg exchanged with TPPTS 100 mg. Poly acrylic acid sodium salt 100 mg In 2 ml water | Saturated strontium chloride in 2 ml water | 1 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractious over a period of 2 hours and simultaneous removal of azeotropic water and suspension was further continued. Formed suspension was agitated 10 hours filtered to yield pale yellow colored solid powder. |
| 210. | (RuCl$_2$COD) 5 mg exchanged with diphenyl phosphino ethane tetrasulfonate 100 mg. Poly acrylic acid sodium salt 100 mg In 2 ml water | Saturated strontium chloride in 2 ml water | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-brown colored solid powder. |
| 211. | (RuCl$_2$COD) 5 mg exchanged with diphenyl phosphino ethane tetrasulfonate 100 mg. Poly acrylic acid sodium salt 100 mg In 2 ml water | Saturated strontium chloride in 2 ml water | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-brown colored solid powder. |
| 212. | (RuCl$_2$COD) 5 mg exchanged with diphenyl phosphino ethane tetrasulfonate 100 mg. Poly acrylic acid sodium salt 100 mg In 2 ml water | 500 mg calcium chloride in 2 ml water | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-brown colored solid powder. |
| 213. | Rh(COD)PF$_6$/S,S chiraphos tetrasulfonate 25 mg S,S chiraphos tetrasulfonate 25 mg Sodium alginate 100 mg dissolved in 2 ml water | Saturated strontium chloride solution 2 ml | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 214. | Rh(COD)PF$_6$/S,S chiraphos tetrasulfonate 25 mg S,S chiraphos tetrasulfonate 25 mg Sodium alginate 100 mg dissolved in 2 ml water | Saturated barium nitrate solution 2 ml | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |

-continued

| Example | Solution A | Solution B | Procedure |
|---|---|---|---|
| 215. | Rh(COD)PF$_6$/S,S chiraphos tetrasulfonate 25 mg<br>S,S chiraphos tetrasulfonate 25 mg<br>Sodium alginate 100 mg dissolved in 2 ml water | Saturated barium nitrate solution 2 ml | 1 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 216. | Rh(COD)PF$_6$/S,S chiraphos tetrasulfonate 25 mg<br>S,S chiraphos tetrasulfonate 25 mg<br>Sodium alginate 100 mg dissolved in 2 ml water | Saturated barium nitrate solution 2 ml | 1 gm titania was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 217. | HRhCO(TPATS)$_3$ 10 mg<br>100 mg TPATS<br>carboxy methyl cellulose sodium 100 mg in 1 ml water | 500 mg Calcium chloride solution in water 5 ml | 1 gm titania was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-green colored solid powder. |
| 218. | HRhCO(TPATS)$_3$ 10 mg<br>100 mg TPATS<br>carboxy methyl cellulose sodium 100 mg in 1 ml water | Strontium chloride saturated solution in water 5 ml | 1 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-green colored solid powder. |
| 219. | HRhCO(TPATS)$_3$ 10 mg<br>100 mg TPATS<br>carboxy methyl cellulose sodium 100 mg in 1 ml water | Barium nitrate saturated solution in water 5 ml | 1 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal tractions over a period of 2 hours and simultaneous removal of azeotropic water and suspension was further continued. Formed suspension was agitated for 10 hours filtered to yield pale yellow-green colored solid powder. |
| 220. | HRhCO(TPATS)$_3$ 10 mg<br>100 mg TPATS<br>carboxy methyl cellulose sodium 100 mg in 1 ml water | Strontium chloride saturated solution in water 5 ml | 1 gm titania was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-green colored solid powder. |

-continued

| Example | Solution A | Solution B | Procedure |
|---|---|---|---|
| 221. | HRhCO(TPATS)$_3$ 10 mg<br>100 mg TPATS<br>carboxy methyl cellulose<br>sodium 100 mg in 1 ml water | Strontium chloride saturated solution in water 5 ml | 1 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow-green colored solid powder. |
| 222. | HRhCO(BISBIS) 50 mg<br>BISBIS 200 mg<br>200 mg sodium sulfate<br>dissolved in 2 ml water | Saturated barium nitrate solution is 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 223. | HRhCO(BISBIS) 50 mg<br>BISBIS 200 mg<br>200 mg polyvinyl sulfonic<br>acid dissolved in 2 ml water | 1 g calcium chloride solution In 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 224. | HRhCO(BISBIS) 50 mg<br>BISBIS 200 mg<br>200 mg polyacrylic acid<br>sodium salt dissolved in 2 ml water | Saturated barium nitrate solution is 5 ml water | 2 gm titania was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 225. | HRhCO(BISBIS) 50 mg<br>BISBIS 200 mg<br>200 mg polyvinyl sulfonic<br>acid dissolved in 2 ml water | Saturated strontium chloride solution is 5 ml water | 2 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 226. | HRhCO(BISBIS) 50 mg<br>BISBIS 200 mg<br>200 mg polyvinyl sulfonic acid<br>dissolved in 2 ml water | Saturated barium nitrate solution is 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |

-continued

| Example | Solution A | Solution B | Procedure |
|---|---|---|---|
| 227. | HRhCO(BISBIS) 50 mg<br>BISBIS 200 mg<br>200 mg polyvinyl sulfonic acid dissolved in 2 ml water | Saturated barium nitrate solution is 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 228. | PtCl$_2$(TPPTS)$_2$ 50 mg<br>TPPTS 100 mg<br>100 mg sodium alginate<br>Dissolved in 2 ml water and 0.5 ml butane diol | Saturated solution of barium nitrate 5 ml | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 229. | PtCl$_2$(TPPTS)$_2$ 50 mg<br>TPPTS 100 mg<br>100 mg oxalic acid sodium salt.<br>Dissolved in 2 ml water and 0.5 ml butane diol | Saturated solution of barium nitrate 5 ml | 2 gm alumina 2 gm was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 230. | PtCl$_2$(TPPTS)$_2$ 50 mg<br>TPPTS 100 mg<br>100 mg citric acid<br>Dissolved in 2 ml water and 0.5 ml ethylene glycol | Saturated solution of strontium chloride 5 ml | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |
| 231. | PtCl$_2$(TPPTS)$_2$ 50 mg<br>TPPTS 100 mg<br>100 mg polyacrylic acid sodium salt.<br>Dissolved in 2 ml water and 0.5 ml butane diol | Saturated solution of barium nitrate 5 ml | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene soultion B was added in equal fractions over a period of 2 hours and simultaneous removal of azeotropic water and suspension was further continued. Formed suspension was agitated for 10 hours filtered to yield pale yellow colored solid powder. |

| Example | Solution A | Solution B | Procedure |
|---|---|---|---|
| 232. | PtCl$_2$(TPFTS)$_2$ 50 mg<br>TPPTS 300 mg<br>Dissolved in 2 ml water | Saturated solution of barium nitrate 5 ml | 2 gm shreded asbestos rope 2 gm zirconia was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours filtered to yield pale yellow-gray colored solid powder. |
| 233. | Cobalt N,N'ethylene bis (salicyldiamine) 5-sulfonato sodium 100 mg.<br>Sodium phosphate. 500 mg.<br>In 5 ml water | Saturated barium nitrate solution in water 5 ml | 2 gm davisil was suspended in benzene 25 ml in apparatus described in fig agitated. Hie temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours filtered to yield pale brown colored solid powder. |
| 234. | Cobalt N,N'ethylene bis (salicyldiamine) 5-sulfonato sodium 100 mg.<br>Sodium silicate 500 mg.<br>In 5 ml water | Saturated barium nitrate solution in water 5 ml | 2 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours filtered to yield pale brown colored solid powder. |
| 235. | Cobalt N,N'ethylene bis (salicyldiamine) 5-sulfonato sodium 100 mg.<br>Polyvinyl sulfonate sodium. 500 mg.<br>In 5 ml water | Saturated barium nitrate solution in water 5 ml | 2 gm titania was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued Formed suspension was agitated for 10 hours filtered to yield pale brown colored solid powder. |
| 236. | Cobalt N,N'ethylene bis (salicyldiamine) 5-sulfonato sodium 100 mg.<br>Polyvinyl sulfonate sodium. 500 mg.<br>In 5 ml water | Saturated barium nitrate solution in water 5 ml | 2 gm zirconia was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours filtered to yield pale brown colored solid powder. |
| 237. | Cobalt N,N'ethylene bis (salicyldiamine) 5-sulfonato sodium 100 mg.<br>Polyvinyl sulfonate sodium. 500 mg.<br>In 5 ml water | 2 g calcium chloride solution in water 5 ml | 2 gm sbreded asbestos rope was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene. soultion B was added in equal fractions over a period of 2 hours and simultaneous removal of azeotropic water and suspension was further continued. Formed suspension was agitated for 10 hours filtered to yield gray colored solid powder. |

-continued

| Example | Solution A | Solution B | Procedure |
|---|---|---|---|
| 238. | Cobalt (II), 4, 4', 4'', 4'''-tetrasulfopthalocynine. 500 mg And 500 mg sodium sodium poly vinyl sulfonate in 5 ml water | Saturated strontium chloride in 5 ml water | 2 gm shreded asbestos rope was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene. soultion B was added in equal fractions over a period of 2 hours and simultaneous removal of azeotropic water and suspension was further continued. Formed suspension was agitated for 10 hours filtered to yield blue-gray colored solid powder. |
| 239. | Cobalt (II), 4, 4', 4'', 4'''-tetrasulfopthalocynine. 500 mg And 500 mg sodium phosphate in 5 ml water | Saturated barium nitrate in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder |
| 240. | Cobalt (II), 4, 4', 4'', 4'''-tetrasulfopthalocynine. 500 mg And 500 mg sodium phosphate in 5 ml water | Saturated strontium chloride in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder |
| 241. | Cobalt (II), 4, 4', 4'', 4'''-tetrasulfopthalocynine. 500 mg And 500 mg sodium phosphate in 5 ml water | 500 mg. $CaCl_2$ in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder |
| 242. | Copper (II), 4, 4', 4'', 4'''-tetrasulfopthalocynine. 500 mg And 500 mg sodium sulfate in 5 ml water | 500 mg. $CaCl_2$ in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was farther continued. Formed suspension was agitated for 10 hours and filtered to yield pale blue colored solid powder |

-continued

| Example | Solution A | Solution B | Procedure |
|---|---|---|---|
| 243. | Copper (II), 4, 4', 4'', 4'''-tetrasulfopthalocynine. 500 mg And 500 mg sodium silicate in 5 ml water | Saturated strontium chloride in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder |
| 244. | Copper (II), 4, 4', 4'', 4'''-tetrasulfopthalocynine. 500 mg And 500 mg sodium silicate in 5 ml water | Saturated barium nitrate in 5 ml water | 2 gm keisulghur was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |
| 245. | Copper (II), 4, 4', 4'', 4'''-tetrasulfopthalocynine. 500 mg And 500 mg sodium silicate in 5 ml water | Saturated barium nitrate in 5 ml water | 2 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |
| 246. | Copper (II), 4, 4', 4'', 4'''-tetrasulfopthalocynine. 500 mg And 500 mg sodium silicate in 5 ml water | Saturated strontiun chloride in 5 ml water | 2 gm bentonite was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |
| 247. | Manganese(II), 4, 4', 4'', 4'''-tetrasulfopthalocynine. 500 mg And 500 mg sodium silicate in 5 ml water | Saturated strontiun chloride in 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |
| 248. | Manganese(II), 4, 4', 4'', 4'''-tetrasulfopthalocynine. 500 mg And 500 mg sodium silicate in 5 ml water | Saturated barium nitrate in 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |

| Example | Solution A | Solution B | Procedure |
|---|---|---|---|
| 249. | Manganese(II), 4, 4', 4'', 4'''-tetrasulfopthalocynine. 500 mg And 500 mg sodium silicate in 5 ml water | Saturated barium nitrate in 5 ml water | 2 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |
| 250. | Manganese(II), 4, 4', 4'', 4'''-tetrasulfopthalocynine. 500 mg And 500 mg sodium polyvinyl sulfonate in 5 ml water | Saturated barium nitrate in 5 ml water | 2 gm alumina was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pate blue colored solid powder. |
| 251. | Iron (III), 4, 4', 4'', 4'''-tetrasulfopthalocynine oxygen adduct. 500 mg And 500 mg sodium sulfate in 5 ml water | Saturated strontium chloride in 5 ml water | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued Formed suspension was agitated for 10 hours and filtered to yield pale blue colored solid powder. |
| 252. | Iron (III), 4, 4', 4'', 4'''-tetrasulfopthalocynine oxygen adduct. 500 mg And 500 mg sodium sulfate in 5 ml water | Saturated barium nitrate in water 5 ml | 2 gm davisil was suspended in benzene 25 ml in apparatus described in fig agitated. The temperature of the suspension was slowly raised such that it gently refluxes to which was added 100 μl portion of solution A and solvent component was azeotropically removed, remaining solution A was added in 100 μl fractions until uniform suspension volume of suspension was maintained while maintaining volume by pumping benzene.soultion B was added in equal fractions over a period of 2 hours and simultaneous removal of azeotropic water and suspension was further continued. Formed suspension was agitated for 10 hours and filtered to yield pale blue colored solid powder. |

Note 1: solution A is prepared by dissolving anionic components including anionic complex and additives to make homogeneous solution in degassed solvents. And purging argon also degasses resulting solution.
Note 2: solution B is prepared by dissolving dissolving group IIA metal salts. Solution was degassed prior to use
Note 3: the impregnation of solution on solid support is carried out by wetting solids with solution A and evaporating in vacuum at 50° C. unless stated
Note 4: addition of impregnated solids with components of A to solution B is carried out at ambient temperature unless stated.
Note 5: the impregnation of solution A may be bypassed instead following procedure may be employed. Support is suspended in solvent to which solution is pumped in with simultaneous removal of solvent component of solution A. solvent is also pumped in such a rate that liquid volume of the container remain same. After this solution B addition aging and solid isolation is carried out as described earlier.

Examples 253–336
Preparation of catalytic formulation by deposition precipitation in fluidized bed The following examples illustrate one of the procedures for the preparation of the catalytic formulation of the invention to accordance with the method of formulation known as co precipitation near the surface of the solid support in fluidized bed.

The general procedure for the preparation of heterogeneous catalytic formula ion is described herein as making of a solution of anionically charged catalytic entity, catalytically inert anionic additive (termed as solution A) and solution of group II A metal ions (termed as solution B). The specified amount of support pretreated as described in earlier is charged in fluidization vessel and solids were fluidized with flow of argon. Temperature of the fluidization chamber was raised to specified temperature. Solution A was sprayed over the bed over the specified period of time in such a way that solids do not form lumps. Fluidization was continued further for specified period of time and solution B was similarly sprayed and fluidization was continued for specified period of time. Solids were discharged from vessel and aged for specified time. Catalytic formulation thus formed were washed with water, methanol, diethyl ether and dried in vacuum. Dry powder was stored under argon in gas tight vessel. These solid catalytic formulations can be used for appropriate reactions depending upon catalytically active entity incorporated in it.

Note 1: solution A is prepared by dissolving anionic components including anionic complex and additives to make homogeneous solution in degassed solvents. And resulting solution is also degassed by purging argon.

Note 2: solution B is prepared by dissolving group IIA metal salts. Solution was degassed prior to use Note 3: fluidized bed deposition was carried out in equipment described in FIG. (4).

| Example | Solution A | Solution B | Procedure |
|---|---|---|---|
| 253 | HRhCO(TPPTS)3, 50 mg, TPPTS 200 mg. 500 µl ethylene glycol dissolved in water 2 ml | Saturated barium nitrate in water 2 ml | 2 gm Davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 254 | HRhCO(TPPTS)3, 50 mg, TPPTS 200 mg. 500 µl ethylene glycol dissolved in water 2 ml | Saturated strontium chloride in water 2 ml | 2 gm Davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 255 | HRhCO(TPPTS)3, 50 mg, TPPTS 200 mg. 500 µl ethylene glycol dissolved in water 2 ml | 500 mg of calcium chloride in 2 ml water | 2 gm Davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 256 | HRhCO(TPPTS)3, 50 mg, TPPTS 200 mg. 500 µl ethylene glycol dissolved in water 2 ml | Barium nitrate saturated solution in water | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 257. | HRhCO(TPPTS)3, 50 mg, TPPTS 200 mg. 500 µl ethylene glycol dissolved in water 2 ml | Strontium chloride saturated solution in water 2 ml | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 258. | HRhCO(TPPTS) 50 mg, TPPTS 200 mg. 500 µl ethylene glycol dissolved in water 2 ml | Calcium chloride 500 mg solution in 2 ml water | 2 gm γ-alumina was was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 259. | HRhCO(TPPTS) 50 mg, TPPTS 200 mg. 500 µl ethylene glycol dissolved in water 2 ml | Barium nitrate saturated solution in water 2 ml | 2 gm was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 260. | HRhCO(TPPTS) 50 mg, TPPTS 200 mg. 500 µl ethylene glycol dissolved in water 2 ml | Strontium chloride saturated solution in water | 2 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 261. | HRhCO(TPPTS) 50 mg, TPPTS 200 mg. 500 µl ethylene glycol dissolved in water 2 ml | Calcium chloride 500 mg solution in 2 ml water | 2 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |

-continued

| Example | Solution A | Solution B | Procedure |
|---|---|---|---|
| 262. | HRhCO(TPPTS) 50 mg, TPPTS 200 mg. 500 µl ethylene glycol dissolved in water 2 ml | Barium nitrate saturated solution in water | 2 gm charcoal was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield black colored solid powder. |
| 263. | HRhCO(TPPTS) 50 mg, TPPTS 200 mg. 500 µl ethylene glycol dissolved in water 2 ml | Strontium chloride saturated solution in water | 2 gm charcoal was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield black colored solid powder. |
| 264. | HRhCO(TPPTS) 50 mg, TPPTS 200 mg. 500 µl ethylene glycol dissolved in 2 ml water | Calcium chloride 500 mg solution in 2 ml water | 2 gm charcoal was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield black colored solid powder. |
| 265. | Ru(H)(Cl)(TPPTS)$_3$ 50 mg 500 µl ethylene glycol TPPTS 200 mg dissolved in 2 ml water | Barium nitrate saturated solution in 2 ml water | 2 gm Davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield light brown colored solid powder. |
| 266. | Ru(H)(Cl)(TPPTS)$_3$ 50 mg 500 µl ethylene glycol TPPTS 200 mg dissolved in 2 ml water. | Strontium chloride saturated solution in 2 ml water | 2 gm Davisil was wetted with 100 µl portion of solution A and evaporated under vaccuum 10 mm Hg with simultaneous tumbling remaining solution A was added in 100 µl fractions and solid was isolated (moisture content ~20%) this powder was added to solution B in equal fractions over a period of 2 hours and suspension was further agitated for 10 hours filtered to yield light brown colored solid powder. |
| 267. | Ru(H)(Cl)(TPPTS)$_3$ 50 mg 500 µl ethylene glycol TPPTS 200 mg Dissolved in 2 ml water | Barium nitrate saturated solution in 2 ml water | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield light brown colored solid powder. |
| 268. | Ru(H)(Cl)(TPPTS)$_3$ 50 mg 500 µl ethylene glycol TPPTS 200 mg dissolved in 2 ml water | Strontium chloride saturated solution in 2 ml water | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield light brown colored solid powder. |
| 269. | Ru(H)(Cl)(TPPTS)$_3$ 50 mg TPPTS 200 mg 500 µl ethylene glycol Sodium polyvinylsulfonate 500 mg dissolved in 2 ml water | Strontium chloride saturated solution in 2 ml water | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield yield light brown colored solid powder. |
| 270. | Ru(H)(Cl)(TPPTS)$_3$ 50 mg TPPTS 200 mg 500 µl ethylene glycol Sodium polyvinylsulfonate 500 mg Dissolved in 2 ml water | Barium nitrate saturated solution in 2 ml water | 2 gm γ-alumina was fluidized in the current of argon and temperature of the fluidization vessel was raised to 50° C. and solution A was sprayed over a period of 2 hours once solids were free flowing solution B was sprayed over 2 hours and fluidization was continued further 2 hours. Solids were discharged and aged for 24 hours to yield light brown colored solid powder. |
| 271. | Ru(H)(Cl)(TPPTS)$_3$ 50 mg TPPTS 200 mg 500 µl ethylene glycol Sodium polyvinylsulfonate 500 mg Dissolved in 2 ml water | Barium nitrate saturated solution in 2 ml water | 2 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. solids were discharged and aged for 24 hours to yield light brown colored solid powder.. |
| 272. | Ru(H)(Cl)(TPPTS)$_3$ 50 mg 500 µl ethylene glycol TPPTS 200 mg Sodium polyvinylsulfonate 500 mg dissolved in 2 ml water | Barium nitrate saturated solution in 2 ml water | 2 gm zirconia was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield light brown colored solid powder.. |

-continued

| Example | Solution A | Solution B | Procedure |
|---|---|---|---|
| 273. | Ru(H)(Cl)(TPPTS)$_3$ 50 mg<br>TPPTS 200 mg<br>500 µl ethylene glycol<br>Sodium polyvinylsulfonate<br>500 mg Dissolved in 2 ml<br>water | Barium nitrate<br>saturated solution in<br>2 ml water | 2 gm activated charcoal was fluidized in the current of<br>argon and temperature of the fluidization vessel was<br>raised to 50° C. and solution A was sprayed over a<br>period of 2 hours once solids were free flowing<br>solution B was sprayed over 2 hours and fluidization<br>was continued fourther 2 hours. Solids were discharged<br>and aged for 24 hours to yield black colored solid<br>powder. |
| 274. | PdCl$_2$(TPPTS)$_2$ 10 mg<br>TPPTS 100 mg<br>500 µl ethylene glycol<br>Poly acrylic acid sodium salt<br>in 5 ml | Barium nitrate<br>saturated solution 5<br>ml | 2 gm shreaded asbestos roap was fluidized in the<br>current of argon and temperature of the fluidization<br>vessel was raised to 50° C. and solution A was sprayed<br>over a period of 2 hours once solids were free flowing<br>solution B was sprayed over 2 hours and fluidization<br>was continued fourther 2 hours. Solids were discharged<br>and aged for 24 hours to yield yellow gray colored<br>solid powder. |
| 275. | PdCl$_2$(TPPTS)$_2$ 10 mg<br>TPPTS 100 mg<br>500 µl ethylene glycol<br>Poly acrylic acid sodium salt<br>in 5 ml | Strontium chloride<br>saturated solution 5<br>ml | 2 gm shreaded asbestos roap was fluidized in the<br>current of argon and temperature of the fluidization<br>vessel was raised to 50° C. and solution A was sprayed<br>over a period of 2 hours once solids were free flowing<br>solution B was sprayed over 2 hours and fluidization<br>was continued fourther 2 hours. Solids were discharged<br>and aged for 24 hours to yield yellow gray colored<br>solid powder. |
| 276. | PdCl$_2$(TPPTS)$_2$ 10 mg<br>TPPTS 100 mg<br>500 µl ethylene glycol<br>Poly acrylic acid sodium salt<br>in 5 ml water | 500 mg calcium<br>chloride in 5 ml<br>water. | 2 gm shreaded asbestos roap was fluidized in the<br>current of argon and temperature of the fluidization<br>vessel was raised to 50° C. and solution A was sprayed<br>over a period of 2 hours once solids were free flowing<br>solution B was sprayed over 2 hours and fluidization<br>was continued fourther 2 hours. Solids were discharged<br>and aged for 24 hours to yield yellow gray colored<br>solid powder. |
| 277. | PdAc$_2$BYPYDS 25 mg<br>BYPYDS 100 mg<br>500 µl ethylene glycol<br>dissolved in 2 ml water | Barium nitrate<br>saturated solution<br>5 ml | 2 gm davisil was fluidized in the current of argon and<br>temperature of the fluidization vessel was raised to<br>50° C. and solution A was sprayed over a period of 2<br>hours once solids were free flowing solution B was<br>sprayed over 2 hours and fluidization was continued<br>fourther 2 hours. Solids were discharged and aged for<br>24 hours to yield loght orange colored solid powder. |
| 278. | PdAc$_2$BYPYDS 25 mg<br>BYPYDS 100 mg<br>500 µl ethylene glycol<br>dissolved in 2 ml water | Strontium chloride<br>saturated solution<br>5 ml | 2 gm davisil was fluidized in the current of argon and<br>temperature of the fluidization vessel was raised to 50°<br>C. and solution A was sprayed over a period of 2 hours<br>once solids were free flowing solution B was sprayed<br>over 2 hours and fluidization was continued fourther 2<br>hours. Solids were discharged and aged for 24 hours to<br>yield light orange colored solid powder. |
| 279. | PdAc$_2$BYPYDS 25 mg<br>BYPYDS 100 mg<br>500 µl ethylene glycol<br>dissolved in 2 ml water | 500 mg calcium<br>chloride in 5 ml<br>water | 2 gm davisil was fluidized in the current of argon and<br>temperature of the fluidization vessel was raised to 50°<br>C. and solution A was sprayed over a period of 2 hours<br>once solids were free flowing solution B was sprayed<br>over 2 hours and fluidization was continued fourther 2<br>hours. Solids were discharged and aged for 24 hours to<br>yield light orange colored solid powder. |
| 280. | PdAc$_2$BYPYDS 25 mg<br>BYPYDS 100 mg<br>500 µl ethylene glycol<br>dissolved in 2 ml water | Barium nitrate<br>saturated solution<br>5 ml | 2 gm bentonite was fluidized in the current of argon<br>and temperature of the fluidization vessel was raised to<br>50° C. and solution A was sprayed over a period of 2<br>hours once solids were free flowing solution B was<br>sprayed over 2 hours and fluidization was continued<br>fourther 2 hours. Solids were discharged and aged for<br>24 hours to yield loght orange colored solid powder. |
| 281. | PdAc$_2$ tri ortho tolyl<br>phosphine trisulfonated 25<br>mg<br>500 µl ethylene glycol<br>tri ortho tolyl phosphine<br>trisulfonated 100 mg<br>dissolved in 2 ml water | Barium nitrate<br>saturated solution<br>5 ml | 2 gm bentonite was fluidized in the current of argon<br>and temperature of the fluidization vessel was raised to<br>50° C. and solution A was sprayed over a period of 2<br>hours once solids were free flowing solution B was<br>sprayed over 2 hours and fluidization was continued<br>fourther 2 hours. Solids were discharged and aged for<br>24 hours to yield pale brown colored solid powder. |
| 282. | PdAc$_2$ tri ortho tolyl<br>phosphine trisulfonated 25<br>mg<br>500 µl ethylene glycol<br>Tri ortho tolyl phosphine<br>trisulfonated 100 mg<br>dissolved in 2 ml water | Strontium chloride<br>saturated solution<br>5 ml | 2 gm bentonite was fluidized in the current of argon<br>and temperature of the fluidization vessel was raised to<br>50° C. and solution A was sprayed over a period of 2<br>hours once solids were free flowing solution B was<br>sprayed over 2 hours and fluidization was continued<br>fourther 2 hours. Solids were discharged and aged for<br>24 hours to yield pale brown colored solid powder. |

| Example | Solution A | Solution B | Procedure |
|---|---|---|---|
| 283. | PdAc$_2$ trio tolyl phosphine trisulfonated 25 mg 500 µl ethylene glycol Tri ortho tolyl phosphine trisulfonated 100 mg dissolved in 2 ml water | Barium nitrate saturated solution 5 ml | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale brown colored solid powder. |
| 284. | PdAc$_2$ trio tolyl phosphine trisulfonated 25 mg 500 µl ethylene glycol tri ortho tolyl phosphine trisulfonated 100 mg dissolved in 2 ml water | Barium nitrate saturated solution 5 ml | 2 gm charcoal was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield black colored solid powder. |
| 285. | NiCl$_2$.(TPPTS)$_2$ 25 mg TPPTS 100 mg 500 µl ethylene glycol Sodium carboxy methyl cellulose 100 mg dissolved in 2 ml | Saturated barium nitrate in 2 ml water | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield solid powder of white color with blue tinge. |
| 286. | NiCl$_2$.(TPPTS)$_2$ 25 mg TPPTS 100 mg 500 µl ethylene glycol Sodium carboxy methyl cellulose 100 mg dissolved in 2 ml | Saturated barium nitrate in 2 ml water | 1 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield solid powder of white color with blue tinge. |
| 287. | NiCl$_2$.(TPPTS)$_2$ 25 mg 500 µl ethylene glycol TPPTS 100 mg Sodium carboxy methyl cellulose 100 mg dissolved in 2 ml | Saturated barium nitrate in 2 ml water | 1 gm zirconia was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield solid powder of white color with blue tinge. |
| 288. | NiCl$_2$.(TPPTS)$_2$ 25 mg 500 µl ethylene glycol TPPTS 100 mg Sodium carboxy methyl cellulose 100 mg dissolved in 2 ml | Saturated strontium chloride in 2 ml water | 1 gm zirconia was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 289. | NiCl$_2$.(TPPTS)$_2$ 25 mg 500 µl ethylene glycol TPPTS 100 mg Sodium carboxy methyl cellulose 100 mg dissolved in 2 ml | Saturated strontium chloride in 2 ml water | 1 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield solid powder of white color with blue tinge.. |
| 290. | NiCl$_2$.(TPPTS)$_2$ 25 mg 500 µl ethylene glycol TPPTS 100 mg Sodium carboxy methyl cellulose 100 mg Dissolved in 2 ml | Saturated strontium chloride in 2 ml water | 1 gm asbestos was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 291. | (IrClCOD) 5 mg exchanged with TPPTS 100 mg. Poly acrylic acid sodium salt 500 µl ethylene glycol 100 mg dissolved in 2 ml water | Saturated strontium chloride in 2 ml water | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 292. | (IrClCOD) 5 mg exchanged with TPPTS 100 mg. Poly acrylic acid sodium salt 500 µl ethylene glycol 100 mg dissolved in 2 ml water | Saturated strontium chloride in 2 ml water | 1 gm keisulghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 293. | (IrClCOD) 5 mg exchanged with TPPTS 100 mg. Poly acrylic acid sodium salt 500 µl ethylene glycol 100 mg dissolved in 2 ml water | Saturated strontium chloride in 2 ml water | 1 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |

-continued

| Example | Solution A | Solution B | Procedure |
|---|---|---|---|
| 294. | (RuCl$_2$COD) 5 mg exchanged with diphenyl phosphino ethane tetrasulfonate 100 mg. Poly acrylic acid sodium salt 500 µl ethylene glycol 100 mg dissolvd in 2 ml water | Saturated strontium chloride in 2 ml water | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 295. | (RuCl$_2$COD) 5 mg exchanged with diphenyl phosphino ethane tetrasulfonate 100 mg. Poly acrylic acid sodium salt 100 mg 500 µl ethylene glycol dissolved in 2 ml water | Saturated strontium chloride in 2 ml water | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 296. | (RuCl$_2$COD) 5 mg exchanged with diphenyl phosphino ethane tetrasulfonate 100 mg. Poly acrylic acid sodium salt 500 µl ethylene glycol 100 mg dissolved in 2 ml water | 500 mg calcium chloride in 2 ml water | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield light brown- yellow colored solid powder. |
| 297. | Rh(COD)PF$_6$/S,S chiraphos tetrasulfonate 25 mg S,S chiraphos tetrasulfonate 25 mg 500 µl ethylene glycol Sodium alginate 100 mg dissolved in 2 ml water | Saturated strontium chloride solution 2 ml | 1 gm davisil was fluidized in the current of argon and temperature of the fluidizadon vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 298. | Rh(COD)PF$_6$/S,S chiraphos tetrasulfonate 25 mg S,S chiraphos tetrasulfonate 25 mg 500 µl ethylene glycol Sodium alginate 100 mg dissolved in 2 ml water | Saturated barium nitrate solution 2 ml | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 299. | Rh(COD)PF$_6$/S,S chiraphos tetrasulfonate 25 mg S,S chiraphos tetrasulfonate 25 mg 500 µl ethylene glycol Sodium alginate 100 mg dissolved in 2 ml water | Saturated barium nitrate solution 2 ml | 1 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 300. | Rh(COD)PF$_6$/S,S chiraphos tetrasulfonate 25 mg S,S chiraphos tetrasulfonate 25 mg 500 µl ethylene glycol Sodium alginate 100 mg dissolved in 2 ml water | Saturated barium nitrate solution 2 ml | 1 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 301. | HRhCO(TPATS)$_3$ 10 mg 100 mg TPATS 500 µl ethylene glycol Carboxy methyl cellulose sodium 100 mg dissolved in 1 ml water | 500 mg Calcium chloride solution in water 5 ml | 1 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 302. | HRhCO(TPATS)$_3$ 10 mg 500 µl ethylene glycol 100 mg TPATS Carboxy methyl cellulose sodium 100 mg dissolved in 1 ml water | Strontium chloride saturated solution in water 5 ml | 1 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 303. | HRhCO(TPATS)$_3$ 10 mg 100 mg TPATS Carboxy methyl cellulose 500 µl ethylene glycol sodium 100 mg dissolved in 1 ml water | Barium nitrate saturated solution in water 5 ml | 1 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 304. | HRhCO(TPATS)$_3$ 10 mg 100 mg TPATS Carboxy methyl cellulose 500 µl ethylene glycol sodium 100 mg dissolved in 1 ml water | Strontium chloride saturated solution in water 5 ml | 1 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |

-continued

| Example | Solution A | Solution B | Procedure |
|---|---|---|---|
| 305. | HRhCO(TPATS)$_3$ 10 mg<br>100 mg TPATS<br>Carboxy methyl cellulose<br>500 µl ethylene glycol<br>sodium 100 mg dissolved in 1 ml water | Strontium chloride saturated solution in water 5 ml | 1 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 306. | HRhCO(BISBIS) 50 mg<br>BISBIS 200 mg<br>200 mg sodium sulfate<br>500 µl ethylene glycol<br>dissolved in 2 ml water | Saturated barium nitrate solution is 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 307. | HRhCO(BISBIS) 50 mg<br>BISBIS 200 mg<br>200 mg polyvinyl sulfonic acid<br>500 µl ethylene glycol<br>dissolved in 2 ml water | 1 g calcium chloride solution In 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 308. | HRhCO(BISBIS) 50 mg<br>BISBIS 200 mg<br>200 mg polyacrylic acid sodium salt<br>500 µl ethylene glycol<br>dissolved in 2 ml water | Saturated barium nitrate solution is 5 ml water | 2 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 309. | HRhCO(BISBIS) 50 mg<br>BISBIS 200 mg<br>200 mg polyvinyl sulfonic acid<br>500 µl ethylene glycol<br>dissolved in 2 ml water | Saturated strontium chloride solution is 5 ml water | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 310. | HRhCO(BISBIS) 50 mg<br>BISBIS 200 mg<br>200 mg polyvinyl sulfonic acid<br>500 µl ethylene glycol<br>dissolved in 2 ml water | Saturated barium nitrate solution is 5 ml water | 2 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow colored solid powder. |
| 311. | HRhCO(BISBIS) 50 mg<br>BISBIS 200 mg<br>200 mg polyvinyl sulfonic acid<br>500 µl ethylene glycol<br>dissolved in 2 ml water | Saturated barium nitrate solution is 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 312. | PtCl$_2$(TPPTS)$_2$ 50 mg<br>TPPTS 100 mg<br>100 mg sodium alginate<br>dissolved in 2 ml water and 0.5 ml butane diol | Saturated solution of barium nitrate 5 ml | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 313. | PtCl$_2$(TPPTS)$_2$ 50 mg<br>TPPTS 100 mg<br>100 mg oxalic acid sodium salt dissolved in 2 ml water and 0.5 ml butane diol | Saturated solution of barium nitrate 5 ml | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 314. | PtCl$_2$(TPPTS)$_2$ 50 mg<br>TPPTS 100 mg<br>100 mg citric acid<br>Dissolved in 2 ml water and 0.5 ml ethylene glycol | Saturated solution of strontium chloride 5 ml | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 315. | PtCl$_2$(TPPTS)$_2$ 50 mg<br>TPPTS 100 mg<br>100 mg polyacrylic acid sodium salt<br>Dissolved in 2 ml water and 0.5 ml butane diol | Saturated solution of barium nitrate 5 ml | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |

-continued

| Example | Solution A | Solution B | Procedure |
|---|---|---|---|
| 316. | PtCl$_2$(TPPTS)$_2$ 50 mg<br>TPPTS 300 mg<br>500 µl ethylene glycol<br>Dissolved in 2 ml water | Saturated solution of barium nitrate 5 ml | 2 gm shreded asbestos roap was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale yellow-green colored solid powder. |
| 317. | Cobalt N, N'ethylene bis (salicyldiamine) 5-sulfonato sodium 100 mg.<br>Sodium phosphate. 500 mg.<br>500 µl ethylene glycol<br>dissolved in 5 ml water | Saturated barium nitrate solution in water 5 ml | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale brown colored solid powder. |
| 318. | Cobalt N, N'ethylene bis (salicyldiamine) 5-sulfonato sodium 100 mg.<br>500 µl ethylene glycol<br>Sodium silicate 500 mg<br>dissolved in 5 ml water | Saturated barium nitrate solution in water 5 ml | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale brown colored solid powder. |
| 319. | Cobalt N, N'ethylene bis (salicyldiamine) 5-sulfonato sodium 100 mg.<br>500 µl ethylene glycol<br>Polyvinyl sulfonate sodium. 500 mg dissolved in 5 ml water | Saturated barium nitrate solution in water 5 ml | 2 gm titania was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale brown colored solid powder. |
| 320. | Cobalt N, N'ethylene bis (salicyldiamine) 5-sulfonato sodium 100 mg.<br>500 µl ethylene glycol<br>Polyvinyl sulfonate sodium. 500 mg dissolved in 5 ml water | Saturated barium nitrate solution in water 5 ml | 2 gm zirconia was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale brown colored solid powder. |
| 321. | Cobalt N, N'ethylene bis (salicyldiamine) 5-sulfonato sodium 100 mg.<br>500 µl ethylene glycol<br>Polyvinyl sulfonate sodium. 500 mg dissolved in 5 ml water | 2 g calcium chloride solution in water 5 ml | 2 gm shreded asbestos roap was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield gray colored solid powder. |
| 322. | Cobalt(II), 4, 4', 4'', 4'''-tetrasulfopthalocynine. 500 mg 500 µl ethylene glycol and 500 mg sodium sodium poly vinyl sulfonate in 5 ml water | Saturated strontium chloride in 5 ml water | 2 gm shreded asbestos roap was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. solids were discharged and aged for 24 hours to yield blue-gray colored solid powder. |
| 323. | Cobalt (II), 4, 4', 4'', 4'''-tetrasulfopthalocynine. 500 mg 500 µl ethylene glycol and 500 mg sodium phosphate dissolved in 5 ml water | Saturated barium nitrate in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 324. | Cobalt (II), 4, 4', 4'', 4'''-tetrasulfopthalocynine 500 mg 500 µl ethylene glycol and 500 mg sodium phosphate dissolved in 5 ml water | Saturated strontium chloride in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 325. | Cobalt (II), 4, 4', 4'', 4'''-tetrasulfopthalocynine 500 mg<br>500 µl ethylene glycol and 500 mg sodium phosphate dissolved in 5 ml water | 500 mg. CaCl$_2$ in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |

-continued

| Example | Solution A | Solution B | Procedure |
|---|---|---|---|
| 326. | Copper (II), 4, 4', 4", 4'''-tetrasulfopthalocynine. 500 mg 500 µl ethylene glycol and 500 mg sodium sulfate dissolved in 5 ml water | 500 mg. CaCl$_2$ in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 327. | Copper (II), 4, 4', 4", 4'''-tetrasulfopthalocynine. 500 mg 500 µl ethylene glycol and 500 mg sodium silicate dissolved in 5 ml water | Saturated strontium chloride in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 328. | Copper (II), 4, 4', 4", 4'''-tetrasulfopthalocynine. 500 mg 500 µl ethylene glycol And 500 mg sodium silicate in 5 ml water | Saturated barium nitrate in 5 ml water | 2 gm kesilghur was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 329. | Copper (II), 4, 4', 4", 4'''-tetrasulfopthalocynine 500 µl ethylene glycol adduct. 500 mg and 500 mg sodium silicate dissolved in 5 ml water | Saturated barium nitrate in 5 ml water | 2 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 330. | Copper (II), 4, 4', 4", 4'''-tetrasulfopthalocynine. 500 mg 500 µl ethylene glycol and 500 mg sodium silicate dissolved in 5 ml water | Saturated strontiun chloride in 5 ml water | 2 gm bentonite was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 331. | Manganese(II), 4, 4', 4", 4'''-tetrasulfopthalocynine. 500 mg 500 µl ethylene glycol and 500 mg sodium silicate dissolved in 5 ml water | Saturated strontiun chloride in 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 332. | Manganese(II), 4, 4', 4", 4'''-tetrasulfopthalocynine. 500 mg 500 µl ethylene glycol and 500 mg sodium silicate dissolved in 5 ml water | Saturated barium nitrate in 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 333. | Manganese(II), 4, 4', 4", 4'''-tetrasulfopthalocynine. 500 mg 500 µl ethylene glycol and 500 mg sodium silicate dissolved in 5 ml water | Saturated barium nitrate in 5 ml water | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 334. | Manganese(II), 4, 4', 4", 4'''-tetrasulfopthalocynine. 500 mg 500 µl ethylene glycol And 500 mg sodium polyvinyl sulfonate in 5 ml water | Saturated barium nitrate in 5 ml water | 2 gm alumina was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |
| 335. | Iron (III), 4, 4', 4", 4'''-tetrasulfopthalocynine oxygen adduct. 500 mg, 500 µl ethylene glycol and 500 mg sodium sulfate dissolved in 5 ml water | Saturated strontium chloride in 5 ml water | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |

-continued

| Example | Solution A | Solution B | Procedure |
|---------|-----------|-----------|-----------|
| 336. | Iron (III), 4, 4', 4'', 4'''-tetrasulfopthalocynine oxygen adduct. 500 mg, 500 μl ethylene glycol and 500 mg sodium sulfate dissolved in 5 ml water | Saturated barium nitrate in water 5 ml | 2 gm davisil was fluidized in the current of argon and temperature of the fluidization vessel was raised to 50° C. and solution A was sprayed over a period of 2 hours once solids were free flowing solution B was sprayed over 2 hours and fluidization was continued fourther 2 hours. Solids were discharged and aged for 24 hours to yield pale blue colored solid powder. |

Note 1: solution A is prepared by dissolving anionic components including anionic complex and additives to make homogeneous solution in degassed solvents. And resulting solution is also degassed by purging argon.
Note 2: solution B is prepared by dissolving group IIA metal salts. Solution was degassed prior to use
Note 3: fluidized bed deposition was carried out in equipment described in figure (4).

Example 337–420
Preparation of catalytic formulation by deposition precipitation in coating pan The following examples illustrate one of the procedures for the preparation of the catalytic formulation of the invention to accordance with the method of formulation known as co precipitation near the surface of the solid support.

The general procedure for the preparation of heterogeneous catalytic formulation is described herein as malting of a solution of anionically charged catalytic entity, catalytically inert anionic additive (termed as solution A) and solution of group II A metal ions (termed as solution B). The specified amount of support pretreated as described in earlier was charged in a pan, which was subsequently set in to rotation. During this procedure solids were tumbled. Temperature of the rotating pan was raised to desired temperature under the flow of argon solution a was sprayed on the bed of solids over a specified period followed by spraying solution B resulting solids were tumbled for specified period of time and dried in vacuum. Solids were washed with water, methanol and diethylether and dried. Dry powder was stored under argon in gas tight vessel. These solid catalytic formulations can be used for appropriate reactions depending upon catalytically active entity incorporated in it.

Note 1: solution A is prepared by dissolving anionic components including anionic complex and additives to make homogeneous solution in degassed solvents. And resulting solution is also degassed by purging argon.

Note 2: solution B is prepared by dissolving dissolving group IIA metal salts. Solution was degassed prior to use.

| Example | Solution A | Solution B | Procedure |
|---------|-----------|-----------|-----------|
| 337. | HRhCO(TPPTS)3, 50 mg, TPPTS 200 mg. 500 μl ethylene glycol dissolved in water 2 ml | Saturated barium nitrate in water 2 ml | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 338. | HRhCO(TPPTS)3, 50 mg, TPPTS 200 mg. 500 μl ethylene glycol dissolved in water 2 ml | Saturated strontium chloride in water 2 ml | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 339. | HRhCO(TPPTS) 50 mg, TPPTS 200 mg. 500 μl ethylene glycol dissolved in water 2 ml | 500 mg of calcium chloride in 2 ml water | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 340. | HRhCO(TPPTS)3, 50 mg, TPPTS 200 mg. 500 μl ethylene glycol dissolved in water 2 ml | Barium nitrate saturated solution in water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |

-continued

| Example | Solution A | Solution B | Procedure |
|---|---|---|---|
| 341. | HRhCO(TPPTS)3, 50 mg, TPPTS 200 mg. 500 µl ethylene glycol dissolved in water 2 ml | Strontium chloride saturated solution in water 2ml | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 342. | HRhCO(TPPTS)3, 50 mg, TPPTS 200 mg. 500 µl ethylene glycol dissolved in water 2 ml | Calcium chloride 500 mg solution in 2 ml water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 343. | HRhCO(TPPTS)3, 50 mg, TPPTS 200 mg. 500 µl ethylene glycol dissolved in water 2 ml | Barium nitrate saturated solution in water 2 ml | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 344. | HRhCO(TPPTS)3, 50 mg, TPPTS 200 mg. 500 µl ethylene glycol dissolved in water 2 ml | Strontium chloride saturated solution in water | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 345. | HRhCO(TPPTS)3, 50 mg, TPPTS 200 mg. 500 µl ethylene glycol dissolved in water 2 ml | Calcium chloride 500 mg solution in 2 ml water | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 346. | HRhCO(TPPTS)3, 50 mg, TPPTS 200 mg. 500 µl ethylene glycol dissolved in water 2 ml | Barium nitrate saturated solution in water | 2 gm charcoal was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield black colored solid powder. |
| 347. | HRhCO(TPPTS)3, 50 mg, TPPTS 200 mg. 500 µl ethylene glycol dissolved in water 2 ml | Strontium chloride saturated solution in water | 2 gm charcoal was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield black colored solid powder. |
| 348. | HRhCO(TPPTS)3, 50 mg, TPPTS 200 mg. 500 µl ethylene glycol dissolved in 2 ml water | Calcium chloride 500 mg solution in 2 ml water | 2 gm charcoal was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield black colored solid powder. |
| 349. | Ru(H)(Cl)(TPPTS)$_3$ 50 mg 500 µl ethylene glycol TPPTS 200 mg dissolved in 2 ml water | Barium nitrate saturated solution in 2 ml water | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |

-continued

| Example | Solution A | Solution B | Procedure |
|---|---|---|---|
| 350. | Ru(H)(Cl)(TPPTS)$_3$ 50 mg<br>500 µl ethylene glycol<br>TPPTS 200 mg dissolved in 2 ml water. | Strontium chloride saturated solution in 2 ml water | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |
| 351. | Ru(H)(Cl)(TPPTS)$_3$ 50 mg<br>500 µl ethylene glycol<br>TPPTS 200 mg Dissolved in 2 ml water | Barium nitrate saturated solution in 2 ml water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder.. |
| 352. | Ru(H)(Cl)(TPPTS)$_3$ 50 mg<br>500 µl ethylene glycol<br>TPPTS 200 mg dissolved in 2 ml water | Strontium chloride saturated solution in 2 ml water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |
| 353. | Ru(H)(Cl)(TPPTS)$_3$ 50 mg<br>TPPTS 200 mg<br>500 µl ethylene glycol<br>Sodium polyvinylsulfonate 500 mg dissolved in 2 ml water | Strontium chloride saturated solution in 2 ml water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield yield light brown colored solid powder. |
| 354. | Ru(H)(Cl)(TPPTS)$_3$ 50 mg<br>TPPTS 200 mg<br>500 µl ethylene glycol<br>Sodium polyvinylsulfonate 500 mg dissolved in 2 ml water | Barium nitrate saturated solution in 2 ml water | 2 gm γ-alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |
| 355. | Ru(H)(Cl)(TPPTS)$_3$ 50 mg<br>TPPTS 200 mg<br>500 µl ethylene glycol<br>Sodium polyvinylsulfonate 500 mg dissolved in 2 ml water | Barium nitrate saturated solution in 2 ml water | 2 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |
| 356. | Ru(H)(Cl)(TPPTS)$_3$ 50 mg<br>500 µl ethylene glycol<br>TPPTS 200 mg Sodium polyvinylsulfonate 500 mg dissolved in 2 ml water | Barium nitrate saturated solution in 2 ml water | 2 gm zirconia was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown colored solid powder. |
| 357. | Ru(H)(Cl)(TPPTS)$_3$ 50 mg<br>TPPTS 200 mg<br>500 µl ethylene glycol<br>Sodium polyvinylsulfonate 500 mg dissolved in 2 ml water | Barium nitrate saturated solution in 2 ml water | 2 gm activated charcoal was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield black colored solid powder. |
| 358. | PdCl$_2$(TPPTS)$_2$ 10 mg<br>TPPTS 100 mg<br>500 µl ethylene glycol<br>Poly acrylic acid sodium salt dissolved in 5 ml water | Barium nitrate saturated solution 5 ml | 2 gm shreaded asbestos roap was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield yellow gray colored solid powder. |

-continued

| Example | Solution A | Solution B | Procedure |
|---|---|---|---|
| 359. | PdCl$_2$(TPPTS)$_2$ 10 mg<br>TPPTS 100 mg<br>500 µl ethylene glycol<br>Poly acrylic acid sodium salt<br>dissolved in 5 ml water | Strontium chloride<br>saturated solution 5<br>ml | 2 gm shreaded asbestos roap was charged in a pan,<br>which was subsequently set in to rotation. During this<br>procedure solids were tumbled. Temperature of the<br>rotating pan was raised to 70° C., under the flow of<br>argon solution A was sprayed on the bed of solids over<br>a period of 4 hours followed by spraying solution B.<br>resulting solids were further tumbled for 2 hours and<br>dried in vacuum to yield yellow gray colored solid<br>powder. |
| 360. | PdCl$_2$(TPPTS)$_2$ 10 mg<br>TPPTS 100 mg<br>500 µl ethylene glycol<br>Poly acrylic acid sodium salt<br>dissolved in 5 ml water | 500 mg calcium<br>chloride in 5 ml<br>water. | 2 gm shreaded asbestos roap was charged in a pan,<br>which was subsequently set in to rotation. During this<br>procedure solids were tumbled. Temperature of the<br>rotating pan was raised to 70° C., under the flow of<br>argon solution A was sprayed on the bed of solids over<br>a period of 4 hours followed by spraying solution B.<br>resulting solids were further tumbled for 2 hours and<br>dried in vacuum to yield yellow gray colored solid<br>powder. |
| 361. | PdAc$_2$BYPYDS 25 mg<br>BYPYDS 100 mg<br>500 µl ethylene glycol<br>dissolved in 2 ml water | Barium nitrate<br>saturated solution<br>5 ml | 2 gm davisil was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield loght orange colored solid powder. |
| 362. | PdAc$_2$BYPYDS 25 mg<br>BYPYDS 100 mg<br>500 µl ethylene glycol<br>dissolved in 2 ml water | Strontium chloride<br>saturated solution<br>5 ml | 2 gm davisil was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield light orange colored solid powder. |
| 363. | PdAc$_2$BYPYDS 25 mg<br>BYPYDS 100 mg<br>500 µl ethylene glycol<br>dissolved in 2 ml water | 500 mg calcium<br>chloride in 5 ml<br>water | 2 gm davisil was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield light orange colored solid powder. |
| 364. | PdAc$_2$BYPYDS 25 mg<br>BYPYDS 100 mg<br>500 µl ethylene glycol<br>dissolved in 2 ml water | Barium nitrate<br>saturated solution<br>5 ml | 2 gm bentonite was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield loght orange colored solid powder. |
| 365. | PdAc$_2$ tri ortho tolyl<br>phosphine trisulfonated 25 mg<br>500 µl ethylene glycol<br>tri ortho tolyl phosphine<br>trisulfonated 100 mg<br>dissolved in 2 ml water | Barium nitrate<br>saturated solution<br>5 ml | 2 gm bentonite was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield pale brown colored solid powder. |
| 366. | PdAc$_2$ tri ortho tolyl<br>phosphine trisulfonated 25 mg<br>500 µl ethylene glycol<br>tri ortho tolyl phosphine<br>trisulfonated 100 mg<br>dissolved in 2 ml water | Strontium chloride<br>saturated solution<br>5 ml | 2 gm bentonite was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield pale yellow brown colored solid powder. |
| 367. | PdAc$_2$ tri ortho tolyl<br>phosphine trisulfonated 25 mg<br>500 µl ethylene glycol<br>tri ortho tolyl phosphine<br>trisulfonated 100 mg<br>Dissolved in 2 ml water | Barium nitrate<br>saturated solution<br>5 ml | 2 gm alumina was charged in a pan, which was<br>subsequently set in to rotation. During this procedure<br>solids were tumbled. Temperature of the rotating pan<br>was raised to 70° C., under the flow of argon solution A<br>was sprayed on the bed of solids over a period of 4<br>hours followed by spraying solution B. resulting solids<br>were further tumbled for 2 hours and dried in vacuum<br>to yield pale yellow brown colored solid powder. |

-continued

| Example | Solution A | Solution B | Procedure |
|---|---|---|---|
| 368. | PdAc$_2$ tri ortho tolyl phosphine trisulfonated 25 mg 500 μl ethylene glycol tri ortho tolyl phosphine trisulfonated 100 mg dissolved in 2 ml water | Barium nitrate saturated solution 5 ml | 2 gm charcoal was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield black colored solid powder. |
| 369. | NiCl$_2$.(TPPTS)$_2$ 25 mg TPPTS 100 mg 500 μl ethylene glycol Sodium carboxy methyl cellulose 100 mg dissolved in 2 ml of water | Saturated barium nitrate in 2 ml water | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield solid powder of white color with blue tinge. |
| 370. | NiCl$_2$.(TPPTS)$_2$ 25 mg TPPTS 100 mg 500 μl ethylene glycol Sodium carboxy methyl cellulose 100 mg dissolved in 2 ml of water | Saturated barium nitrate in 2 ml water | 1 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield solid powder of white color with blue tinge. |
| 371. | NiCl$_2$.(TPPTS)$_2$ 25 mg 500 μl ethylene glycol TPPTS 100 mg Sodium carboxy methyl cellulose 100 mg dissolved in 2 ml of water | Saturated barium nitrate in 2 ml water | 1 gm zirconia was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield solid powder of white color with blue tinge. |
| 372. | NiCl$_2$.(TPPTS)$_2$ 25 mg 500 μl ethylene glycol TPPTS 100 mg Sodium carboxy methyl cellulose 100 mg dissolved in 2 ml of water | Saturated strontium chloride in 2 ml water | 1 gm zirconia was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield solid powder of white color with blue tinge. |
| 373. | NiCl$_2$.(TPPTS)$_2$ 25 mg 500 μl ethylene glycol TPPTS 100 mg Sodium carboxy methyl cellulose 100 mg dissolved in 2 ml of water | Saturated strontium chloride in 2 ml water | 1 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield solid powder of white color with blue tinge. |
| 374. | NiCl$_2$.(TPPTS)$_2$ 25 mg 500 μl ethylene glycol TPPTS 100 mg 100 mg Sodium carboxy methyl cellulose dissolved in 2 ml | Saturated strontium chloride in 2 ml water | 1 gm asbestos was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield gray blue colored solid powder. |
| 375. | (IrClCOD) 5 mg exchanged with TPPTS 100 mg. 100 mg Poly acrylic acid sodium salt 500 μl ethylene glycol dissolved in 2 ml water | Saturated strontium chloride in 2 ml water | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 376. | (IrClCOD) 5 mg exchanged with TPPTS 100 mg. 100 mg Poly acrylic acid sodium salt 500 μl ethylene glycol dissolved in 2 ml water | Saturated strontium chloride in 2 ml water | 1 gm keisulghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |

-continued

| Example | Solution A | Solution B | Procedure |
|---|---|---|---|
| 377. | (IrClCOD) 5 mg exchanged with TPPTS 100 mg. Poly acrylic acid sodium salt 500 μl ethylene glycol 100 mg dissolved in 2 ml water | Saturated strontium chloride in 2 ml water | 1 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 378. | (RuCl$_2$COD) 5 mg exchanged with diphenyl phosphino ethane tetrasulfonate 100 mg. 100 mg Poly acrylic acid sodium salt 500 μl ethylene glycol dissolved in 2 ml water | Saturated strontium chloride in 2 ml water | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 379. | (RuCl$_2$COD) 5 mg exchanged with diphenyl phosphino ethane tetrasulfonate 100 mg. 100 mg Poly acrylic acid sodium salt, 500 μl ethylene glycol dissolved in 2 ml water | Saturated strontium chloride in 2 ml water | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 380. | (RuCl$_2$COD) 5 mg exchanged with diphenyl phosphino ethane tetrasulfonate 100 mg. 100 mg Poly acrylic acid sodium salt, 500 μl ethylene glycol dissolved in 2 ml water | 500 mg calcium chloride in 2 ml water | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield light brown-yellow colored solid powder. |
| 381. | Rh(COD)PF$_6$/S,S chiraphos tetrasulfonate 25 mg S,S chiraphos tetrasulfonate 25 mg, 500 μl ethylene glycol, Sodium alginate 100 mg dissolved in 2 ml water | Saturated strontium chloride solution 2 ml | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 382. | Rh(COD)PF$_6$/S,S chiraphos tetrasulfonate 25 mg S,S chiraphos tetrasulfonate 25 mg 500 μl ethylene glycol, Sodium alginate 100 mg, dissolved in 2 ml water | Saturated barium nitrate solution 2 ml | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 383. | Rh(COD)PF$_6$/S,S chiraphos tetrasulfonate 25 mg S,S chiraphos tetrasulfonate 25 mg, 500 μl ethylene glycol, Sodium alginate 100 mg dissolved in 2 ml water | Saturated barium nitrate solution 2 ml | 1 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 384. | Rh(COD)PF$_6$/S,S chiraphos tetrasulfonate 25 mg S,S chiraphos tetrasulfonate 25 mg, 500 μl ethylene glycol, Sodium alginate 100 mg dissolved in 2 ml water | Saturated barium nitrate solution 2 ml | 1 gm titania was charged in a pan, which was subsequently set in to rotation. During this procedure solids were tumbled. Temperature of tile rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 385. | HRhCO(TPATS)$_3$ 10 mg 100 mg TPATS 500 μl ethylene glycol Carboxy methyl cellulose sodium 100 mg dissolved in 1 ml water | 500 mg Calcium chloride solution in water 5 ml | 1 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |

-continued

| Example | Solution A | Solution B | Procedure |
|---|---|---|---|
| 386. | HRhCO(TPATS)$_3$ 10 mg 500 µl ethylene glycol 100 mg TPATS carboxy methyl cellulose sodium 100 mg dissolved in 1 ml water | Strontium chloride saturated solution in water 5 ml | 1 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 387. | HRhCO(TPATS)$_3$ 10 mg 100 mg TPATS carboxy methyl cellulose 500 µl ethylene glycol sodium 100 mg dissolved in 1 ml water | Barium nitrate saturated solution in water 5 ml | 1 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 388. | HRhCO(TPATS)$_3$ 10 mg 100 mg TPATS Carboxy methyl cellulose 500 µl ethylene glycol sodium 100 mg dissolved in 1 ml water | Strontium chloride saturated solution in water 5 ml | 1 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 389. | HRhCO(TPATS)$_3$ 10 mg 100 mg TPATS, sodium carboxy methyl cellulose 100 mg, 500 µl ethylene glycol, dissolved in 1 ml water | Strontium chloride saturated solution in water 5 ml | 1 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 390. | HRhCO(BISBIS) 50 mg BISBIS 200 mg, 200 mg sodium sulfate, 500 µl ethylene glycol, dissolved in 2 ml water | Saturated barium nitrate solution is 5 ml water | 2 gm davisila was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 391. | HRhCO(BISBIS) 50 mg BISBIS 200 mg 200 mg polyvinyl sulfonic acid, 500 µl ethylene glycol, dissolved in 2 ml water | 1 g calcium chloride solution In 5 ml water | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 392. | HRhCO(BISBIS) 50 mg BISBIS 200 mg 200 mg polyacrylic acid sodium salt, 500 µl ethylene glycol dissolved in 2 ml water | Saturated barium nitrate solution is 5 ml water | 2 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 393. | HRhCO(BISBIS) 50 mg BISBIS 200 mg 200 mg polyvinyl sulfonic acid, 500 µl ethylene glycol, dissolved in 2 ml water | Saturated strontium chloride solution is 5 ml water | 2 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |
| 394. | HRhCO(BISBIS) 50 mg BISBIS 200 mg, 200 mg polyvinyl sulfonic add, 500 µl ethylene glycol, dissolved in 2 ml water | Saturated barium nitrate solution is 5 ml water | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow colored solid powder. |

-continued

| Example | Solution A | Solution B | Procedure |
|---|---|---|---|
| 395. | HRhCO(BISBIS) 50 mg BISBIS 200 mg, 200 mg polyvinyl sulfonic acid, 500 μl ethylene glycol, dissolved in 2 ml water | Saturated barium nitrate solution is 5 ml water | 2 gm Davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 396. | PtCl$_2$(TPPTS)$_2$ 50 mg TPPTS 100 mg, 100 mg sodium alginate dissolved in 2 ml water and 0.5 ml butane diol | Saturated solution of barium nitrate 5 ml | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 397. | PtCl$_2$(TPPTS)$_2$ 50 mg TPPTS 100 mg, 100 mg oxalic acid sodium salt, dissolved in 2 ml water and 0.5 ml butane diol | Saturated solution of barium nitrate 5 ml | 2 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 398. | PtCl$_2$(TPPTS)$_2$ 50 mg TPPTS 100 mg, 100 mg citric acid, dissolved in 2 ml water and 0.5 ml ethylene glycol | Saturated solution of strontium chloride 5 ml | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 399. | PtCl$_2$(TPPTS)$_2$ 50 mg TPPTS 100 mg, 100 mg polyacrylic acid sodium salt, dissolved in 2 ml water and 0.5 ml butane diol | Saturated solution of barium nitrate 5 ml | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 400. | PtCl$_2$(TPPTS)$_2$ 50 mg, TPP 300 mg, 500 μl ethylene glycol, Dissolved in 2 ml water | Saturated solution of barium nitrate 5 ml | 2 gm shredded asbestos roap was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale yellow-green colored solid powder. |
| 401. | Cobalt N, N'ethylene bis (salicyldiamine) 5-sulfonato sodium 100 mg, Sodium phosphate. 500 mg., 500 μl ethylene glycol dissolved in 5 ml water | Saturated barium nitrate solution in water 5ml | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale brown colored solid powder. |
| 402. | Cobalt N, N'ethylene bis (salicyldiamine) 5-sulfonato sodium 100 mg, 500 μl ethylene glycol, Sodium silicate 500 mg dissolved in 5 ml water | Saturated barium nitrate solution in water 5 ml | 2 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale brown colored solid powder. |
| 403. | Cobalt N, N'ethylene bis (salicyldiamine) 5-sulfonato sodium 100 mg, 500 μl ethylene glycol, Polyvinyl sulfonate sodium. 500 mg dissolved in 5 ml water | Saturated barium nitrate solution in water 5 ml | 2 gm titania was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale brown colored solid powder. |

-continued

| Example | Solution A | Solution B | Procedure |
| --- | --- | --- | --- |
| 404. | Cobalt N, N'ethylene bis (salicyldiamine) 5-sulfonato sodium 100 mg, 500 µl ethylene glycol, polyvinyl sulfonate sodium. 500 mg dissolved in 5 ml water | Saturated barium nitrate solution in water 5 ml | 2 gm zirconia was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale brown colored solid powder. |
| 405. | Cobalt N, N'ethylene bis (salicyldiamine) 5-sulfonato sodium 100 mg, 500 µl ethylene glycol, polyvinyl sulfonate sodium. 500 mg in 5 ml water | 2 g calcium chloride solution in water 5 ml | 2 gm shreded asbestos roap was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield gray colored solid powder. |
| 406. | Cobalt (II), 4, 4', 4'', 4'''-tetrasulfopthalocynine 500 mg 500 µl ethylene glycol and 500 mg sodium sodium poly vinyl sulfonate in 5 ml water | Saturated strontium chloride in 5 ml water | 2 gm shreded asbestos roap was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield blue-gray colored solid powder. |
| 407. | Cobalt (II), 4, 4', 4'', 4'''-tetrasulfopthalocynine 500 mg 500 µl ethylene glycol and 500 mg sodium phosphate in 5 ml water | Saturated barium nitrate in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 408. | Cobalt (II), 4, 4', 4'', 4'''-tetrasulfopthalocynine 500 mg 500 µl ethylene glycol and 500 mg sodium phosphate in 5 ml water | Saturated strontium chloride in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 409. | Cobalt (II), 4, 4', 4'', 4'''-tetrasulfopthalocynine 500 mg, 500 µl ethylene glycol and 500 mg sodium phosphate in 5 ml water | 500 mg. $CaCl_2$ in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 410. | Copper (II), 4, 4', 4'', 4'''-tetrasulfopthalocynine. 500 mg, 500 µl ethylene glycol and 500 mg sodium sulfate in 5 ml water | 500 mg. $CaCl_2$ in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 411. | Copper (II), 4, 4', 4'', 4'''-tetrasulfopthalocynine. 500 mg, 500 µl ethylene glycol and 500 mg sodium silicate in 5 ml water | Saturated strontium chloride in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 412. | Copper (II), 4, 4', 4'', 4'''-tetrasulfopthalocynine. 500 mg, 500 µl ethylene glycol and 500 mg sodium silicate in 5 ml water | Saturated barium nitrate in 5 ml water | 2 gm kesilghur was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |

| Example | Solution A | Solution B | Procedure |
|---|---|---|---|
| 413. | Copper (II), 4, 4', 4'', 4'''-tetrasolfopthalocynine 500 μl ethylene glycol, 500 mg and 500 mg sodium silicate in 5 ml water | Saturated barium nitrate in 5 ml water | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 414. | Copper (II), 4, 4', 4'', 4'''-tetrasulfopthalocynine 500 mg, 500 μl ethylene glycol and 500 mg sodium silicate in 5 ml water | Saturated strontium chloride in 5 ml water | 2 gm bentonite was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 415. | Manganese(II), 4, 4', 4'', 4'''-tetrasulfopthalocynine. 500 mg, 500 μl ethylene glycol and 500 mg sodium silicate in 5 ml water | Saturated strontium chloride in 5 ml water | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 416. | Manganese(II), 4, 4', 4'', 4'''-tetrasulfopthalocynine. 500 mg, 500 μl ethylene glycol and 500 mg sodium silicate in 5 ml water | Saturated barium nitrate in 5 ml water | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield blue colored solid powder. |
| 417. | Manganese(II), 4, 4', 4'', 4'''-tetrasulfopthalocynine. 500 mg 500 μl ethylene glycol And 500 mg sodium silicate in 5 ml water | Saturated barium nitrate in 5 ml water | 2 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 418. | Manganese(II), 4, 4', 4'', 4'''-tetrasulfopthalocynine 500 mg, 500 μl ethylene glycol and 500 mg sodium polyvinyl sulfonate in 5 ml water | Saturated barium nitrate in 5 ml water | 2 gm alumina was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 419. | Iron (III), 4, 4', 4'', 4'''-tetrasulfopthalocynine oxygen adduct. 500 mg, 500 μl ethylene glycol and 500 mg sodium sulfate in 5 ml water | Saturated strontium chloride in 5 ml water | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |
| 420. | Iron (III), 4, 4', 4'', 4'''-tetrasulfopthalocynine oxygen adduct. 500 mg 500 μl ethylene glycol and 500 mg sodium sulfate in 5 ml water | Saturated barium nitrate in water 5 ml | 2 gm davisil was charged in a pan, which was subsequently set in to rotation. During this procedure solids were tumbled. Temperature of the rotating pan was raised to 70° C., under the flow of argon solution A was sprayed on the bed of solids over a period of 4 hours followed by spraying solution B. resulting solids were further tumbled for 2 hours and dried in vacuum to yield pale blue colored solid powder. |

Note 1: solution A is prepared by dissolving anionic components including anionic complex and additives to make homogeneous solution in degassed solvents. And resulting solution is also degassed by purging argon.

Note 2: solution B is prepared by dissolving dissolving group IIA metal salts. Solution was degassed prior to use.

Examples 421–429

Catalyst stability in various organic solvents

These examples illustrate the stability of catalysts m liquid phases. Stability of catalyst was assessed in order to establish integrity and resilience of catalyst in liquid phase reactions. Apparatus according to FIG. 2 was assembled and 5 g. catalyst was added in the extraction vessel. 0.5-liter solvent was charged in extraction vessel. Solids in the extractor were agitated and solvent in the round bottomed flask was set to boiling. Solid catalyst was continuously leached for 24 hours. Boiling liquid was brought to room temperature and analyzed for group IIA metal and transition metal. No leaching of catalytically active material was apparent.

| No | Catalyst | Extraction solvent | Observation |
|---|---|---|---|
| 421 | Catalytic entity: HRhCO(TPPTS)3 ($10^{-6}$ mols) Additive: TPPTS 6* $10^{-6}$ mols/ polyvinyl sulfonic acid 100 mg Support: 5 g silica Davisil ™ Group IIA metal: barium Method of preparation: deposition precipitation Colour of catalyst: pale yellow | Water | No leaching detected colour of solid remains unchanged |
| | | Methanol | No leaching detected colour of solid remains unchanged |
| | | Acetone | No leaching detected colour of solid remains unchanged |
| | | Thf | No leaching detected colour of solid remains unchanged |
| | | Acetonitrile | No leaching detected colour of solid becomes light orange |
| | | DMF | No leaching detected colour of solid becomes light orange |
| | | Chloroform | No leaching detected colour of solid remains unchanged |
| | | Tolune | No leaching detected colour of solid remains unchanged |
| | | Hexane | No leaching detected colour of solid remains unchanged |
| | | Acetic acid | No leaching detected colour of solid remains unchanged |
| 422 | Catalytic entity: Ru(H)(Cl)(TPPTS)$_4$ ($10^{-6}$ mols) Additive: TPPTS 8* $10^{-6}$ mols/ alginic acid 100 mg Support: 5 g silica Davisil ™ Group IIA metal: strontium Method of preparation: fluidized bed precipitation Colour of catalyst: pale brown | Water | No leaching detected colour of solid remains unchanged |
| | | Methanol | No leaching detected colour of solid remains unchanged |
| | | Acetone | No leaching detected colour of solid remains unchanged |
| | | Thf | No leaching detected colour of solid remains unchanged |
| | | Acetonitrile | No leaching detected colour of solid turns slightly dark |
| | | DMF | No leaching detected colour of solid changes slightly dark |
| | | Chloroform | No leaching detected colour of solid remains unchanged |
| | | Toluene | No leaching detected colour of solid remains unchanged |
| | | Hexane | No leaching detected colour of solid remains unchanged |
| | | Acetic acid | No leaching detected colour of solid remains unchanged |
| 423 | Catalytic entity: palladium acetate bypyridine disulfonated $10^{-6}$ mols Additive: bypyridine disulfonated $10^{-5}$ mols/ polyacrylic acid acid 100 mg Support: 5 g charcoal | Water | No leaching detected colour of solid remains unchanged |
| | | Methanol | No leaching detected colour of solid remains unchanged |
| | | Acetone | No leaching detected |

-continued

| No | Catalyst | Extraction solvent | Observation |
|---|---|---|---|
| | Group IIA metal: strontium<br>Method of preparation:<br>fluidized bed precipitation<br>Colour of catalyst: pale orange | <br><br>THF | colour of solid remains<br>unchanged.<br>No leaching detected<br>colour of solid remains<br>unchanged |
| | | Acetonitrile | No leaching detected<br>colour of solid remains<br>unchanged |
| | | DMF | No leaching detected<br>colour of solid remains<br>unchanged |
| | | Chloroform | No leaching detected<br>colour of solid remains<br>unchanged |
| | | Toluene | No leaching detected<br>colour of solid remains<br>unchanged |
| | | Hexane | No leaching detected<br>colour of solid remains<br>unchanged |
| | | Acetic acid | No leaching detected<br>colour of solid remains<br>unchanged |
| 424 | Catalytic entity:<br>cobalt(II)4,4',4'',4''',-<br>tetrasulfopthalocynine $10^{-6}$ mols<br>additive: sodium phosphate 100 mg<br>Support: 5 g gamma alumina<br>Group IIA metal: barium<br>Method of preparation: coating<br>pan precipitation<br>Colour of catalyst: pale blue | Water | No leaching detected<br>colour of solid remains<br>unchanged |
| | | Methanol | No leaching detected<br>colour of solid remains<br>unchanged |
| | | Acetone | No leaching detected<br>colour of solid remains<br>unchanged |
| | | THF | No leaching detected<br>colour of solid remains<br>unchanged |
| | | Acetonitrile | No leaching detected<br>colour of solid remains<br>unchanged |
| | | DMF | No leaching detected<br>colour of solid remains<br>unchanged |
| | | Chloroform | No leaching detected<br>colour of solid remains<br>unchanged |
| | | Toluene | No leaching detected<br>colour of solid remains<br>unchanged |
| | | Hexane | No leaching detected<br>colour of solid remains<br>unchanged |
| | | Acetic acid | No leaching detected<br>colour of solid remains<br>unchanged |
| 425 | Catalytic entity: sulfonated<br>quaternary ammonium<br>hydroxide benzyl triphenyl<br>amine $10^{-4}$ mols<br>additive: carboxymethyl<br>cellulose 100 mg<br>Support: 5 g activated charcoal<br>Group IIA metal: barium<br>Method of preparation:<br>coprecipitation | Water<br>Methanol<br>Acetone<br>THF<br>Chloroform<br>Toluene<br>Hexane | No leaching detected<br>No leaching detected<br>No leaching detected<br>No leaching detected<br>No leaching detected<br>No leaching detected<br>No leaching detected |
| 426 | Catalytic entity: cobalt(II) N,N'-<br>ethylene bis(salicyldiamine 5-<br>sodium sulfonate) $10^{-4}$ mols<br>additive: sodium sulfate 200 mg<br>Support: 5 g asbestos<br>Group IIA metal: barium<br>Method of preparation: coating pan<br>Color of the catalyst: gray brown | Water | No leaching detected<br>colour of solid remains<br>unchanged |
| | | Methanol | No leaching detected<br>colour of solid remains<br>unchanged |
| | | Acetone | No leaching detected<br>colour of solid remains<br>unchanged |
| | | THF | No leaching detected<br>colour of solid remains<br>unchanged |
| | | Acetonitrile | No leaching detected<br>colour of solid remains |

-continued

| No | Catalyst | Extraction solvent | Observation |
|---|---|---|---|
| | | DMF | unchanged<br>No leaching detected<br>colour of solid remains<br>unchanged |
| | | Chloroform | No leaching detected<br>colour of solid remains<br>unchanged |
| | | Toluene | No leaching detected<br>colour of solid remains<br>unchanged |
| | | Hexane | No leaching detected<br>colour of solid remains<br>unchanged |
| | | Acetic acid | No leaching detected<br>colour of solid remains<br>unchanged |
| 427 | Catalytic entity: $NiCl_2(TPPTS)_2$ $10^{-4}$ mols<br>additive: tppts $20* 10^{-4}$ mols<br>Support: 5 g activated charcoal<br>Group IIA metal: strontium<br>Method of preparation:<br>fluidized bed precipitation | Water<br>Methanol<br>Acetone<br>THF<br>Acetonitrile<br>DMF<br>Chloroform<br>Tolune<br>Hexane<br>Acetic acid | No leaching detected<br>No leaching detected<br>No leaching detected<br>No leaching detected<br>No leaching detected<br>No leaching detected<br>No leaching detected<br>No leaching detected<br>No leaching detected<br>No leaching detected |
| 428 | Catalytic entity: Rh $^+ClO_4^-$ (S,S)<br>chiraphos tetra sulfonated $10^{-6}$ mols<br>additive: s,s chiraphos $20* 10^{-6}$ mols<br>Support: 5 g silica Davisil ™<br>Group IIA metal: barium<br>Method of preparation: coating<br>pan precipitation<br>Color of the catalyst: pale<br>yellow | Water | No leaching detected<br>colour of solid remains<br>unchanged |
| | | Methanol | No leaching detected<br>colour of solid remains<br>unchanged |
| | | Acetone | No leaching detected<br>colour of solid remains<br>unchanged |
| | | Thf | No leaching detected<br>colour of solid remains<br>unchanged |
| | | Acetonitrile | No leaching detected<br>colour of solid remains<br>unchanged |
| | | DMF | No leaching detected<br>colour of solid remains<br>unchanged |
| | | Chloroform | No leaching detected<br>colour of solid remains<br>unchanged |
| | | Tolune | No leaching detected<br>colour of solid remains<br>unchanged |
| | | Hexane | No leaching detected<br>colour of solid remains<br>unchanged |
| | | Acetic acid | No leaching detected<br>colour of solid remains<br>unchanged |
| 429 | Catalytic entity: $MoO_4^{-2}$ $10^{-4}$ mols<br>additive: sodium phosphate 500 mg<br>Support: 5 g calcium silicate<br>Group IIA metal: calcium<br>Method of preparation:<br>coprecipitation | Water | No leaching detected<br>colour of solid remains<br>unchanged |
| | | Methanol | No leaching detected<br>colour of solid remains<br>unchanged |
| | | Acetone | No leaching detected<br>colour of solid remains<br>unchanged |
| | | Thf | No leaching detected<br>colour of solid remains<br>unchanged |
| | | Acetonitrile | No leaching detected<br>colour of solid remains<br>unchanged |
| | | DMF | No leaching detected<br>colour of solid remains<br>unchanged |
| | | Chloroform | No leaching detected<br>colour of solid remains<br>unchanged |

-continued

| No | Catalyst | Extraction solvent | Observation |
|---|---|---|---|
| | | Tolune | No leaching detected colour of solid remains unchanged |
| | | Hexane | No leaching detected colour of solid remains unchanged |
| | | Acetic acid | No leaching detected colour of solid remains unchanged |

Example 430

Hydroformylation reaction as a probe

This example illustrates the applicability of the catalytic formulation to liquid phase reaction wherein two gases react with substrate in liquid phase. This example also illustrates how solid catalyst can be employed to catalyze reaction and a preferred method to recover and recycle it.

Catalyst specification

| Catalytic entity | HRhCO(TPPTS)3 (10.8 * $10^{-6}$ mols) |
|---|---|
| Additive | TPPTS 6* $10^{-6}$ mols/polyvinyl sulfonic acid 100 mg |
| Support: | 5 g silica Davisil ™ |
| Group IIA metal | barium |
| Method of preparation | deposition precipitation |
| Colour of catalyst | pale yellow |
| Metal content in solid | 10.8 * $10^{-6}$ mols of rhodium. |

Reaction procedure: Under a argon atmosphere the microreactor was charged with 1 g. of catalyst and 25 ml of octene the reactor was flushed with $H_2$/CO mixture and reactor was heated to 75° C. and pressurized with $H_2$/CO mixture (1:1 by mole) to 600 psi and maintained at this temperature. Liquid suspension was stirred at 900 rpm. Reaction was continued for 240 min. analysis of the products confirmed conversion of olefins to aldehydes.

Conversion 14*$10^{-3}$ mols of octene

Turn over frequencies at 60 min were 894 hour$^{-1}$

Turnover number after 240 min was 1296.29 mols.mol$^{-1}$ of catalyst n/i ratio after 240 min was 2.7$_{(wherein\ n\ is\ linear\ aldehyde\ and\ I\ is\ iso\ aldehyde)}$ Color of recovered catalyst: light brown The catalyst was recovered by centrifugation and repeatedly washing reactor with toluen under nitrogen atmosphere. Solid catalyst was dried under vacuum. Which was recycled to perform reaction as described earlier to obtain equivalent activity and selectivity. The color of catalyst was light brown Examples 431

Need of the support

These comparative examples illustrate the need of solid support in the catalytic formulation and effect of loading of catalytically active solid material on solid support to decide a protocol for optimum loading.

Hydroformylation of hexene

Catalyst specifications:

| Catalytic entity | HRhCO(TPPTS)3 ($10^{-6}$ mols) |
|---|---|
| Additive | TPPTS 6* $10^{-6}$ mols/polyvinyl sulfonic acid 100 mg |
| Support: | 5 g silica Davisil ™ |
| Group IIA metal | barium |
| Method of preparation | deposition precipitation |
| Colour of catalyst | pale yellow |

Procedure

Under a argon atmosphere the microreactor was charged with 2 g of catalyst and 0.5 g (5.2*$10^{-4}$ mols) of hexene in 20 ml toluen the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 89% Olefin was converted to aldehydes with n/I selectivity of 1.80.

Under identical conditions 4*$10^{-7}$ mols of barium salt of rhodium catalyst failed to promote any reaction.

Example 432

Effect of the added ligand

These comparative examples illustrate the need of additional ligand in catalytic formulation. These examples also illustrate solid support in the catalytic formulation and effect of loading of catalytically active solid material on solid support to decide optimum loading.

Catalyst preparation catalyst of varying specifications were prepared by following method:

Hydroformylation of hexene

Preparation of catalyst:

Catalyst specifications:

| | Catalyst A | Catalyst B | Catalyst C |
|---|---|---|---|
| Catalytic entity | HRhCO(TPPTS)3 ($10^{-6}$ mols) | HRhCO(TPPTS)3 ($10^{-6}$ mols) | HRhCO(TPPTS)3 ($10^{-6}$ mols) |

-continued

|  | Catalyst A | Catalyst B | Catalyst C |
|---|---|---|---|
| Additive | polyvinyl sulfonic acid 100 mg | TPPTS $6*10^{-6}$ mols/ polyvinyl sulfonic acid 100 mg | TPPTS $12*10^{-6}$ mols/polyvinyl sulfonic acid 100 mg |
| Support: | 5 g silica Davisil ™ | 5 g silica Davisil ™ | 5 g silica Davisil ™ |
| Group IIA metal | barium | barium | barium |
| Method of preparation | deposition precipitation | deposition precipitation | deposition precipitation |
| Colour of catalyst | pale yellow | pale yellow | pale yellow |

Procedure:

Under a argon atmosphere the microreactor was charged with 2 g of catalyst and 0.5 g ($5.2*10^{-4}$ mols) of hexene in 20 ml tolune the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours.

Analysis of the products confirmed conversion of olefins to aldehydes. About 89% Olefin was converted to aldehydes with n/I selectivity of 1.80.

Example 433
Effect of added water-Hydroformylation of hexene

| Catalytic entity | HRhCO(TPPTS)3 ($10^{-6}$ mols) |
|---|---|
| Additive | TPPTS $6*10^{-6}$ mols/polyvinyl sulfonic acid 100 mg |
| Support: | 5 g silica Davisil ™ |
| Group IIA metal | Barium |
| Method of preparation | deposition precipitation |
| Colour of catalyst | pale yellow |
| Moisture content | 2% |

Procedure:

Under a argon atmosphere the microreactor was charged with 2 g of catalyst and 0.5 g ($5.2*10^{-4}$ mols) of hexene in 20 ml tolune the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 89% Olefin was converted to aldehydes with n/I selectivity of 1.80.

Under identical conditions in reaction charge 1 g water was added and after 24 hours only 5% conversion was obtained with similar n/I ratio.

Example 434
Continuous fixed bed experiment
Catalyst specifications:

| Catalytic entity | HRhCO(TPPTS)3 ($10^{-6}$ mols) |
|---|---|
| Additive | TPPTS $6*10^{-6}$ mols/polyvinyl sulfonic acid 100 mg |
| Support: | 5 g silica Davisil ™ |
| Group IIA metal | barium |
| Method of preparation | deposition precipitation |
| Colour of catalyst | pale yellow |

Procedure:

Accordingly the crucial evaluation indicating life of the catalyst, its stability and the durability was performed in a tubular fixed bed reactor by subjecting catalyst to hydroformylation in tubular trical bed reactor (φ½) at 80° C. and 300 psi $H_2$/CO (1:1) using 5 g. of catalyst. 5% decene in toluene was pumped continuously at the feed rate of 10 ml/hr conversion levels were 20%(fluctuating by ±2.2%) for aldehydes (n/i 2.1) after attaining steady state (5 hours). The reaction was further continued for 76 hr without loss of activity. Reaction was arrested by discontinuing the liquid feed and water was pumped for 1 hr. thereafter reactant feed was resumed. Initially there was no conversion, which was steadily resumed to earlier levels over the period of 10 hr. This observation was attributed to formation of water film on the catalyst surface, which physically retards contact of decene with catalyst surface. Moreover water does not wash out complex catalyst, which provides conclusive proof that reaction occurs in the solid state.

Example 435

Hydroformylation of hexene

Catalyst specifications:

| Catalytic entity | HRhCO(TPPTS)3 ($10^{-6}$ mols) |
|---|---|
| Additive | TPPTS $6*10^{-6}$ mols/polyvinyl sulfonic acid 100 mg |
| Support: | 5 g silica Davisil ™ |
| Group IIA metal | barium |
| Method of preparation | deposition precipitation |
| Color of catalyst | pale yellow |

Procedure:

Under a argon atmosphere the microreactor was charged with 200 mg of catalyst and 0.05 g ($5.2*10^{-4}$ mols) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 89% Olefin was converted to aldehydes with n/I selectivity of 1.91 the catalyst was recovered by washing reactor several times with toluene and catalyst was recovered by centrifugation, washing repeatedly with toluene and diethyl ether. Catalyst was dried under vacuum and recycled to obtain equivalent activity.

Example 436
Hydroformylation of styrene
Preparation of catalysts
Catalyst specifications:

| | |
|---|---|
| Catalytic entity | HRhCO(TPPTS)3 ($10^{-6}$ mols) |
| Additive | TPPTS 6* $10^{-6}$ mols/polyvinyl sulfonic acid 100 mg |
| Support: | 5 g silica Davisil ™ |
| Group IIA metal | barium |
| Method of preparation | deposition precipitation |
| Color of catalyst | pale yellow |

Under a argon atmosphere the microreactor was charged with 200 mg of catalyst and 0.05 g ($4.8*10^{-4}$) of styrene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 91% Olefin was converted to aldehydes with n/I ratio of 0.449. The catalyst was recovered by washing reactor several times with toluene and catalyst was recovered by centrifugation, washing repeatedly with toluene and diethyl ether. Catalyst was dried under vacuum and recycled to obtain equivalent activity.

Example 437
Hydroformylation of cyclohexene
Preparation of catalysts
Catalyst specifications:

| | |
|---|---|
| Catalytic entity | HRhCO(TPPTS)3 ($10^{-6}$ mols) |
| Additive | TPPTS 6* $10^{-6}$ mols/polyvinyl sulfonic acid 100 mg |
| Support: | 5 g silica Davisil ™ |
| Group IIA metal | barium |
| Method of preparation | deposition precipitation |
| Color of catalyst | pale yellow |

Under a argon atmosphere the microreactor was charged with 200 mg of catalyst and 0.05 g ($6.1*10^{-4}$ of cyclohexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 47% Olefin was converted to aldehydes. The catalyst was recovered by washing reactor several times with toluene and catalyst was recovered by centrifugation, washing repeatedly with toluene and diethyl ether. Catalyst was dried under vacuum and recycled to obtain equivalent activity.

Example 438
Hydroformylation of allyl alcohol
Catalyst specifications:

| | |
|---|---|
| Catalytic entity | HRhCO(TPPTS)3 ($10^{-6}$ mols) |
| Additive | TPPTS 6* $10^{-6}$ mols/polyvinyl sulfonic acid 100 mg |
| Support: | 5 g silica Davisil ™ |
| Group IIA metal | barium |
| Method of preparation | deposition precipitation |
| Color of catalyst | pale yellow |

Procedure:

Under a argon atmosphere the microreactor was charged with 200 mg of catalyst and 0.05 g ($8.7*10^{-4}$ mols) of allyl alcohol in 2 ml water the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 20% Olefin was convened to aldehydes with n/i ratio of 1. The catalyst was recovered by washing reactor several times with toluene and catalyst was recovered by centrifugation, washing repeatedly with toluene and diethyl ether. Catalyst was dried under vacuum and recycled to obtain equivalent activity.

Example 439
Hydroformylation of hexene
Catalyst specifications:

| | |
|---|---|
| Catalytic entity | HRhCO(N($Ph_mSO_3^-$)$_3$)$_3$ ($10^{-6}$ mols) |
| Additive | N($Ph_mSO_3^-$)$_3$ 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Under a argon atmosphere the microreactor was charged with 200 mg of catalyst anti 0.5 g ($5.9*10^{-4}$, mol) of hexene in 2 ml toluene the reactor was flushed with $H_2$/CO mixture an reactor was heated to 75° C. and pressurized with $H_2$/CO mixture (1:1 by mole) an maintained at this temperature. Liquid suspension was stirred with external magnetic agitation. Reaction was continued for 24 hours. Analysis of the products confirmed conversion of olefins to aldehydes. 68% Olefin was converted to aldehydes with n/I selectivity of 1.78 the catalyst was recovered by washing reactor several times with toluen and catalyst was recovered by centrifugation, washing repeatedly with toluene and diethyl ether. Catalyst was dried under vacuum and recycled to obtain equivalent activity.

Example 440
Hydroformylation of hexene
Catalyst specifications:

| | |
|---|---|
| Catalytic entity | HRhCO(BISBIS) ($10^{-6}$ mols) |
| Additive | BISBIS 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Under a argon atmosphere the microreactor was charged with 200 mg of catalyst and 0.05 g ($5.9*10^{-4}$ mol) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 78% Olefin was converted to aldehydes with n/I selectivity of 17.88. The catalyst was recovered by washing reactor several times with toluene and catalyst was recovered by centrifugation, washing repeatedly with toluene and diethyl ether. Catalyst was dried under vacuum and recycled to obtain equivalent activity.

Example 441
Hydroformylation of hexene
Catalyst specifications:

| | |
|---|---|
| Catalytic entity | HrhCO(succindiphos) ($10^{-6}$ mols) |
| Additive | succindiphos 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Under a argon atmosphere the microreactor was charged with 200 mg of catalyst and 0.05 g ($5.9*10^{-4}$, mol) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 80% Olefin was converted to aldehydes with n/I selectivity of 0.6. The catalyst was recovered by washing reactor several times with toluene and catalyst was recovered by centrifugation, washing repeatedly with toluene and diethyl ether. Catalyst was dried under vacuum and recycled to obtain equivalent activity.

Example 442
Hydroformylation of hexene
Catalyst specifications:

| | |
|---|---|
| Catalytic entity | HRhCO(bypyds) ($10^{-6}$ mols) |
| Additive | bypyds 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Under a argon atmosphere the microreactor was charged with 200 mg of catalyst and 0.05 g ($5.9*10^{-4}$, mol) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 80% Olefin was converted to aldehydes with n/I selectivity of 0.92. The catalyst was recovered by washing reactor several times with toluene and catalyst was recovered by centrifugation, washing repeatedly with toluene and diethyl ether. Catalyst was dried under vacuum and recycled to obtain equivalent activity.

Example 443
Cobalt catalyzed hydroformylation
Catalyst specifications:

| | |
|---|---|
| Catalytic entity | $(Co(Ac)_2/(P(Ph_mSO_3^-)_3)_3$ ($10^{-6}$ mols) |
| Additive | $P(Ph_mSO_3^-)_3$ 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Under a argon atmosphere the microreactor was charged with 200 mg of catalyst and 0.05 g ($5.9*10^{-4}$, mol) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 30% Olefin was converted to aldehydes with n/i of 1.38. The catalyst was recovered by washing reactor several times with toluene and catalyst was recovered by centrifugation, washing repeatedly with toluene and diethyl ether. Catalyst was dried under vacuum and recycled to obtain equivalent activity.

Example 444
Platinum catalyzed hydroformylation

Preparation of catalysts: heterogenized platinum chloride phosphine complex was boiled with dichloromethane and stannous chloride and subsequently extracted with dichloromethane
Catalyst specifications:

| | |
|---|---|
| Catalytic entity | $SnCl_2PtCl_2(P(Ph_mSO_3^-)_3)_2$ ($10^{-6}$ mols) |
| Additive | $N(Ph_mSO_3^-)_3$ 6* $10^{-6}$ mols/polyvinyl sulfonic acid 100 mg |
| Support | 5 g silica Davisil ™ |
| Group IIA metal salt | barium |
| Method of preparation | deposition precipitation |
| Color of catalyst | pale yellow |

Procedure:

Under a argon atmosphere the microreactor was charged with 200 mg of catalyst and 0.05 g ($5.9*10^{-4}$, mol) of hexene in 2 ml toluene the reactor was flushed with $H_2$/CO mixture and reactor was heated to 75° C. and pressurized with $H_2$/CO mixture (1:1 by mole) and maintained at this temperature. Liquid suspension was stirred with external magnetic agitation. Reaction was continued for 24 hours. Analysis of the products confirmed conversion of olefins to aldehydes. 57% Olefin was converted to aldehydes with n/I selectivity of 10.47. The catalyst was recovered by washing reactor several times with toluene and catalyst was recovered by centrifugation, washing repeatedly with toluene and diethyl ether. Catalyst was dried under vacuum and recycled to obtain equivalent activity.
Carbonylation of styrene
Catalyst specifications:

| | |
|---|---|
| Catalytic entity | $Pd(Ac)_2(P(Ph_mSO_3^-)_2(PySO_3^-))$ ($10^{-6}$ mols) |

| | |
|---|---|
| Additive | (P(Ph$_m$SO$_3^-$)$_2$(PySO$_3^-$) 6* 10$^{-6}$ mols/ polyvinyl sulfonic acid 100 mg |
| Support | 5 g charcoal |
| Group IIA metal salt | barium |
| Method of preparation | deposition precipitation |
| Color of catalyst | Black |
| Metal content | |

Procedure: 15 ml reactor with magnetic stirrer bar was charged with 200 mg catalyst and 500 mg (4.90 10$^{-3}$ mmol) styrene and 5 mg p toluene sulfonic, acid 25 mg N, N, dimethyl aniline and 10 ml methanol. Micro reactor was flushed with argon and pressurized with carbon monoxide 800 psi and mixture was stirred at 70° C. for 24 hours. Reaction mixture was analyzed by gas chromatograph. 87% phenyl acetylene was carbonylated with 99% selectivity for methyl 2-phenyl propionate. Reaction mixture was centrifuged to recover solid catalyst, which was subsequently washed with methanol repeatedly. Catalyst was further washed with diethyl ether and dried under vacuum.

Example 446
Carbonylation of styryl alcohol
Preparation of catalysts
Catalyst specifications:

| | |
|---|---|
| Catalytic entity | Pd(Ac)$_2$(P(Ph$_m$SO$_3^-$)$_2$(PySO$_3^-$)) (10$^{-6}$ mols) |
| Additive | (P(Ph$_m$SO$_3^-$)$_2$(PySO$_3^-$) 6* 10$^{-6}$ mols/polyvinyl sulfonic acid 100 mg |
| Support | 5 g charcoal |
| Group IIA metal salt | barium |
| Method of preparation | deposition precipitation |
| Color of catalyst | Black |

Procedure:

15 ml reactor with magnetic stirrer bar was charged with 200 mg catalyst and 500 mg (8.9*10$^{-3}$ mmol) styryl alcohol and 5 mg p toluene sulfonic, acid and 10 ml methanol. Micro reactor was, flushed with argon and pressurized with carbon monoxide 800 psi and mixture was stirred at 100° C. for 24 hours. Reaction mixture was analyzed by gas chromatograph. 52% phenyl acetylene was carbonylated with 91% selectivity for methyl 2 phenyl propionate over 2-phenyl propionate. Reaction mixture was centrifuged to recover solid catalyst, which was subsequently washed with methanol repeatedly. Catalyst was further washed with diethyl ether and dried under vacuum.

Example 447
Carbonylation of phenyl acetylene
Catalyst specifications:

| | |
|---|---|
| Catalytic entity | Pd(Ac)$_2$(P(Ph$_m$SO$_3^-$)$_2$(PySO$_3^-$)) (10$^{-6}$ mols) |
| Additive | (P(Ph$_m$SO$_3^-$)$_2$(PySO$_3^-$) 6* 10$^{-6}$ mols/ polyvinyl sulfonic acid 100 mg |
| Support | 5 g charcoal |
| Group IIA metal salt | barium |
| Method of preparation | deposition precipitation |
| Color of catalyst | Black |

15 ml reactor with magnetic stirrer bar was charged with 200 mg catalyst and 500 mg (4.90 10$^{-3}$ mmol) phenyl acetylene and 5 mg p toluene sulfonic, acid 25 mg N,N, dimethyl aniline and 10 ml methanol. Micro reactor was, flushed with argon and pressurized with carbon monoxide 100 psi and mixture was stirred at 90° C. for 12 hours. Reaction mixture was analyzed by gas chromatograph. 80% phenyl acetylene was carbonylated with 96% selectivity for methyl dehydroatropate. Reaction mixture was centrifuged to recover solid catalyst, which was subsequently washed with methanol repeatedly. Catalyst was further washed with diethyl ether and dried under vacuum.

Example 448
Hydrogenation of styrene
Catalyst specifications:

| | |
|---|---|
| Catalytic entity | RhClCOD(TPPTS)$_3$ 10$^{-5}$ mols |
| Additive | 10$^{-5}$ mols of tppts/500 mg sodium carboxy methyl cellulose |
| Support | kesilghur |
| Group IIA metal salt | Strontium chloride saturated solution |
| Method of preparation | Deposition precipitation |
| Color of catalyst | Pale yellow |

Procedure:

15 ml reactor with magnetic stirrer bar was charged with 200 mg catalyst and 500 mg (4.8*10$^{-3}$ mmol) styrene in 10 ml ethanol. Micro reactor was flushed with argon and pressurized with hydrogen 500 psi and mixture was stirred at 90° C. for 12 hours. Reaction mixture was analyzed by gas chromatograph. 98% styrene was hydrogenated to ethyl benzene. Reaction mixture was centrifuged to recover solid catalyst, which was subsequently washed with methanol repeatedly. Catalyst was further washed with diethyl ether and dried under vacuum. Catalyst was recycled to obtain equivalent activity

Example 449
Hydrogenation of methyl cinnamate
Catalyst specifications:

| | |
|---|---|
| Catalytic entity | RhClCOD(TPPTS)$_3$ 10$^{-5}$ mols |
| Additive | 10$^{-5}$ mols of tppts/500 mg sodium carboxy methyl cellulose |
| Support | kesilghur |
| Group IIA metal salt | Strontium chloride saturated solution |
| Method of preparation | Deposition precipitation |
| Color of catalyst | Pale yellow |

Procedure:

15 ml reactor with magnetic stirrer bar was charged with 200 mg catalyst and 500 mg (3.08*10$^{-3}$ mmol) methyl cinnamate in 10 ml methanol. Micro reactor was flushed with argon and pressurized with hydrogen 1000 psi and mixture was stirred at 50° C. for 12 hours. Reaction mixture was analyzed by gas chromatograph. 80% methyl cinnamate was hydrogenated to methyl 3 phenyl propionate. Reaction mixture was centrifuged to recover solid catalyst, which was subsequently washed with methanol repeatedly. Catalyst was further washed with diethyl ether and dried under vacuum. Catalyst was recycled to obtain equivalent activity.

Example 450
Hydrogenation of cinnamonitrile
Catalyst specifications:

| | |
|---|---|
| Catalytic entity | RhClCOD(TPPTS)$_3$ 10$^{-5}$ mols |
| Additive | 10$^{-5}$ mols of tppts/500 mg sodium carboxy methyl cellulose |
| Support | Kesilghur |
| Group IIA metal salt | Strontium chloride saturated solution |
| Method of preparation | Deposition precipitation |
| Color of catalyst | Pale yellow |

Procedure:

15 ml reactor with magnetic stirrer bar was charged with 200 mg catalyst and 500 mg (3.87*10$^{-3}$ mmol) cinnamonitrile in 10 ml methanol. Micro reactor was flushed with argon and pressurized with hydrogen 500 psi and mixture was stirred at 50° C. for 12 hours. Reaction mixture was analyzed by gas chromatograph. 79% cinnamonitrile was hydrogenated with 60% selectivity for 3-phenyl propionitrile. Reaction mixture was centrifuged to recover solid catalyst, which was subsequently washed with methanol repeatedly. Catalyst was further washed with diethyl ether and dried under vacuum. Catalyst was recycled to obtain equivalent activity.

Example 451
Hydrogenation of dehydronaproxen
Catalyst specifications:

| | |
|---|---|
| Catalytic entity | BINAPts RuCl$_2$ 10$^{-6}$ mols |
| Additive | BINAPts 10$^{-6}$ mols/500 mg sodium phosphate |
| Support | Silica davisil 1 g |
| Group IIA metal salt | Saturated solution of barium nitrate |
| Method of preparation | Precipitation in coating pan |
| Color of catalyst | Pale yellow |

Procedure:

15 ml reactor with magnetic stirrer bar was charged with 200 mg catalyst and 128 mg (1.26*10$^{-3}$ mol) dehydro naproxen and 128 mg (1.26*10$^{-3}$ mol) methyl amine and 10 ml tolune: methanol (3:2 v/v). Micro reactor was flushed with argon and pressurized with hydrogen 100 bar and mixture was stirred at 0° C. for 48 hours. Reaction mixture was centrifuged to recover solid catalyst, which was subsequently washed with methanol repeatedly. All washings and reaction mixture were combined and dried in vacuum. Solid thus obtained was thus dissolved in dichloromethane and washed with dilute HCl followed by water. Dichloromethane was evaporated to obtain naproxen. Analysis of products: products were analyzed by HPLC with WHELK-O column (produced by Merck) yield of naproxen was 98% and 92% e.e.

Second recycle 98% and e.e. 94%

Example 452
Hydrogenation of heptaldehyde
Catalyst specifications:

| | |
|---|---|
| Catalytic entity | Ru(H)(Cl)(TPPTS)$_3$ (10$^{-6}$ mols) |
| Additive | TPPTS(6 * 10$^{-6}$ mols)/500 mg sodium alginate |
| Support | Titania 5 g |
| Group IIA metal salt | Strontium chloride saturated solution |
| Method of preparation | coprecipitation |
| Color of catalyst | Pale yellow |

Procedure:

100 mg of the catalyst was charged in the microreactor to this 50 mg (4.38*10$^{-4}$ mol) heptaldehyde was added as solution in 2 ml toluene. Microreactor was flushed with argon and heated to 90° C. Magnetic agitation was started. After attaining temperature reactor was pressurized with 500-psi hydrogen. The reactor was maintained under these conditions for 24 hours. Reaction was stopped by cooling reactor to 0° C. and depressurizing. Reactor was opened and liquid was analyzed by gas chromatograph. 99% heptaldehyde was converted.

Catalyst was recovered by washing reactor with several portions of toluene combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 453
Hydrogenation of cinnamaldehyde
Catalyst specifications:

| | |
|---|---|
| Catalytic entity | Ru(H)$_2$ (TPPTS)$_4$ (10$^{-6}$ mols) |
| Additive | TPPTS (6 * 10$^{-6}$ mols)/500 mg sodium alginate |
| Support | Titania 5 g |
| Group IIA metal salt | Strontium chloride saturated solution |
| Method of preparation | coprecipitation |
| Color of catalyst | Pale yellow |

Procedure:

100 mg of the catalyst was charged in the microreactor to this 500 mg (3.78*10$^{-3}$ mol) cinnamaldehyde was added as solution in 2 ml tetrahydrofuran. Microreactor was flushed with argon and heated to 90° C. Magnetic agitation was started. After attaining temperature reactor was pressurized with 500-psi hydrogen. The reactor was maintained under these conditions for 24 hours. Reaction was stopped by cooling reactor to 0° C. and depressurizing. Reactor was opened and liquid was analyzed by gas chromatograph. 88% cinnamaldehyde was converted. Selectivity for cinnamyl alcohol was 73%.

Catalyst was recovered by washing reactor with several portions of tetrahydrofuran combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 454
Hydrogenation of ethyl acetoacetate
Catalyst specifications:

| | |
|---|---|
| Catalytic entity | BINAPts RuCl$_2$ 10$^{-6}$ mols |
| Additive | BINAPts 10$^{-6}$ mols/500 mg sodium phosphate |

| | |
|---|---|
| Support | Silica davisil 1 g |
| Group IIA metal salt | Saturated solution of barium nitrate |
| Method of preparation | Precipitation in coating pan |
| Color of catalyst | Pale yellow |

Procedure:

Procedure: 1 g of the catalyst was charged in the microreactor to this 5 g ethyl 3 oxobutanoate in 15 ml methanol. Resulting suspension was charged in microreactor, which was flushed with argon and hydrogen. Temperature of the reactor was raised to 90° C. and reactor was filled with hydrogen 150 psi. The reactor was maintained under these conditions for 24 hours. Reaction was stopped by cooling reactor to 0° C. and depressurizing. Reactor was opened and liquid was analyzed by gas chromatograph. Ethyl 3 oxobutanoate was quantitatively converted to corresponding alcohol. Catalyst was recovered by washing reactor with several portions of methanol. Combined fractions were fractionated to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Optical purity of product by fresh catalyst is 42% and recycled catalyst is 94%

Example 455
Hydrogenation of benzyledene acetone
Catalyst specifications:

| | |
|---|---|
| Catalytic entity | Rh(ClO$_4^-$)(CODl)(TPPTS)$_3$ (10$^{-6}$ mols) |
| Additive | TPPTS (6 * 10$^{-6}$ mols)/500 mg sodium alginate |
| Support | zirconia 5 g |
| Group IIA metal salt | Strontium chloride saturated solution |
| Method of preparation | coprecipitation |
| Color of catalyst | Pale yellow |

Procedure: Procedure:

100 mg of the catalyst was charged in the microreactor to this 500 mg (3.42*10$^{-3}$ mol) benzyledene acetone was added as solution in 2 ml tetrahydrofuran Microreactor was flushed with argon and heated to 90° C. Magnetic agitation was started. After attaining temperature reactor was pressurized with 500-psi hydrogen. The reactor was maintained under these conditions for 24 hours. Reactor was stopped by cooling reactor to 0° C. and depressurizing Reactor was opened and liquid was analyzed by gas chromatograph. Total benzyledene acetone was converted. Catalyst was recovered by wasting reactor with several portions of tetrahydrofuran combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 456
Nitrotolune hydrogenation
Catalyst specifications:

| | |
|---|---|
| Catalytic entity | Ru(Cl)(μCl)(TPPTS)$_2$ (10$^{-6}$ mols) |
| Additive | TPPTS (6 * 10$^{-6}$ mols)/500 mg sodium alginate |
| Support | Titania 5 g |
| Group IIA metal salt | Strontium chloride saturated solution |
| Method of preparation | coprecipitation |
| Color of catalyst | Pale yellow |

Procedure:

100 mg of the catalyst was charged in the microreactor to this 500 mg (3.649*10$^{-3}$ mol) o-nitro toluene was added as solution in 2 ml ethyl acetate. Microreactor was flushed with argon and heated to 90° C., magnetic agitation was started. After attaining temperature reactor was pressurized with 500-psi hydrogen. The reactor was maintained under these conditions for 24 hours. Reaction was stopped by cooling reactor to 0° C. and depressurizing. Reactor was opened and liquid was analyzed by gas chromatograph. Total o-Nitrotolune was converted to o toludene.

Catalyst was recovered by wasting reactor with several portions of ethyl acetate combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 457
Hydrogenation o-chloro nitro benzene
Catalyst specifications:

| | |
|---|---|
| Catalytic entity | Ru(Cl)(μCl)(TPPTS)$_2$ (10$^{-6}$ mols) |
| Additive | TPPTS (6 * 10$^{-6}$ mols)/500 mg sodium alginate |
| Support | Titania 5 g |
| Group IIA metal salt | Strontium chloride saturated solution |
| Method of preparation | Coprecipitation |
| Color of catalyst | Pale yellow |

Procedure:

100 mg of the catalyst was charged in the microreactor to this 500 mg (3.952*10$^{-3}$ mol) o-chloro nitrobenzene was added as solution in 2 ml ethyl acetate. Microreactor was flushed with argon and heated to 90° C. Magnetic agitation was started. After attaining temperature reactor was pressurized with 500-psi hydrogen. The reactor was maintained under these conditions for 24 hours. Reaction was stopped by cooling reactor to 0° C. and depressurizing. Reactor was opened and liquid was analyzed by gas chromatograph. Total o-chloro nitrobenzene was converted to o chloro aniline.

Catalyst was recovered by washing reactor with several portions of ethyl acetate combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 458
Iodobenzene and methyl acrylate
Catalyst specifications:

| | |
|---|---|
| Catalytic entity | Pd$^0$(P(Ph$_m$SO$_3^-$)$_3$)$_3$ (10$^{-5}$ mols) |
| Additive | P(Ph$_m$SO$_3^-$)$_3$ (4 * 10$^{-5}$ mols) |
| Support | Charcoal 1 g |
| Group IIA metal salt | Barium nitrate saturated solution |

-continued

| | |
|---|---|
| Method of preparation | Deposition precipitation |
| Color of catalyst | Black |

Procedure:

procedure: procedure: procedure: 100 mg of the catalyst was charged in the microreactor to this 1 mg tetrabutyl ammonium hydroxide, 0.41 mg ($5*10^{-3}$) sodium acetate 0.5 g ($5*10^{-3}$) ethyl acrylate and 0.509 g ($2.5*10^{-3}$) iodobenzene was added as solution in 5 ml toluene. Microreactor was flushed with argon and heated to 90° C., magnetic agitation was started after attaining temperature. The reactor was maintained under these conditions for 48 hours. Reaction was stopped by cooling reactor to 0° C. and depressurizing. Reactor was opened and liquid was analyzed by gas chromatograph. 86% ethyl acrylate was converted to products. Catalyst was recovered by washing reactor with several portions of toluene combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity. Observation color of the recovered catalyst was dark yellow.

Example 459
Iodobenzene and acrylonitrile
Catalyst specifications:

| | |
|---|---|
| Catalytic entity | $Pd^0(P(Ph_mSO_3^-)_3)_3$ ($10^{-5}$ mols) |
| Additive | $P(Ph_mSO_3^-)_3$ ($4 * 10^{-5}$ mols) |
| Support | Charcoal 1 g |
| Group IIA metal salt | Barium nitrate saturated solution |
| Method of preparation | Deposition precipitation |
| Color of catalyst | Black |

Procedure:

procedure: procedure: procedure: 100 mg of the catalyst was charged in the microreactor to this 1 mg tetrabutyl ammonium hydroxide, 0.41 g sodium acetate, 0.265 g ($5*10^{-3}$) acrylonitrile and 0.509 g ($2.5*10^{-3}$) iodobenzene was added as a solution in 5 ml toluene. Microreactor was flushed with argon and heated to 90° C. Magnetic agitation was started after attaining temperature. The reactor was maintained under these conditions for 48 hours. Reaction was stopped by cooling reactor to 0° C. and depressurizing. Reactor was opened and liquid was analyzed by gas chromatograph. 90% acrylonitrile was convened to products.

Catalyst was recovered by washing reactor with several portions of toluene combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.
Observation color of the recovered catalyst was dark yellow.

Example 460
Iodobenzene and styrene
Catalyst specifications:

| | |
|---|---|
| Catalytic entity | $Pd^0(P(Ph_mSO_3^-)_3)_3$ ($10^{-5}$ mols) |
| Additive | $P(Ph_mSO_3^-)_3$ ($4 * 10^{-5}$ mols) |
| Support | Charcoal 1 g |

-continued

| | |
|---|---|
| Group IIA metal salt | Barium nitrate saturated solution |
| Method of preparation | Deposition precipitation |
| Color of catalyst | Black |

Procedure:

1 g of the catalyst was charged in the microreactor to this 5 mg tetrabutyl ammonium hydroxide, 0.66 mg potassium carbonate 0.5 g ($4.8*10^{-3}$ mol) styrene and 1.957 g ($9.6*10^{-3}$ mol) iodobenzene was added as solution in 10 ml toluene. Microreactor was flushed with argon and heated to 90° C. Magnetic agitation was started after attaining temperature. The reactor was maintained under these conditions for 76 hours. Reaction was stopped by cooling reactor to 0° C. Reactor was opened and liquid was analyzed by gas chromatograph. 44% styrene was converted to stilbene.

Catalyst was recovered by washing reactor with several portions of toluene combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 461
Iodobenzene and ethylene
Catalyst specifications:

| | |
|---|---|
| Catalytic entity | $Pd(Ac)_2(P(o\ Me-Ph_mSO_3^-)_3)_2$ ($10^{-5}$ mols) |
| Additive | $(P(o\ Me-Ph_mSO_3^-)_3)_2$ ($4 * 10^{-5}$ mols) |
| Support | Charcoal 1 g |
| Group IIA metal salt | Barium nitrate saturated solution |
| Method of preparation | Deposition precipitation |
| Color of catalyst | Black |

Procedure:

100 mg of the catalyst was charged in the microreactor to this 1 mg tetrabutyl ammonium hydroxide 0.41 g sodium acetate and 0.509 g ($2.5*10^{-3}$) iodobenzene was added as solution in 10 ml acetonitrile Microreactor was flushed with nitrogen and heated to 120° C. Reactor was pressurized with ethylene and magnetic agitation was started. The reactor was maintained under these conditions for 75 hours. Reaction was stopped by cooling reactor to 0° C. Reactor was depressurized by venting gas in the reactor. Reactor was opened and liquid was analyzed by gas chromatograph. 30% iodobenzene was converted to styrene.

Catalyst was recovered by washing reactor with several portions of toluene combined fractions were centrifuged to recover catalyst. Recovered catalyst was washed with water, methanol and diethyl ether and catalyst was dried under vacuum. This catalyst was recycled to obtain equivalent activity and selectivity. Catalyst was recycled to obtain equivalent conversion and selectivity.

Example 462
Bromo benzene and o tolyl boronic acid
Catalyst specifications:

| | |
|---|---|
| Catalytic entity | $Pd^0(P(Ph_mSO_3^-)_3)_3$ ($10^{-5}$ mols) |
| Additive | $P(Ph_mSO_3^-)_3$ ($4 * 10^{-5}$ mols) |
| Support | Charcoal 1 g |
| Group IIA metal salt | Barium nitrate saturated solution |
| Method of preparation | Deposition precipitation |

| | |
|---|---|
| Color of catalyst | Black |

Procedure:

Thoroughly dried 500-ml flask was equipped with thermometer, magnetic stirrer bar, condenser, addition funnel and two-way valve. To the flask was placed 12.2 g (0.5 atom) of magnesium turnings. Assembly was thoroughly evacuated through two-way valve and nitrogen was filled and magnesium was stirred for 6 hours. To this was added a crystal of iodine, 100 ml of tetrahydrofuran distilled over sodium benzophenone ketyl and 200 µl of 1,2 dibromoethane. After surface of magnesium turns shiny white 78.5-g (0.5 mol) bromobenzene was added with such a rate that temperature raises to boiling. Reaction was continued with intermittent cooling of the flask by removing heater-stirrer. Once reaction subsides mixture was refluxed until magnesium was dissolved. Reaction mixture was transferred to Schlenk tube plugged with glass wool. m-tolyl boronic acid To a thoroughly dried flanged flask attached with scaled mechanical stuffing box and a dropping funnel and reflux condenser attached with fused calcium chloride guard tubes was assembled. Temperature of the flask was brought to −75° C. with acetone and liquid nitrogen. To the flask was added 40.5 g of tributyl borate in 150-ml ether. With fairly rapid stirring add solution of o tolyl magnesium bromide without letting temperature to rise above −70° C. continue stirring for three hours at same temperature. Temperature of the flask was maintained to 5° C. with ice bath for 12 hours. This reaction mixture was added to chilled 10% sulfuric acid 150 ml. Extract with ether and evaporated to this was added 100 ml water and basified with NaOH to slightly alkaline. Acidify and extract with boiling water and collected as crystalline material (5 g).

1 g of the catalyst was charged in the round-bottomed flask attached to reflux condenser, magnetic bar was added to round bottomed flask. To this 1-mg tetrabutyl ammonium hydroxide, 75 mg, sodium carbonate, 0.136-g ($10^{-3}$ mols) o-tolyl boronic acid and 0.224 g ($1.1*10^{-3}$) iodobenzene was added as solution in 20 ml toluene. Assembly was flushed with nitrogen and heated to 90° C. The reactor was maintained under these conditions for 24 hours. Reaction was stopped by cooling reactor to 0° C. Liquid was analyzed by gas chromatograph. 95% iodobenzene was converted to 2 methyl 1, 1' biphenyl.

Catalyst was recovered by washing reactor with several portions of toluene combined fractions were centrifuged to recover catalyst. Recovered catalyst was washed with sodium carbonate, water, methanol and diethyl ether and catalyst was dried under vacuum. This catalyst was recycled to obtain equivalent activity and selectivity. Catalyst was recycled to obtain equivalent conversion and selectivity.

Example 463

Phenyl magnesium bromide and iodobenzene
Catalyst specifications:

| | |
|---|---|
| Catalytic entity | NiCl$_2$.dppe ts (5 * $10^{-3}$ atom of nickel) |
| Additive | Dppe 0.806 mg |
| Support | Silica davisil |
| Group IIA metal salt | Barium nitrate saturated solution |
| Method of preparation | Fluidized bed |
| Color of catalyst | Pale blue |
| Moisture content | Not detectable by Karl Fischer |

Procedure:
Preparation of Grignard reagent

Thoroughly dried 500-ml flask was equipped with thermometer, magnetic stirrer bar, condenser, addition funnel and two-way valve. To the flask was placed 0.61 g (0.025 atom) g of magnesium turnings. Assembly was thoroughly evacuated through two-way valve and nitrogen was filled and magnesium was stirred for 6 hours. To this was added a crystal of iodine, 50 ml of tetrahydrofuran distilled over sodium benzophenone ketyl and 200 µl of 1,2 dibromoethane. After surface of magnesium turns shiny white 3.922-g (0.025 mol) bromobenzene in 20-ml uhf was added with such a rate that temperature raises to boiling. Reaction was continued with intermittent cooling of the flask by removing heater-stirrer. Once reaction, subsides mixture was refluxed until magnesium was dissolved. Reaction mixture was transferred to Schlenk tube plugged with glass wool.

Thoroughly dried 250 ml flask was equipped with thermometer, magnetic stirrer bar, condenser, addition funnel and two way valve was charged with 5 g of catalyst, 50 ml tetrahydrofuran freshly distilled over sodium benzophenone ketyl of blue color. Assembly was filled with nitrogen as described earlier. To this was added 5.09 g (0.025 mol of iodobenzene) 60 ml Grignard reagent as prepared previously was charged in addition vessel. Grignard reagent was slowly added to contents of the flask which was previously cooled to 5° C. Temperature of the flask was maintained at 5° C. for 24 h. Reaction mixture was cooled to room temperature to which was slowly added 20 ml water followed by saturated 20 ml ammonium chloride. Resulting suspension was fluttered to remove solids and subsequently washed thoroughly with tetrahydrofuran and water. Filtrates were extracted with dichloromethane to obtain biphenyl in 89% yield residue left after filtration was washed with water, tetrahydrofuran and ether and dried under vacuum.

Example 464

Isotubyl magnesium bromide and iodobenzene
Preparation of catalysts: catalyst was previously dried by extraction with boiling THF over sodium wire followed by vacuum and stored over phosphorus pentoxide catalyst specifications:

| | |
|---|---|
| Catalytic entity | NiCl$_2$.dppe ts (5 * $10^{-3}$ atom of nickel) |
| Additive | Dppe 0.806 mg |
| Support | Silica davisil 5 g |
| Group IIA metal salt | Barium nitrate saturated solution |
| Method of preparation | Fluidized bed |
| Color of catalyst | Pale blue |
| Moisture content | Not detectable by Karl Fischer |

Procedure: preparation of Grignard reagent condenser, addition funnel and two-way valve. To the flask was placed 2.44 g (0.1 atom) of magnesium turnings. Assembly was thoroughly evacuated through two-way valve and nitrogen was filled and magnesium was stirred for 6 hours. To this was added a crystal of iodine, 50 ml of tetrahydrofuran distilled over sodium benzophenone ketyl and 200 µl of 1,2 dibromoethane. After surface of magnesium turns shiny white 9.2-g (0.1 mol) isobutyl bromide was added with such a rate that temperature raises to boiling. Reaction was continued with intermittent cooling of the flask by removing heater-stirrer. Once reaction subsides mixture was refluxed until magnesium was dissolved. Reaction mixture was transferred to Shlenk tube using canula plugged with glass wool.

Thoroughly dried 500 ml flask was equipped with thermometer, magnetic stirrer bar, condenser, addition funnel and two way valve was charged with 5 g of catalyst, 50-ml terahydrofuran freshly distilled over sodium benzophenone ketyl of blue color. Assembly was filled with nitrogen as described earlier. To this was added 20.39 g (0.1 mol of iodobenzene) 50 ml Grignard reagent as prepared previously was charged in addition vessel. Grignard reagent was slowly added to contents of the flask which were cooled to 0° C. Temperature of the flask was raised to 50-0 C. temperatures. Reaction mixture was cooled to room temperature to, which was slowly added 25-ml water followed by 25 ml saturated ammonium chloride. Resulting suspension was filtered to remove solids and subsequently washed thoroughly with tetrahydrofuran and water. Filtrates were extracted with dichloromethane to obtain isobutyl benzene in 92% yield residue left after filtration was washed with water, thf and ether and dried under vacuum.

Example 465
Allylation of aryl boronates
Catalyst specifications:

| Catalytic entity | $NiCl_2.(tppts)_2$ (96.5 mg($10^{-4}$ mols) |
| --- | --- |
| Additive | tppts(83.6 mg(2 * $10^{-4}$ mols) |
| Support | Silica davisil 2 g |
| Group IIA metal salt | Barium nitrate saturated solution |
| Method of preparation | Fluidized bed |
| Color of catalyst | White with blue ting |
| Moisture content | Not detectable by Karl Fischer |

Procedure:

to a 2 gm of catalyst was added 20 ml of tetrahydrofuran, to this solution was added 5 ml of cold solution containing 2.9 mmol of phenyl lithium. The mixture was cooled to 0° C. under stirring and to this 0.42 ml (3.62 mmol) $B(OCH_3)_3$ was slowly added followed by 1.44 mmol allyl methyl carbonate. Temperature was then raised to 60° C. and reaction was continued for 12 hours. Liquid was separated from solid catalyst and poured in to a mixture of 20 ml of hexane and 20 ml of saturated ammonium chloride. Organic layer indicated formation of 3-phenyl propene.

Recovered catalyst was washed with saturated bicarbonate, tetrahydrofuran and diethyl ether and recycled after drying in vacuum.

Example 466
Hexane isomarization
Catalyst specifications:

| Catalytic entity | $Rh^+(ClO_4^-)(tppts)_3$ |
| --- | --- |
| Additive | tppts |
| Support | silica |
| Group IIA metal salt | Saturated barium nitrate solution |
| Method of preparation | Deposition precipitation |
| Color of catalyst | Pale yellow |

Procedure:

Isomerization was carried out according following procedure. 5 gm of catalyst was charged in microreactor, which was subsequently flushed with nitrogen and charged with degassed mixture of 5 g 1-hexene (92% purity), and 45-ml cyclohexane. Temperature of the reactor was raised to 100° C. and maintained for 76 hours. Conversion of 1 hexene was 73%. And two isomarized products were observed. Catalyst was centrifuged and liquid was separated. Catalyst was repeatedly washed by cyclohexane. Isolated catalyst was recycled under identical conditions to provide equivalent yields.

Example 467
N,N-Diethylneryl amine isomerization
Catalyst specifications:

| Catalytic entity | $Rh^+(ClO_4^-)(binapts)_3$ ($10^{-6}$ mol) |
| --- | --- |
| Additive | Binapts (5 * $10^{-6}$ mol) |
| Support | Silica 2 g |
| Group IIA metal salt | Saturated barium nitrate solution |
| Method of preparation | Deposition precipitation |
| Color of catalyst | Pale yellow |

Procedure: catalyst drying

Isomerization was carried out as per procedure adopted from (Helvetica Chemica Acta vol.1, (1988) 897–920) modified to suit solid catalyst. 2 gm of catalyst was charged in Fischer-porter bottle and evacuated. Bottle was subsequently flushed with nitrogen and charged with degassed mixture of 11.37 g (50 mmol) (purity by area % on gc 92) N,N-Diethylneryl amine and 50 ml dry tetrahydrofuran. Temperature of the bottle was raised to 80° C. and maintained for 76 hours. Catalyst was centrifuged and liquid was separated. Repeated washings of catalyst by tetrahydrofuran were combined and evaporated to obtain pale yellow oil which was dissolved in 50% acetic acid in water 50 ml at 0° C. stirred for 10 min and 50 ml hexane was added and liquid was stirred for 30 min at ambient temperature. Hexane layer was separated and aqueous layer was washed with hexane hexane extract was washed with sat bicarbonate solution. Fractionation of extract provided 7.35 g (S) citronellol 90% based on N,N-Diethylneryl amine. Optical purity of this material found by polarimetry c=5, $CHCl_3$, lamp D at 20° C. was 98%, isolated catalyst was recycled under identical conditions to provide equivalent yields.

Example 468
1,4-diacetoxy butane isomarization
Catalyst specifications:

| Catalytic entity | $ClO_4^-Rh^+[P(Ph_mSO_3^-)_3]_3(10^{-6})$ |
| --- | --- |
| Additive | $P(Ph_mSO_3^-)_3(6 * 10^{-6})$ |
| Support | Bentonite 5 g |
| Group IIA metal salt | Strontium chloride |
| Method of preparation | Deposition precipitation in coating pan |
| Color of catalyst | Pale yellow |
| Metal content | |

Procedure:

isomerization was carried out according following procedure. 100 mg of catalyst was charged in microreactor which was subsequently flushed with nitrogen and charged with degassed mixture of 50 mg ($3*10^{-4}$ mol), 1,4-diacetoxy butene and 2 ml toluene. Temperature of the reactor was raised to 100° C. and maintained for 76 hours. Catalyst was centrifuged and liquid was separated. Repeated washings of catalyst by toluene. Conversion of 1,4-diacetoxy butene was 57%. Isolated catalyst was recycled under identical conditions to provide equivalent yields.

Example 469
Hexene wacker
Catalyst specifications:

| Palladium acetate/bypyridyldisulfonate | 22.4.mg:55 mg |
| --- | --- |
| bypyridyldisulfonate | 218.4 mg(0.4 mmol) |

-continued

| | |
|---|---|
| Support | Bentonite 2 gm |
| Group IIA metal salt | Strontium chloride |
| Method of preparation | Deposition precipitation by azeotropic removal of water |
| Color of catalyst | Light yellow orange |
| Metal content | 0.46 miliatoms pre gm |

Procedure:

100 mg of the catalyst was charged in the microreactor to this 1 ml hexene was added at 20% v/v solution in hexane. Microreactor was pressurized with air (450 psi) and heated to 90° C. Magnetic agitation was started after attaining temperature. The reactor was maintained for 24 hours. Reaction was stopped by cooling reactor to 0° C. and depressurizing. Reactor was opened and liquid was analyzed by gas chromatograph. 36% cyclohexene was converted to products with 90% selectivity for hexane 2 one. Remainder products were estimated to be isomarized olefins and some unidentified products.

Catalyst was recovered by washing reactor with several portions of cyclohexane combined fractions were centrifuged to recover catalyst. Recovered catalyst was fortified with water to contain 50% water by weight. This catalyst was recycled to obtain equivalent activity and selectivity. Observation color of the recovered catalyst was dark yellow.

Example 470
Decene wacker
Catalyst specifications:

| | |
|---|---|
| Palladium acetate/bypyridyldisulfonate | 22.4.mg:55 mg |
| bypyridyldisulfonate | 218.4 mg(0.4 mmol) |
| Support | Bentonite 2 gm |
| Group IIA metal salt | Strontium chloride |
| Method of preparation | Deposition precipitation by azeotropic removal of water |
| Color of catalyst | Light yellow orange |
| Metal content | 0.46 miliatoms pre gm |

Procedure:

procedure: 100 mg of the catalyst was charged in the microreactor to this 1 ml decene was added as 20% solution in hexene. Microreactor was pressurized with air (450 psi) and heated to 90° C. Magnetic agitation was started after attaining temperature. The reactor was maintained for 24 hours. Reaction was stopped by cooling reactor to 0° C. and depressurizing. Reactor was opened and liquid was analyzed by gas chromatograph. 19% decene was converted to products with 87% selectivity for decane 2 one. Remainder products were estimated to be isomarized olefins and some unidentified products. Catalyst was recovered by washing reactor with several portions of cyclohexane combined fractions were centrifuged to recover catalyst. Recovered catalyst was fortified with water to contain 50% water by weight. This catalyst was recycled to obtain equivalent activity and selectivity. Observation color of the recovered catalyst was dark yellow.

Example 471
Cyclohexene wacker
Catalyst specifications:

| | |
|---|---|
| Palladium acetate/bypyridyldisulfonate | 22.4.mg:55 mg |
| bypyridyldisulfonate | 218.4 mg(0.4 mmol) |
| Support | Bentonite 2 gm |
| Group IIA metal salt | Strontium chloride |
| Method of preparation | Deposition precipitation by azeotropic removal of water |
| Color of catalyst | Light yellow orange |
| Metal content | 0.46 miliatoms per gm |

Procedure:

100 mg of the catalyst was charged in the microreactor to this 1 ml cyclohexene was added as 20% solution in hexene. Microreactor was pressurized with air (450 psi) and heated to 90° C. Magnetic agitation was started after attaining temperature. The reactor was maintained for 24 hours. Reaction was stopped by cooling reactor to 0° C. and depressurized. Reactor was opened and liquid was analyzed by gas chromatograph. 7% cyclohexene was converted to products with 30% selectivity for cyclohexanone. Remainder products were not estimated. Catalyst was recovered by washing reactor with several portions of cyclohexane combined fractions were centrifuged to recover catalyst. Recovered catalyst was fortified with water to contain 50% water by weight. This catalyst was recycled to obtain equivalent activity and selectivity. Observation color of the recovered catalyst was dark yellow.

Example 472
Styrene expoxidation
Preparation of catalysts:

$Ph(CH_2)$-$N^+(Ph_mSO_3^-)_3$.$OH^-$ was heterogenized as described according method described earlier as deposition precipitation in coating pan. Solid was suspended in water to which three mole equivalent of $OH^-$ present (estimated by titration with standard acid) suspension was stirred for 4 hours at 70° C. Solid was recovered and extracted with water for 12 hours followed by drying in vacuum.

Catalyst specifications:

| | |
|---|---|
| Catalytic entity | $Ph(CH_2)$—$N^+(Ph_mSO_3^-)_3$.$MO_4^{-2}$(1 mili eq of $MO_4^{-2}$) |
| additive | Sodium meta silicate 1 gm |
| Support | keisulghur 5 gm |
| Group IIA metal salt | Barium hydroxide saturated solution in water. |
| Method of preparation | Deposition precipitation in coating pan |
| Moisture content | 20% by weight. |

Procedure:

5 g of the catalyst was charged in the 500 ml glass reaction vessel equipped with mechanical stirrer, thermometer pocket and addition vessel, to this 30 g (0.29 mol) styrene in 75 ml acetic acid was added. Reaction vessel was cooled to 5° C. with circulating fluid cryostat. Agitation was started after attaining temperature. 30 ml 34% hydrogen peroxide was added over the period of 30 min. temperature and agitation of the reaction vessel was maintained for 24 hours. Reactor was opened and liquid was analyzed by gas chromatograph. 72% styrene was converted to products with 89% selectivity for styrene oxide. Remainder products were not estimated.

Catalyst was recovered by washing reactor with several portions of acetic acid combined fractions were centrifuged to recover catalyst. Recovered catalyst was washed with methanol, ether and dried. This catalyst was recycled to obtain equivalent activity and selectivity.

Example 473
Chlorophenol oxidation
Preparation of catalysts:
catalyst was prepared according to method described as precipitation in fluidized bed.
Catalyst specifications:

| | |
|---|---|
| Catalytic entity | Iron(III) pthalocynine-4,4',4'', 4'''-tetrasulfonic acid tetrasodium salt as compound with oxygen 30.2 mg ($3 * 10^{-3}$ mols) |
| Additive | Sodium silicate 500 mg |
| Support | Fullers earth 2 g |
| Group IIA metal salt | Barium nitrate saturated solution in water |
| Method of preparation | Fluidized bed drier |
| Color of catalyst | Pale blue |
| Moisture content | 10% by weight |

Procedure:
to a 50 ml round bottom flask attached with a reflux condenser was added 5 ml acetonitrile and 15 ml 0.1 M acetate buffer of pH 7 to which was added 181 mg ($10^{-3}$ mols) of trichloro phenol. 2.5 g catalyst was added and suspension was stirred with magnetic needle. Temperature of the suspension was raised to 60° C. To this 0.3 ml 34% $H_2O_2$ in water was added to above suspension. The reaction mixture was continued for 5 hours. Total disappearance of trichlorophenol was observed and chloride ions were detected in solution with silver nitrate solution.

Example 474
Condensation of diethylfumarate and diethylmalonate to propane-1,1,2,3 tetracarboxylate
Catalyst specifications:

| | |
|---|---|
| Catalytic entity | $Ph(CH_2)-N^+(Ph_mSO_3^-)_3.EtO^-$ (1 milieq of $EtO^-$) |
| additive | Sodium meta silicate 1 gm |
| Support | Charcoal 5 gm |
| Group IIA metal salt | Barium hydroxide |
| Method of preparation | Deposition precipitation |

Procedure:
in a 100-ml flask fitted with an efficient reflux condenser, magnetic stirrer bar and dropping funnel was charged 5 gm of catalyst. With stirring 1.6 g (0.001 mol) diethylmalonate and 25 ml dry ethanol was added. Reaction mixture was warmed and 1.4 gm (0.0081 mol) diethyl fumarate was added. Mixture was refluxed for 8 hours. Reaction mixture was cooled and suspension was centrifuged to recover catalysts. Analysis of reaction liquid indicated 90% conversion for diethulmalonate. Product was distilled under vacuum 8 mm at 180–190° C. to obtain propane-1,1,2,3 tetracarboxylate 85% yield.
Catalyst was recovered and washed with ethanol, diethyl ether and dried under vacuum.
Catalyst was recycled to obtain equivalent activity.

Example 475
Diethylmalonate and formaldehyde condensation to tetraethylpropane-1,1,3,3-tetracarboxylate
Catalyst specifications:

| | |
|---|---|
| Catalytic entity | $Ph(CH_2)-N^+(Ph_mSO_3^-)_3.HO^-$ (1 milieq of $HO^-$) |
| additive | Sodium meta silicate 1 gm |
| Support | Charcoal 5 gm |
| Group IIA metal salt | Barium hydroxide |
| Method of preparation | Deposition precipitation |

Procedure:
mixture of 1.6 g (0.001 mol) of distilled diethyl malonate, 25 ml ethanol and 0.4 g ($5*10^{-4}$ mol) of 40% formaldehyde contained in 50 ml rounded bottom flask was cooled to 0° C. and 5 gm of catalyst was added and mixture was stirred at room temperature for 24 hours and then refluxed for 12 hours. Suspension was centrifuged to recover catalyst. Analysis of reaction liquid indicated 80% conversion of diethyl malonate. Liquid was evaporated and extracted with diethyl ether. Extract was dried with sodium sulfate. Catalyst was washed with ethanol, diethyl ether and dried under vacuum. Catalyst was recycled to obtain equivalent activity.

Example 476
Condensation of acetone and chloroform to chlorbutol
Catalyst specifications:

| | |
|---|---|
| Catalytic entity | $Ph(CH_2)-N^+(Ph_mSO_3^-)_3.OH^-$ (1 milieq of $OH^-$) 0.659 mg |
| additive | Sodium meta silicate 1 gm |
| Support | Charcoal 5 gm |
| Group IIA metal salt | Barium hydroxide |
| Method of preparation | Deposition precipitation |

Procedure:
100 ml round bottomed flask equipped with reflux condenser was charged with 5 gm of catalyst to which solution of 1.19 g (0.01 mol) chloroform was charged as solution in 25 ml solution in acetone. Magnetic stirrer bar was added in the reaction mixture reaction mixture was stirred at ambient temperature for 24 hours. Suspension was centrifuged to recover catalyst. Analysis of reaction liquid indicated total conversion of chloroform. Catalyst was washed with ethanol, diethyl ether and dried under vacuum. Catalyst was recycled to obtain equivalent activity.

Example 477
Condensation of benzaldehyde and acetonitrile to cinnamonitrile.
Catalyst specifications:

| | |
|---|---|
| Catalytic entity | $Ph(CH_2)-N^+(CH_2Ph_mSO_3^-)_3.OH^-$ (1 milieq of $OH^-$) 0.701 mg |
| Additive | Sodium meta silicate 1 gm |
| Support | Charcoal 5 gm |
| Group IIA metal salt | Barium hydroxide |
| Method of preparation | Deposition precipitation |

Procedure:
250 ml round bottomed flask equipped with reflux condenser was charged with 5 gm of catalyst to which solution of 10.6 g (0.1 mol) benzaldehyde was charged as solution in 100 ml solution in acetonitrile. Magnetic stirrer bar was added in the reaction mixture reaction mixture was stirred at reflux temperature for 24 hours. Suspension was centrifuged to recover catalyst. Analysis of reaction liquid indicated 88% conversion of benzaldehyde and 98% selectivity for cinamonitrile. Cinamonitrile was recovered by fractional distillation 80% based on benzaldehyde.
Catalyst was washed with ethanol, diethyl ether and dried under vacuum. Catalyst was recycled to obtain equivlaent activity.

Example 478
Condensation of benzaldehyde and acetone to benzayledene acetone
Catalyst specifications:

| | |
|---|---|
| Catalytic entity | Ph(CH$_2$)—N$^+$(CH$_2$Ph$_m$SO$_3^-$)$_3$.OH$^-$ (1 milieq of OH$^-$) 0.701 mg |
| additive | Sodium meta silicate 1 gm |
| Support | Charcoal 5 gm |
| Group IIA metal salt | Barium hydroxide |
| Method of preparation | Deposition precipitation |

Procedure:

250 ml round bottom flask equipped with reflux condenser was charged with 5 gm of catalyst to which solution of 10.6 g (0.1 mmol) benzaldehyde was charged as solution in 100 ml solution in acetone. Magnetic stirrer bar was added in the reaction mixture reaction mixture was stirred at ambient temperature for 24 hours. Suspension was centrifuged to recover catalyst. Analysis of reaction liquid indicated 77% conversion benzaldehyde. Catalyst was washed with ethanol, diethyl ether and dried under vacuum. Catalyst was recycled to obtain equivalent activity.

Example 479
Condensation of butaraldehyde to 2ethyl hexenal
Catalyst specifications:

| | |
|---|---|
| Catalytic entity | Ph(CH$_2$)—N$^+$(Ph$_m$SO$_3^-$)$_3$.OH$^-$ (1 milieq of OH$^-$) 0.659 mg |
| Additive | Sodium meta silicate 1 gm |
| Support | Charcoal 5 gm |
| Group IIA metal salt | Barium hydroxide |
| Method of preparation | Deposition precipitation |

Procedure:

100 ml round bottomed flask equipped with reflux condenser was charged with 5 gm of catalyst to which solution of 7.2 g (0.1 mmol) butaraldehyde was charged as solution in 50 ml solution in toluene. Magnetic stirrer bar was added in the reaction mixture reaction mixture was refluxed for 24 hours. Suspension was centrifuged to recover catalyst. Analysis of reaction liquid indicated 90% conversion of butaraldehyde. Catalyst was washed with ethanol, diethyl ether and dried under vacuum. Catalyst was recycled to obtain equivalent activity.

Example 480
Iodobenzene phosphination catalyst specifications:

| | |
|---|---|
| Catalytic entity | NiCl$_2$.(bisdiphenylphosphinoethane tetrasulfonate)[1 miliatom of nickel] |
| Additive | bisdiphenylphosphinoethane tetrasulfonate 1 gm. |
| support | γ-alumina 5 gm |
| Cured with | Barium nitrate |
| Method of preparation | Deposition precipitation in coating pan |
| Color of catalyst | Pale yellow |
| Metal content of prepared catalyst | 0.93 miliatom of nickel |

Procedure:

round bottomed flask equipped with reflux condenser was charged with catalyst 5 gm. To this solution of diphenyl phosphine 1 ml (5.75 mmol) in 30 ml dry degassed dimethylformamide was added at room temperature. Suspension was degassed with repetitive vacuum and argon flushing. After heating to 100° C. for 30 min. 10 mmol (2.04 gm.) iodobenzene and 20 mmol (2.25 gm) diazabicyclooctane in 30 ml dimethylformamide was added and resulting solution was maintained at 100° C. Three additional portions of 1-ml diphenyl phosphine each were added at 12-hour interval thereafter. Reaction was continued for 76 hours. Reaction was stopped by cooling flask to room temperature. Catalyst was recovered by centrifugation and washed by dimethylformamide. Filtrates were combined and evaporated to obtain sticky residue, which was diluted with 50-ml tetrahydrofuran. Solution was analyzed with 31 P NMR. Following compounds were detected triphenylphosphine, triphenylphosphine oxide, diphenylphosphine and diphenylphosphineoxide.

Yield of triphenylphosphine based on iodobenzene was 92%; conversion of iodobenzene was complete as confirmed by gas chromatography.

Observation color of recovered catalyst is darker than fresh catalyst.

Catalyst recover and recycle: The recovered catalyst was recycled under identical conditions to obtain 88% triphenylphosphine based on iodobenzene. For third recycle catalyst was refluxed with 250 mg NiCl$_2$.6H$_2$O dissolved in 50% ethanol in water for 6 hours. Catalyst was extracted with water, ethanol and dried. This catalyst was recycled to obtain 90% triphenylphosphine.

Fresh catalyst under identical conditions in cyclohexane as solvent does not indicate leaching of nickel but yield of triphenyl phosphine was about 10% after 76 hours.

Example 481
Bromoanisol phosphination

Catalyst preparation: catalyst was prepared according to method described as deposition precipitation in coating pan
Catalyst specifications:

| | |
|---|---|
| Catalytic entity | PdAc$_2$.(bisdiphenylphosphinoethane tetrasulfonate)[1 miliatom of palladium] |
| Additive | bisdiphenylphosphinoethane tetrasulfonate 1 gm. |
| support | Gamma alumina 5 gm |
| Cured with | Barium nitrate |
| Method of preparation | Deposition precipitation in coating pan |
| Color of catalyst | Pale yellow |
| Metal content of prepared catalyst | 0.93 miliatom of palladium |

Procedure:

round bottomed flask equipped with reflux condenser was charged with catalyst 5 gm. To this solution of diphenyl phosphine 1 ml (5.75 mmol) in 30-ml dry degassed dimethylformamide was added at room temperature. Suspension was degassed with repetitive vacuum and argon flushing. After heating to 100° C. for 30 min. 10 mmol (1.87 gm.) 2-bromoanisol and 20 mmol (2.25 gm) diazabicyclooctane in 30 ml dimethylformamide was added and resulting solution was maintained at 100° C. Three additional portions of 1-ml diphenyl phosphine each were added at 12-hour interval thereafter. Reaction was continued for 76 hours. Reaction was stopped by cooling flask to room temperature. Catalyst was recovered by centrifugation and washed by dimethylformamide. Filtrates were combined and evaporated to obtain sticky residue, which was diluted with 50-ml tetrahydrofuran. Solution was analyzed with $^{31}$P NMR as described in previous example. 83% conversion of 2 bromoanisol was observed. Quantitative estimation of phosphines was not determined.

Example 482
Deuteration of $C_6H_6$ to $C_6D_6$
Catalyst specifications:

| | |
|---|---|
| Catalytic entity | Diphenyl phosphinoethane tetrasulphonate/ $RuCl_2COD$ 15 mg |
| Additive | Diphenyl phosphinoethane tetrasulphonate 25 mg/sodium phosphate 50 mg |
| Support | Bentonite 500 mg |
| Cured with | Saturated strontium chloride solution in water |
| Method of preparation | Fluidized bed |
| Color of catalyst | Pale yellow |

Catalyst pretreatment: catalyst was refluxed twice with 3-ml deuterium oxide recovered with centrifugation and dried under vacuum. This was essential to remove protons on the solid support.

Procedure:

100 mg of the catalyst was charged in the microreactor equipped with external magnetic stirrer 0.01 mol (0.78 g) benzene in 2 ml and deuterium oxide was added. Reaction vessel was heated to 110° C. with external heating. Agitation was started after attaining temperature. Reactor was maintained at these conditions for 24 hours. Reactor was cooled to −5° C. liquids were recovered and organic liquid was analyzed by NMR 88% labeling of deuterium using chloroform as internal standard.

Catalyst was recovered by centrifugation and recovered catalyst was dried under vacuum. This catalyst was recycled to obtain equivalent activity and selectivity.

While invention has been particularly shown and described with respect to preferred embodiments thereof, it will be understood by those skilled in the art that the forgoing and the other changes in form and detail may be made without departing from the spirit and scope of the invention.

What is claimed is:

1. A catalytic composition comprising a solid support having deposited thereon a solid catalytically active material that is substantially insoluble in organic and aqueous liquid media, the solid catalytically active material consisting of at least one catalytic active anionic entity together with group 2 metal ions.

2. A catalytic composition as claimed in claim 1 wherein the solid catalytically active material is molecularly well defined.

3. A catalytic composition as claimed in claim 1 wherein the solid support includes external and pore surfaces, and pores that predominantly have a diameter greater than about 20 Å, and wherein the solid catalytically active material is deposited on the external and pore surfaces of the solid support.

4. A catalytic composition as claimed in claim 1 wherein the solid support includes pores that have pore diameters ranging from about 3–3000 Å.

5. A catalytic composition as claimed in claim 1 wherein, the solid support is a chemically inactive solid material.

6. A catalytic composition as claimed in claim 1 wherein the solid support is porous and is powder, granules, flakes or pellets of regular or irregular shapes, sheets, monolith, ropes or woven fabric or fibrous solids.

7. A catalytic composition as claimed in claim 1 wherein the solid support is porous and is a thermally stable solid, insoluble in reaction media selected from the group consisting of organic, aqueous, fluorous, non-aqueous ionic liquids and supercritical fluid phases.

8. A catalytic composition as claimed in claim 1 wherein the catalytically active anionic entity is insoluble in reaction media selected from the group consisting of organic, aqueous, fluorous, non-aqueous ionic liquids and supercritical fluid phases.

9. A catalytic composition as claimed in claim 1 wherein the solid catalytically active material is a thermally stable solid material having a melting point greater than 100° C.

10. A catalytic composition as claimed in claim 1 further comprising a film of liquid with a boiling point of less than 300° C. deposited on the solid support.

11. A catalytic composition as claimed in claim 1 wherein the solid support having deposited thereon the solid catalytically active material remains as a stable composite solid when used as a catalyst for gaseous, liquid or gas-liquid phase reactions.

12. A catalytic composition as claimed in claim 11 wherein the liquid phase is selected from the group consisting of organic, aqueous, fluorous, non-aqueous ionic liquids and supercritical fluid phases and mixtures thereof containing reactants, products or promoters.

13. A catalytic composition as claimed in claim 1 wherein the catalytic composition remains as a physically stable composite solid when used as a catalyst for gaseous or liquid phase reactions over a temperature range of 78 to 300° C.

14. A catalytic composition as claimed in claim 1 wherein the catalytic composition remains as a physically stable composite solid when used as a catalyst for gaseous or liquid phase reactions over pressures ranging from 5 to 5000 psi.

15. A catalytic composition as claimed in claim 1 wherein the group 2 metal ion is a cation having +2 charge.

16. A catalytic composition as claimed in claim 1 wherein the group 2 metal is selected from the group consisting of calcium, strontium, barium and mixtures thereof.

17. A catalytic composition as claimed in claim 1 wherein the group 2 metal is selected individually or in combination with other group 2 metals.

18. A catalytic composition as claimed in claim 1 wherein the catalytically active anionic entity is an anion having, overall, a negative charge of at least two.

19. A catalytic composition as claimed in claim 1 wherein the catalytically active anionic entity is individually selected from the group consisting of metal complexes, quaternary compounds, metaloxoanions, polyoxometallates and combinations thereof.

20. A catalytic composition as claimed in claim 19 wherein the catalytically active anionic entity is a metal complex having a general formula

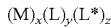

wherein M is a metal atom or ion selected from the group consisting of group 3, 4, 5, 6, 7, 11 or 12 of the periodic table of elements, x ranges from 1 to 60, L is selected from the group consisting of aliphatic, aromatic and heterocyclic ligands containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups individually selected from the group consisting of —$SO_3^-$, —$SO_2^-$, —$PO_3^{2-}$, —$COO^-$, —$O^-$, $AsO_3^{2-}$ and —S, y is at least 1, L* is a ligand selected from the group consisting of an organic anion, an inorganic anion and coordinating compounds containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group and z ranges from 0 to 7.

21. A catalytic composition as claimed in claim 19 wherein the catalytically active anionic entity is a quaternary compound having a general formula

wherein I=4 for $Y^1=N^1$, $P^+$, $As^+$; I=3 for $Y^1-S^+$ and $R^+$ is selected independently from the group consisting of alkyl, aryl, arylalkyl, alkylaryl, alkoxy, aryloxy, and cycloalkyl bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, and Z is an anion selected from the group consisting of an organic anion, an inorganic anion and a coordination complex anion.

22. A catalytic composition as claimed in claim 1 wherein the solid catalytically active material is deposited on the solid support along with at least one catalytically inert additive.

23. A catalytic composition as claimed in claim 22 wherein the catalytically inert additive is an anion having a negative charge of at least two.

24. A catalytic composition as claimed in claim 22 wherein the catalytically inert additive is an anion, which is independently selected from the group consisting of organic anions, inorganic anions and combinations thereof.

25. A catalytic composition as claimed in claim 22 wherein the catalytically inert additive is selected from the group consisting of ligands that contain at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^{-1}$.

26. A catalytic composition as claimed in claim 1 wherein an amount of the catalytically active anion entity employed is 40% weight or less of the catalytic composition.

27. A catalytic composition as claimed in claim 22 wherein an amount of the catalytically inert additive employed is in the proportion of 0 to 200 weight % of the catalytically active anion entity.

28. A process for the preparation of a catalytic formulation as a solid composite comprising fluidizing a porous solid support in a flow of gases and spraying a solution of a catalytically active entity and a catalytically inert additive such that the catalytically active entity and the catalytically inert additive are deposited on the porous solid support, wherein the fluidizing is continued for 1 to 48 hours, and subsequently spraying a solution of a group 2 metal compound, and fluidizing is further continued for 1 to 48 hours, and recovering solids, wherein the porous solid support is a thermally stable solid in reaction media selected from the group consisting of organic, aqueous, fluorous, non-aqueous ionic liquids and supercritical fluid phases, has a mean pore diameter in the range of about 70–3000 Å and is in a form of powder, granules, flakes or pellets of regular or irregular shapes, sheets, monolith, ropes or woven fabric of fibrous solids and wherein the catalytically inert additive is independently selected from the group consisting of anions having a negative charge of at least two comprising organic anions, inorganic anions, or a compound containing at least one radical selected from the group consisting of O, N, S, Se, Te, P, As, Sb, Bi, Si, olefin, and carbene that have attached thereto an oxy, alkyl, aryl, arylakyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$;

wherein the catalytically active entity is independently selected from the group consisting of metal complexes, quaternary compounds, metal oxo anions and polyoxymetallates and combinations thereof, wherein the metal complexes have a general formula

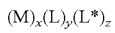

wherein M is a metal atom or ion selected from the group consisting of group 3, 4, 5, 6, 7, 11 and 12 of the periodic table of elements, x ranges from 1 to 60, L is an aliphatic, aromatic or heterocyclic ligand containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, y is at least 1, $L^*$ is a ligand selected from the group consisting of an organic anion, an inorganic anion and a coordinating compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group, and z ranges from 0 to 7, and wherein the quaternary compound has a general formula

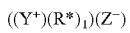

wherein I=4 or $Y^+=N^1$, $P^1$, $As^+$; I=3 for $Y^++S^+$ and $R^*$ is selected independently from the group consisting of alkyl, aryl, arylalkyl, alkylaryl, alkoxy, aryloxy, and cycloalkyl bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, and Z is an anion selected from the group consisting of an organic anion, an inorganic anion and a coordination complex anion, and wherein the group 2 metal compound comprises ions selected from the group consisting of $Ca^{+2}$, $Sr^{+2}$ and $Ba^{+2}$.

29. A process as claimed in claim 27 wherein the solvent employed to form a solution of the group 2 metal compound is aqueous, water miscible organic or a mixture thereof.

30. A catalytic composition comprising a solid support having deposited thereon a solid catalytically active material that is substantially insoluble in organic and aqueous liquid media, the solid catalytically active materials consisting of at least one catalytically active anionic entity and at least one catalytically inactive anionic additive that are together with group 2 metal ions.

31. A catalytic composition as claimed in claim 30 wherein the solid catalytically active material is molecularly well defined.

32. A catalytic composition as claimed in claim 30 wherein the solid support includes external and pore surfaces, and pores that predominantly have a diameter greater than about 20 Å, and wherein the solid catalytically active material is deposited on the external and pore surfaces of the solid support.

33. A catalytic composition as claimed in claim 30 wherein said solid support includes pores that have pore diameters ranging from about 3–3000 Å.

34. A catalytic composition as claimed in claim 30 wherein the solid support is a chemically inactive solid material.

35. A catalytic composition as claimed in claim 30 wherein the solid support is porous and is powder, granules, flakes or pellets of regular or irregular shapes, sheets, monolith, ropes or woven fabric of fibrous solids.

36. A catalytic composition as claimed in claim 30 wherein the solid support is porous and is a thermally stable solid, insoluble in reaction media selected from the group consisting of organic, aqueous, fluorous, non-aqueous ionic liquids and supercritical fluid phases.

37. A catalytic composition as claimed in claim 30 wherein the catalytically active anionic entity is insoluble in reaction media selected from the group consisting of organic, aqueous, fluorous, non-aqueous ionic liquids and supercritical fluid phases.

38. A catalytic composition as claimed in claim 30 wherein the solid catalytically active material is a thermally stable solid material having a melting point greater than 100° C.

39. A catalytic composition as claimed in claim 30 further comprising a film of liquid with boiling point of less than 300° C. deposited on the solid support.

40. A catalytic composition as claimed in claim 30 wherein the solid support having deposited thereon the solid catalytically active material remains as a stable composite solid when used as a catalyst for gaseous, liquid or gas-liquid phase reactions.

41. A catalytic composition as claimed in claim 40 wherein the liquid phase is selected from the group consisting of organic, aqueous, fluorous, non-aqueous ionic liquids and supercritical fluid phases and mixtures thereof containing reactants, products or promoters.

42. A catalytic composition as claimed in claim 30 wherein the catalytic composition remains as a physically stable composite solid when used as a catalyst in gaseous or liquid phase reactions over a temperature range of −78 to 300° C.

43. A catalytic composition as claimed in claim 30 wherein the catalytic composition remains as a physically stable composite solid when used as a catalyst in gaseous or liquid phase reactions over pressures ranging from 5 to 5000 psi.

44. A catalytic composition as claimed in claim 30 wherein the group 2 metal ion is a cation having +2 charge.

45. A catalytic composition as claimed in claim 30 wherein the group 2 metal is selected from the groups consisting of calcium, strontium, barium and mixtures thereof.

46. A catalytic composition as claimed in claim 30 wherein the group 2 metal is selected individually or in combination with other group 2 metals.

47. A catalytic composition as claimed in claim 30 wherein the catalytically active anionic entity is an anion having, overall, a negative charge of at least two.

48. A catalytic composition as claimed in claim 30 wherein the catalytically active anion entity is independently selected from the group consisting of metal complexes, quaternary compounds, metaloxoanions, polyoxometallates and combinations thereof.

49. A catalytic composition as claimed in claim 30 wherein an amount of the catalytically active anionic entity employed is 40% weight or less of the catalyst.

50. A catalytic composition as claimed in claim 30 wherein an amount of the catalytically inactive anionic additive employed is 0 to 20 weight % of the catalytically active anionic entity.

51. A process for the preparation of a catalytic formulation as a solid composite comprising tumbling a porous solid support in a rotating pan under a flow of gases, spraying a solution of a catalytically active entity and a catalytically inert additive such that the catalytically active entity and the catalytically inert additive are deposited on the porous solid support, the tumbling continuing for 1 to 48 hours, and subsequently spraying a solution of a group 2 metal compound, and then tumbling is further continued for 1 to 48 hours, and solids are recovered, wherein the porous solid support is a thermally stable solid in reaction media selected from the group consisting of organic, aqueous, fluorous, non-aqueous ionic liquids and supercritical fluid phases, has a mean pore diameter in the range of about 70–3000 Å and is in a form of powder, granules, flakes or pellets of regular or irregular shapes, sheets, monolith, ropes or woven fabric of fibrous solids and wherein the catalytically inert additive is independently selected from the group consisting of anions having a negative charge of at least two comprising organic anions, inorganic anions, or a compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of —$SO_3^-$, —$SO_2^-$, —$PO_3^{2-}$, —$COO^-$, —$O^-$, —$AsO_3^{2-}$ and —$S^-$;

wherein the catalytically active entity is independently selected from the group consisting of metal complexes, quaternary compounds, metal oxo anions and polyoxymetallates and combinations thereof, wherein the metal complexes have a general formula

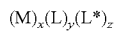

wherein M is a metal atom or ion selected from the group consisting of group 3, 4, 5, 6, 7, 11 and 12 of the periodic table of elements, x ranges from 1 to 60, L is an aliphatic, aromatic or heterocyclic ligand containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional group independently selected from the group consisting of —$SO_3^-$, —$SO_2^-$, —$PO_3^{2-}$, —$COO^-$, —$O^-$, $AsO_3^{2-}$ and —$S^-$, y is at least 1, L* is a ligand selected from the group consisting of an organic anion, an inorganic anion and a coordinating compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group, z ranges from 0 to 7 and wherein the quaternary compound has a general formula

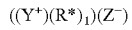

wherein I=4 for $Y^+=N^+$, $P^+$, $As^+$; I=3 for $Y^-=S^1$ and R* is selected independently from the group consisting of alkyl, aryl, arylalkyl, alkylaryl, alkoxy, aryloxy, and cycloalkyl bearing at least one or more negatively charged functional groups independently selected from the group consisting of —$SO_3^-$, —$SO_2^-$, —$PO_3^{2-}$, —$COO^-$, —$O^-$, $AsO_3^{2-}$ and $S^-$, and Z is an anion selected from the group consisting of an organic anion, an inorganic anion and a coordination complex anion and wherein the group 2 metal compound comprises ion selected from the group consisting of $Ca^{+2}$, $Sr^{+2}$ and $Ba^{+2}$.

52. A process as claimed in claim 51 wherein a solvent employed to form the solutions is aqueous, water miscible organic or a mixture thereof.

53. A process as claimed in claim 51 wherein the solutions are sprayed simultaneously or sequentially.

54. A process for the preparation of a catalytic formulation as a solid composite comprising depositing a group 2 metal compound on a porous solid support followed by drying and suspending the porous solid support having deposited thereon the group 2 metal compound in a water immiscible solvent to which a solution of a catalytically active entity and a catalytically inactive additive is added with agitation sufficient to maintain a suspension, and removal of a low boiling or azeotropic fraction of solvent, and aging the suspension for 1 to 48 hours,
  wherein the porous solid support is a thermally stable solid in reaction media selected from the group consisting of organic, aqueous, fluorous, non-aqueous ionic liquids and supercritical fluid phases, has a mean pore diameter in the range of about 3–3000 Å and is in a form of a powder, granules, flakes or pellets of regular or irregular shapes, sheets, monolith, ropes of woven fabric of fibrous solids and
  wherein the catalytically inactive additive is independently selected from the group consisting of anions having a charge of at least two comprising organic anions, inorganic anions, or a compound containing at least one substituent selected from the group consisting of O, N, S, Se, Te, P, As, Sb, Bi, Si, olefin, and carbene that have attached thereto an oxyl, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^{-1}$;
  wherein the catalytically active entity is independently selected from the group consisting of metal complexes, quaternary compounds, metal oxo anions and polyoxymetallates and combinations thereof,
  wherein the metal complexes have a general formula

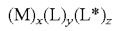

wherein M is a metal atom or ion selected from the group consisting of group 3, 4, 5, 6, 7, 11 and 12 of the periodic table of elements, x ranges from 1 to 60, L is an aliphatic, aromatic or heterocyclic ligand containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, y is at least 1, L* is a ligand selected from the group consisting of an organic amino, an inorganic anion and a coordinating compound containing at least one substituent selected from the group consisting of O, N, S, Se, Te, P, As, Sb, Bi, Si, olefin, and carbene that have attached thereto an oxy, alkyl, aryl, arylalkl, alkylaryl, alkoxy, aryloxy, or cycloalkyl group, z ranges from 0 to 7, and
  wherein the quaternary compound has a general formula

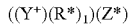

wherein I=4 for $Y^1=N^+$, $P^+$, $As^+$, I=3 for $Y^+-Y^1$; and R* is selected independently from the group consisting of alkyl, aryl, arylalkyl, alkylaryl, alkoxy, aryloxy, and cycloalkyl bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, and Z is anion selected from the group consisting of an organic anion, an inorganic anion and a coordination complex anion and wherein the group 2 metal compound comprises ions selected from the group consisting of $Ca^{+2}$, $Sr^{+2}$ and $Ba^{+2}$.

55. A process as claimed in claim 54 wherein a solvent employed to form a solution of the group 2 metal compound is an aqueous, water miscible organic or a mixture thereof.

56. A process as claimed 54 wherein the water immiscible organic solvent has a boiling point in a range of 40 to 200° C.

57. A process as claimed in claim 54 wherein the solid composite is recovered by centrifugation, decantation, or gravity settling, and is dried subsequently in a vacuum.

58. A process for the preparation of a catalytic formulation as a solid composite comprised of a porous solid support having deposited thereon a catalytically active solid, said process comprising impregnating the porous solid support with a solution of a catalytically inactive additive and a catalytically active entity, followed by during and suspending the porous solid support having deposited thereon the catalytically inactive additive and the catalytically active entity in a water immiscible solvent and adding a solution of a group 2 metal compound with agitation sufficient to maintain a suspension, and aging the suspension for 1 to 48 hours, and removal of low boiling or azeotropic fraction of solvent,
  wherein the porous solid support is a mechanically robust and thermally stable solid in reaction media selected from the group consisting of organic, aqueous, fluorous, non-aqueous ionic liquids and supercritical fluid phases, has a mean pore diameter in the range of about 70–3000 Å and is in a form of powder, granules, flakes or pellets of regular or irregular shapes, sheets, monolith, ropes or woven fabric of fibrous solids and
  wherein the catalytically inactive additive is independently selected from the group consisting of anions having a negative charge of at least two comprising organic anions, inorganic anions, or a compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $-AsO_3^{2-}$ and $-S^-$;
  wherein the catalytically active entity is independently selected from the group consisting of metal complexes, quaternary compounds, metal oxo anions and polyoxymetallates and combinations thereof,
  wherein the metal complexes have a general formula

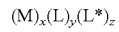

wherein M is a metal atom or ion selected from the group consisting of group 3, 4, 5, 6, 7, 11 and 12 of the periodic table of elements, x ranges from 1 to 60, L is an aliphatic, aromatic or heterocyclic ligand containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, y is at least 1, L* is a ligand selected from the group consisting of an organic anion, an inorganic anion and a coordinating compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group, z is from 0 to 7, and wherein the quaternary compound has a general formula $$((Y^+)(R^*)_l)(Z^-)$$

wherein I=4 for $Y^+=N^+$, $P^+$, $As^+$; I=3 for $Y^+=S^+$ and R* is selected independently from the group consisting of alkyl, aryl, arylalkyl, alkylaryl, alkoxy, aryloxy, and cycloalkyl bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$ and Z is an anion selected from the group consisting of organic anion, inorganic anion and coordination complex anion, and wherein the group 2 metal compound comprises ions selected from the group consisting of $Ca^{2+}$, $Sr^{2+}$ and $Ba^{2+}$.

59. A process as claimed in claim 58 wherein a solvent employed to form a solution of the group 2 metal compound is aqueous, water miscible organic or a mixture thereof.

60. A process as claimed in claim 58 wherein the water immiscible organic solvent has a boiling point in a range of 40 to 200° C.

61. A process according to claim 58 wherein the solid composite is recovered by centrifugation, decantation or gravity settling, and is dried subsequently in a vacuum.

62. A process for the preparation of a catalytic formulation as a solid composite comprised of a porous solid support having deposited thereon a catalytically active solid, said process comprising impregnating the porous solid support with a catalytically active entity and a catalytically inert additive followed by drying to obtain a dried porous solid support, adding the dried porous solid support having deposited thereon the catalytically active entity and the catalytically inert additive to a solution of a group 2 metal compound with simultaneous agitation, and aging the suspension for 1 to 48 hours with agitation, wherein the porous solid support is a mechanically robust and thermally stable solid in reaction media selected from the group consisting of organic, aqueous, fluorous, non-aqueous ionic liquids and supercritical fluid phases, has a mean pore diameter in the range of about 3–3000 Å and is in a form of powder, granules, flakes or pellets of rectangular or irregular shapes, sheets, monolith, ropes or woven fabric of fibrous solids and wherein the catalytically inert additive is independently selected from the group consisting of anions having a negative charge of at least two comprising organic anions, inorganic anions, or a compound containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-AsO_3^{2-}$ and $-S^-$;

wherein the catalytically active entity is independently selected from the group consisting of metal complexes, quaternary compounds, metal oxo anions and polyoxymetallates and combinations thereof, wherein the metal complexes have a general formula $$(M)_x(L)_y(L^*)_z$$

wherein M is a metal atom or ion selected from the group consisting of group 3, 4, 5, 6, 7, 11 and 12 of the periodic table of elements, x ranges from 1 to 60, L is an aliphatic, aromatic or heterocyclic ligand containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $-S^-$, y is at least 1, L* is a ligand selected from the group consisting of an organic anion, an inorganic anion and a coordinating compound containing at least one substituent selected from the group consisting of O, N, S, S, Se, Te, P, As, Sb, Bi, Si, olefin, and carbene that have attached thereto an oxy, alkyl, aryl, arylalkyl, alkylaryl, alkoxy, aryloxy, or cycloalkyl group, z ranges from 0 to 7 and wherein the quaternary compound has a general formula $$((Y^+)(R^*)_l)(Z^-)$$

wherein l=4 for $Y^+=N^+$, $P^+$, $As^+$; I=3 for $Y^1=S^+$ and R* is selected independently from the group consisting of alkyl, aryl, arylalkyl, alkylaryl, alkoxy, aryloxy, and cycloalkyl bearing at least one or more negatively charged functional groups independently selected from the group consisting of $-SO_3^-$, $-SO_2^-$, $-PO_3^{2-}$, $-COO^-$, $-O^-$, $AsO_3^{2-}$ and $S^-$ and Z is an anion selected from the group consisting of an organic anion, an inorganic anion and a coordination complex anion, and wherein the group 2 metal cation is selected from the group consisting of $Ca^{2+}$, $Sr^{2+}$ and $Ba^{2+}$.

63. A process as claimed in claim 62 wherein the solution of the group 2 compound includes a solvent that is aqueous, water miscible organic or a mixture thereof.

64. A process as claimed in claim 62 wherein the porous solid support having deposited thereon the catalytically active entity and the catalytically inert additive is added to the solution of group 2 metal compound, with simultaneous agitation, over a period of 10 to 1500 min.

65. A process as claimed in claim 62 wherein the solid composite is recovered by centrifugation, decantation, or gravity settling, and is dried subsequently in a vacuum.

66. A process for the preparation of a catalytic formulation as a solid composite comprised of a porous solid support having deposited thereon a catalytically active solid, said process comprising suspending the porous solid support in a liquid phase in which the porous solid support is insoluble to form a suspension, simultaneously adding to the suspension a solution of a catalytically inert additive and a catalytically active entity, and a solution of group 2 metal cation with sufficient agitation to maintain a suspension, and allowing to age for 1 to 48 hours, wherein the porous solid support is a thermally stable solid in reaction media selected from the group consisting of organic, aqueous, fluorous, non-aqueous ionic liquids and supercritical fluid phases, has a mean pore diameter in the range of about 3–3000 Å and is in a from of powder, granules, flakes or pellets of regulate or irregular shapes, sheets, monolith, ropes or woven fabric of fibrous solids, wherein the catalytically inert additive is independently selected from the group consisting of anions having a negative charge of at least two wherein, l=4 for $Y^1=N^1$, $P^1$, As*; 1–3 for $Y^+$—$S^+$ and $R^+$ is selected independently from the group consisting of alkyl, aryl, arylalkyl, alkylaryl, alkoxy, aryloxy, and cycloalkyl bearing at least one or more negatively charged functional groups independently selected from the group consisting of —SO₃⁻, —SO₂⁻, —PO₃²⁻, —COO⁻, —O⁻ ASO₃²⁻ and —S⁻, and Z is an anion selected from the group consisting of an organic anion, an inorganic anion and a coordination complex anion and wherein the group 2 metal cation is selected from the group consisting of Ca²⁺, Sr³⁺, and Ba²⁺.

67. A process as claimed in claim 66 wherein the solution of the group 2 metal cation is selected from the group consisting of aqueous, water miscible organic and mixtures thereof.

68. A process as claimed in claim 66 wherein the solution of catalytically inert additive and catalytically active entity and the solution of group 2 metal cation are added simultaneously over a period of 10 to 1500 min.

69. A process as claimed in claim 66 wherein the solid composite is recovered by centrifugation, decantation or gravity settling, and is dried subsequently in a vacuum.

70. A process for preparing a catalytically active solid composite comprising a solid support, said process comprising reacting a solution consisting of a catalytically inactive additive and a catalytically active entity with a solution of group 2 metal cation and obtaining a precipitate, wherein the catalytically inactive additive is independently selected from the group consisting of anions having a negative charge of at least two ligands containing at least one substituent selected from the group consisting of O, N, S, Se, Te, P, As, Sb, Bi, Si, and olefin that have attached thereto an oxy, alkyl, aryl, arylalkyl, alkylaryl, alkoxy, aryloxy, or cycloalkyl group bearing at least one or more negatively charged functional groups independently selected from the group consisting of —SO₃⁻, —SO₂⁻, —PO₃²⁻, COO⁻, —O⁻, AsO₃²⁻ and —S⁻, and combinations thereof;

wherein the catalytically active entity is independently selected from the group consisting of metal complexes, quaternary compounds, metal oxo anions, polyoxometallates and combinations thereof, wherein the metal complexes have a general formula

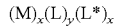

(M)ₓ(L)ᵧ(L*)ₓ wherein M is a metal atom or ion selected from the group consisting of group 3, 4, 5, 6, 7, 11 and 12 of the periodic table of elements x, ranges from 1 to 60, L is selected from the group consisting of aliphatic, aromatic and heterocyclic ligands containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group bearing at least one or more negatively charged functional groups independently selected from the group consisting of —SO₃⁻, —SO₂⁻, —PO₃²⁻, —COO⁻, —O⁻, AsO₃²⁻ and —S⁻, y is at least 1, L* is a ligand selected from the group consisting of an organic anion, an inorganic anion and coordinating compounds containing at least one substituent selected from the group consisting of O, N, S, Se, Te, P, As, Sb, Bi, Si, olefin, and carbene that have attached thereto an oxy, alkyl, aryl, arylalkyl, alkylaryl, alkoxy, aryloxy, or cycloalkyl group, z ranges from 0 to 7 and wherein the quaternary compound has a general formula

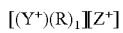

[(Y⁺)(R)ₗ][Z⁺]

wherein, I=4 for Y⁺=ᴺ⁺, P⁺, P⁺, As⁺, I=3 for Y¹=S¹ and R* is selected independently from the group consisting of alkyl, aryl, arylalkyl, alkylaryl, alkoxy, aryloxy, and cycloalkyl bearing at least one or more negative charged functional groups independently selected from the group consisting of —SO₃⁻, —SO₂⁻, —PO₃²⁻, —COO⁻, —O⁻, AsO₃²⁻ and —S⁻ and Z is an anion selected from the group consisting of an organic anion, an inorganic anion and a coordination complex anion; and wherein the group 2 metal cation is selected from the group consisting of Ca⁺², Sr⁺² and Ba⁺², wherein the process further comprises depositing the precipitate upon the solid support.

71. A process as claimed in claim 70 wherein an amount of the catalytically active entity employed is 40% weight or less of the catalytically active composition.

72. A process as claimed in claim 70 wherein an amount of the catalytically inactive additive employed is in the proportion of 0 to 20 weight % of the catalytically active entity.

73. A process as claimed in claim 70 wherein a film of liquid having a boiling point of less than 300° C. is deposited on the catalytically active composition.

* * * * *